(12) United States Patent
Brooks et al.

(10) Patent No.: US 10,388,894 B2
(45) Date of Patent: Aug. 20, 2019

(54) ORGANIC ELECTROLUMINESCENT MATERIALS AND DEVICES

(71) Applicant: Universal Display Corporation, Ewing, NJ (US)

(72) Inventors: Jason Brooks, Philadelphia, PA (US); Glenn Morello, Pittsburgh, PA (US); Chuanjun Xia, Lawrenceville, NJ (US); Jun Deng, Murrysville, PA (US)

(73) Assignee: Universal Display Corporation, Ewing, NJ (US)

( * ) Notice: Subject to any disclaimer, the term of this patent is extended or adjusted under 35 U.S.C. 154(b) by 194 days.

(21) Appl. No.: 15/067,536

(22) Filed: Mar. 11, 2016

(65) Prior Publication Data

US 2016/0233446 A1 Aug. 11, 2016

Related U.S. Application Data

(62) Division of application No. 13/787,169, filed on Mar. 6, 2013, now Pat. No. 9,312,505.

(60) Provisional application No. 61/705,400, filed on Sep. 25, 2012.

(51) Int. Cl.
| | |
|---|---|
| *H01L 51/54* | (2006.01) |
| *C09K 11/06* | (2006.01) |
| *H01L 51/00* | (2006.01) |
| *C07F 15/00* | (2006.01) |
| *H01L 51/50* | (2006.01) |
| *C09K 11/02* | (2006.01) |
| *H01L 51/52* | (2006.01) |

(52) U.S. Cl.
CPC ...... *H01L 51/0087* (2013.01); *C07F 15/0086* (2013.01); *C09K 11/025* (2013.01); *C09K 11/06* (2013.01); *H01L 51/0072* (2013.01); *H01L 51/0074* (2013.01); *H01L 51/50* (2013.01); *C09K 2211/1007* (2013.01); *C09K 2211/1029* (2013.01); *C09K 2211/1033* (2013.01); *C09K 2211/1044* (2013.01); *C09K 2211/185* (2013.01); *H01L 51/0085* (2013.01); *H01L 51/5016* (2013.01); *H01L 51/5028* (2013.01); *H01L 51/5206* (2013.01); *H01L 51/5221* (2013.01)

(58) Field of Classification Search
None
See application file for complete search history.

(56) References Cited

U.S. PATENT DOCUMENTS

| | | |
|---|---|---|
| 4,769,292 A | 9/1988 | Tang et al. |
| 5,061,569 A | 10/1991 | VanSlyke et al. |
| 5,247,190 A | 9/1993 | Friend et al. |
| 5,703,436 A | 12/1997 | Forrest et al. |
| 5,707,745 A | 1/1998 | Forrest et al. |
| 5,834,893 A | 11/1998 | Bulovic et al. |
| 5,844,363 A | 12/1998 | Gu et al. |
| 6,013,982 A | 1/2000 | Thompson et al. |
| 6,087,196 A | 7/2000 | Sturm et al. |
| 6,091,195 A | 7/2000 | Forrest et al. |
| 6,097,147 A | 8/2000 | Baldo et al. |
| 6,294,398 B1 | 9/2001 | Kim et al. |
| 6,303,238 B1 | 10/2001 | Thompson et al. |
| 6,337,102 B1 | 1/2002 | Forrest et al. |
| 6,468,819 B1 | 10/2002 | Kim et al. |
| 6,528,187 B1 | 3/2003 | Okada |
| 6,687,266 B1 | 2/2004 | Ma et al. |
| 6,835,469 B2 | 12/2004 | Kwong et al. |
| 6,893,743 B2 | 5/2005 | Sato et al. |
| 6,921,915 B2 | 7/2005 | Takiguchi et al. |
| 7,087,321 B2 | 8/2006 | Kwong et al. |
| 7,090,928 B2 | 8/2006 | Thompson et al. |
| 7,154,114 B2 | 12/2006 | Brooks et al. |
| 7,250,226 B2 | 7/2007 | Tokito et al. |
| 7,279,704 B2 | 10/2007 | Walters et al. |
| 7,332,232 B2 | 2/2008 | Ma et al. |
| 7,338,722 B2 | 3/2008 | Thompson et al. |

(Continued)

FOREIGN PATENT DOCUMENTS

| | | |
|---|---|---|
| EP | 0650955 | 5/1995 |
| EP | 1725079 | 11/2006 |

(Continued)

OTHER PUBLICATIONS

U.S. Appl. No. 61/490,111, filed May 26, 2011.

(Continued)

*Primary Examiner* — Marie R. Yamnitzky
(74) *Attorney, Agent, or Firm* — Duane Morris LLP

(57) ABSTRACT

Novel organometallic complexes having Formula (IV),

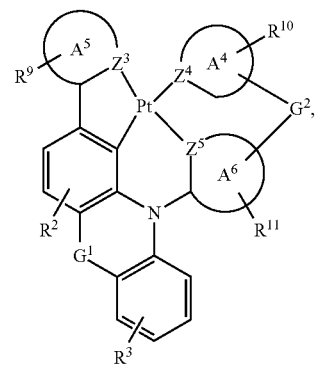

that are useful in organic light emitting devices are disclosed.

18 Claims, 7 Drawing Sheets

(56) References Cited

U.S. PATENT DOCUMENTS

| | | | |
|---|---|---|---|
| 7,393,599 B2 | 7/2008 | Thompson et al. | |
| 7,396,598 B2 | 7/2008 | Takeuchi et al. | |
| 7,431,968 B1 | 10/2008 | Shtein et al. | |
| 7,445,855 B2 | 11/2008 | Mackenzie et al. | |
| 7,534,505 B2 | 5/2009 | Lin et al. | |
| 9,238,668 B2 * | 1/2016 | Li et al. | C07F 15/0086 |
| 2002/0034656 A1 | 3/2002 | Thompson et al. | |
| 2002/0134984 A1 | 9/2002 | Igarashi | |
| 2002/0158242 A1 | 10/2002 | Son et al. | |
| 2003/0138657 A1 | 7/2003 | Li et al. | |
| 2003/0152802 A1 | 8/2003 | Tsuboyama et al. | |
| 2003/0162053 A1 | 8/2003 | Marks et al. | |
| 2003/0175553 A1 | 9/2003 | Thompson et al. | |
| 2003/0230980 A1 | 12/2003 | Forrest et al. | |
| 2004/0036077 A1 | 2/2004 | Ise | |
| 2004/0137267 A1 | 7/2004 | Igarashi et al. | |
| 2004/0137268 A1 | 7/2004 | Igarashi et al. | |
| 2004/0174116 A1 | 9/2004 | Lu et al. | |
| 2005/0006625 A1 | 1/2005 | Seo et al. | |
| 2005/0025993 A1 | 2/2005 | Thompson et al. | |
| 2005/0112407 A1 | 5/2005 | Ogasawara et al. | |
| 2005/0238919 A1 | 10/2005 | Ogasawara | |
| 2005/0244673 A1 | 11/2005 | Satoh et al. | |
| 2005/0260441 A1 | 11/2005 | Thompson et al. | |
| 2005/0260449 A1 | 11/2005 | Walters et al. | |
| 2006/0008670 A1 | 1/2006 | Lin et al. | |
| 2006/0202194 A1 | 9/2006 | Jeong et al. | |
| 2006/0240279 A1 | 10/2006 | Adamovich et al. | |
| 2006/0251923 A1 | 11/2006 | Lin et al. | |
| 2006/0263635 A1 | 11/2006 | Ise | |
| 2006/0280965 A1 | 12/2006 | Kwong et al. | |
| 2007/0190359 A1 | 8/2007 | Knowles et al. | |
| 2007/0278938 A1 | 12/2007 | Yabunouchi et al. | |
| 2008/0015355 A1 | 1/2008 | Schafer et al. | |
| 2008/0018221 A1 | 1/2008 | Egen et al. | |
| 2008/0106190 A1 | 5/2008 | Yabunouchi et al. | |
| 2008/0124572 A1 | 5/2008 | Mizuki et al. | |
| 2008/0220265 A1 | 9/2008 | Xia et al. | |
| 2008/0297033 A1 | 12/2008 | Knowles et al. | |
| 2009/0008605 A1 | 1/2009 | Kawamura et al. | |
| 2009/0009065 A1 | 1/2009 | Nishimura et al. | |
| 2009/0017330 A1 | 1/2009 | Iwakuma et al. | |
| 2009/0030202 A1 | 1/2009 | Iwakuma et al. | |
| 2009/0039776 A1 | 2/2009 | Yamada et al. | |
| 2009/0045730 A1 | 2/2009 | Nishimura et al. | |
| 2009/0045731 A1 | 2/2009 | Nishimura et al. | |
| 2009/0101870 A1 | 4/2009 | Prakash et al. | |
| 2009/0108737 A1 | 4/2009 | Kwong et al. | |
| 2009/0115316 A1 | 5/2009 | Zheng et al. | |
| 2009/0165846 A1 | 7/2009 | Johannes et al. | |
| 2009/0167162 A1 | 7/2009 | Lin et al. | |
| 2009/0179554 A1 | 7/2009 | Kuma et al. | |
| 2012/0302753 A1 | 11/2012 | Li et al. | |
| 2014/0091265 A1 | 4/2014 | Stoessel et al. | |

FOREIGN PATENT DOCUMENTS

| | | |
|---|---|---|
| EP | 2034538 | 3/2009 |
| JP | 200511610 | 1/2005 |
| JP | 2007123392 | 5/2007 |
| JP | 2007254297 | 10/2007 |
| JP | 2008074939 | 4/2008 |
| WO | 01/39234 | 5/2001 |
| WO | 02/02714 | 1/2002 |
| WO | 02/15645 | 2/2002 |
| WO | 03040257 | 5/2003 |
| WO | 03060956 | 7/2003 |
| WO | 2004093207 | 10/2004 |
| WO | 2004107822 | 12/2004 |
| WO | 2005014551 | 2/2005 |
| WO | 2005019373 | 3/2005 |
| WO | 2005030900 | 4/2005 |
| WO | 2005089025 | 9/2005 |
| WO | 2005123873 | 12/2005 |
| WO | 2006009024 | 1/2006 |
| WO | 2006056418 | 6/2006 |
| WO | 2006072002 | 7/2006 |
| WO | 2006082742 | 8/2006 |
| WO | 2006098120 | 9/2006 |
| WO | 2006100298 | 9/2006 |
| WO | 2006103874 | 10/2006 |
| WO | 2006114966 | 11/2006 |
| WO | 2006132173 | 12/2006 |
| WO | 2007002683 | 1/2007 |
| WO | 2007004380 | 1/2007 |
| WO | 2007063754 | 6/2007 |
| WO | 2007063796 | 6/2007 |
| WO | 2008056746 | 5/2008 |
| WO | 2008101842 | 8/2008 |
| WO | 2008132085 | 11/2008 |
| WO | 2009000673 | 12/2008 |
| WO | 2009003898 | 1/2009 |
| WO | 2009008311 | 1/2009 |
| WO | 2009018009 | 2/2009 |
| WO | 2009021126 | 2/2009 |
| WO | 2009050290 | 4/2009 |
| WO | 2009062578 | 5/2009 |
| WO | 2009063833 | 5/2009 |
| WO | 2009066778 | 5/2009 |
| WO | 2009066779 | 5/2009 |
| WO | 2009086028 | 7/2009 |
| WO | 2009100991 | 8/2009 |
| WO | 2012/163471 A1 | 12/2012 |

OTHER PUBLICATIONS

Adachi, Chihaya et al., "Organic Electroluminescent Device Having a Hole Conductor as an Emitting Layer," Appl. Phys. Lett., 55(15): 1489-1491 (1989).

Adachi, Chihaya et al., "Nearly 100% Internal Phosphorescence Efficiency in an Organic Light Emitting Device," J. Appl. Phys., 90(10): 5048-5051 (2001).

Adachi, Chihaya et al., "High-Efficiency Red Electrophosphorescence Devices," Appl. Phys. Lett., 78(11)1622-1624 (2001).

Aonuma, Masaki et al., "Material Design of Hole Transport Materials Capable of Thick-Film Formation in Organic Light Emitting Diodes," Appl. Phys. Lett., 90:183503-1-183503-3, (2007).

Baldo et al., Highly Efficient Phosphorescent Emission from Organic Electroluminescent Devices, Nature, vol. 395, 151-154, (1998).

Baldo et al., Very high-efficiency green organic light-emitting devices based on electrophosphorescence, Appl. Phys. Lett., vol. 75, No. 1, 4-6 (1999).

Gao, Zhiqiang et al., "Bright-Blue Electroluminescence From a Silyl-Substituted ter-(phenylene-vinylene) derivative," Appl. Phys. Lett., 74(6): 865-867 (1999).

Guo, Tzung-Fang et al., "Highly Efficient Electrophosphorescent Polymer Light-Emitting Devices," Organic Electronics, 1: 15-20 (2000).

Hamada, Yuji et al., "High Luminance in Organic Electroluminescent Devices with Bis(10-hydroxybenzo[h]quinolinato) beryllium as an Emitter," Chem. Lett., 905-906 (1993).

Holmes, R.J. et al., "Blue Organic Electrophosphorescence Using Exothermic Host-Guest Energy Transfer," Appl. Phys. Lett., 82(15):2422-2424 (2003).

Hu, Nan-Xing et al., "Novel High Tg Hole-Transport Molecules Based on Indolo[3,2-b]carbazoles for Organic Light-Emitting Devices," Synthetic Metals, 111-112:421-424 (2000).

Huang, Jinsong et al., "Highly Efficient Red-Emission Polymer Phosphorescent Light-Emitting Diodes Based on Two Novel Tris(1-phenylisoquinolinato-C2,N)iridium(III) Derivatives," Adv. Mater., 19:739-743 (2007).

Huang, Wei-Sheng et al., "Highly Phosphorescent Bis-Cyclometalated Iridium Complexes Containing Benzoimidazole-Based Ligands," Chem. Mater., 16(12):2480-2488 (2004).

Hung, L.S. et al., "Anode Modification in Organic Light-Emitting Diodes by Low-Frequency Plasma Polymerization of CHF3," Appl. Phys. Lett., 78(5):673-675 (2001).

Ikai, Masamichi et al., "Highly Efficient Phosphorescence From Organic Light-Emitting Devices with an Exciton-Block Layer," Appl. Phys. Lett., 79(2):156-158 (2001).

(56) References Cited

OTHER PUBLICATIONS

Ikeda, Hisao et al., "P-185 Low-Drive-Voltage OLEDs with a Buffer Layer Having Molybdenum Oxide," SID Symposium Digest, 37:923-926 (2006).
Inada, Hiroshi and Shirota, Yasuhiko, "1,3,5-Tris[4-(diphenylamino)phenyl]benzene and its Methylsubstituted Derivatives as a Novel Class of Amorphous Molecular Materials," J. Mater. Chem., 3(3):319-320 (1993).
Kanno, Hiroshi et al., "Highly Efficient and Stable Red Phosphorescent Organic Light-Emitting Device Using bis[2-(2-benzothiazoyl)phenolato]zinc(II) as host material," Appl. Phys. Lett., 90:123509-1-123509-3 (2007).
Kido, Junji et al., 1,2,4-Triazole Derivative as an Electron Transport Layer in Organic Electroluminescent Devices, Jpn. J. Appl. Phys., 32:L917-L920 (1993).
Kuwabara, Yoshiyuki et al., "Thermally Stable Multilayered Organic Electroluminescent Devices Using Novel Starburst Molecules, 4,4',4"-Tri(N-carbazolyl)triphenylamine (TCTA) and 4,4',4"-Tris(3-methylphenylphenyl-amino)triphenylamine (m-MTDATA), as Hole-Transport Materials," Adv. Mater., 6(9):677-679 (1994).
Kwong, Raymond C. et al., "High Operational Stability of Electrophosphorescent Devices," Appl. Phys. Lett., 81(1) 162-164 (2002).
Lamansky, Sergey et al., "Synthesis and Characterization of Phosphorescent Cyclometalated Iridium Complexes," Inorg. Chem., 40(7):1704-1711 (2001).
Lee, Chang-Lyoul et al., "Polymer Phosphorescent Light-Emitting Devices Doped with Tris(2-phenylpyridine) Iridium as a Triplet Emitter," Appl. Phys. Lett., 77(15):2280-2282 (2000).
Lo, Shih-Chun et al., "Blue Phosphorescence from Iridium(III) Complexes at Room Temperature," Chem. Mater., 18 (21)5119-5129 (2006).
Ma, Yuguang et al., "Triplet Luminescent Dinuclear-Gold(I) Complex-Based Light-Emitting Diodes with Low Turn-On voltage," Appl. Phys. Lett., 74(10)1361-1363 (1999).
Mi, Bao-Xiu et al., "Thermally Stable Hole-Transporting Material for Organic Light-Emitting Diode an Isoindole Derivative," Chem. Mater., 15(16):3148-3151 (2003).
Nishida, Jun-ichi et al., "Preparation, Characterization, and Electroluminescence Characteristics of α-Diimine-type Platinum(II) Complexes with Perfluorinated Phenyl Groups as Ligands," Chem. Lett., 34(4): 592-593 (2005).
Niu, Yu-Hua et al., "Highly Efficient Electrophosphorescent Devices with Saturated Red Emission from a Neutral Osmium Complex," Chem. Mater., 17(13):3532-3536 (2005).
Noda, Tetsuya and Shirota,Yasuhiko, "5,5'-Bis(dimesitylboryl)-2,2'-bithiophene and 5,5"-Bis (dimesitylboryl)-2,2'5',2"-terthiophene as a Novel Family of Electron-Transporting Amorphous Molecular Materials," J. Am. Chem. Soc., 120 (37):9714-9715 (1998).

Okumoto, Kenji et al., "Green Fluorescent Organic Light-Emitting Device with External Quantum Efficiency of Nearly 10%," Appl. Phys. Lett., 89:063504-1-063504-3 (2006).
Palilis, Leonidas C., "High Efficiency Molecular Organic Light-Emitting Diodes Based on Silole Derivatives and Their Exciplexes," Organic Electronics, 4:113-121 (2003).
Paulose, Betty Marie Jennifer S. et al., "First Examples of Alkenyl Pyridines as Organic Ligands for Phosphorescent Iridium Complexes," Adv. Mater., 16(22):2003-2007 (2004).
Ranjan, Sudhir et al., "Realizing Green Phosphorescent Light-Emitting Materials from Rhenium(I) Pyrazolato Diimine Complexes," Inorg. Chem., 42(4):1248-1255 (2003).
Sakamoto, Youichi et al., "Synthesis, Characterization, and Electron-Transport Property of Perfluorinated Phenylene Dendrimers," J. Am. Chem. Soc., 122(8):1832-1833 (2000).
Salbeck, J. et al., "Low Molecular Organic Glasses for Blue Electroluminescence," Synthetic Metals, 91: 209-215 (1997).
Shirota, Yasuhiko et al., "Starburst Molecules Based on pi-Electron Systems as Materials for Organic Electroluminescent Devices," Journal of Luminescence, 72-74:985-991 (1997).
Sotoyama, Wataru et al., "Efficient Organic Light-Emitting Diodes with Phosphorescent Platinum Complexes Containing N∧C∧N-Coordinating Tridentate Ligand," Appl. Phys. Lett., 86:153505-1-153505-3 (2005).
Sun, Yiru and Forrest, Stephen R., "High-Efficiency White Organic Light Emitting Devices with Three Separate Phosphorescent Emission Layers," Appl. Phys. Lett., 91:263503-1-263503-3 (2007).
T. Östergård et al., "Langmuir-Blodgett Light-Emitting Diodes of Poly(3-Hexylthiophene) Electro-Optical Characteristics Related to Structure," Synthetic Metals, 88:171-177 (1997).
Takizawa, Shin-ya et al., "Phosphorescent Iridium Complexes Based on 2-Phenylimidazo[1,2- α]pyridine Ligands Tuning of Emission Color toward the Blue Region and Application to Polymer Light-Emitting Devices," Inorg. Chem., 46(10):4308-4319 (2007).
Tang, C.W. and VanSlyke, S.A., "Organic Electroluminescent Diodes," Appl. Phys. Lett., 51(12):913-915 (1987).
Tung, Yung-Liang et al., "Organic Light-Emitting Diodes Based on Charge-Neutral Ru II PHosphorescent Emitters," Adv. Mater., 17(8)1059-1064 (2005).
Van Slyke, S. A. et al., "Organic Electroluminescent Devices with Improved Stability," Appl. Phys. Lett., 69(15):2160-2162 (1996).
Wang, Y. et al., "Highly Efficient Electroluminescent Materials Based on Fluorinated Organometallic Iridium Compounds," Appl. Phys. Lett., 79(4):449-451 (2001).
Wong, Keith Man-Chung et al., A Novel Class of Phosphorescent Gold(III) Alkynyl-Based Organic Light-Emitting Devices with Tunable Colour, Chem. Commun., 2906-2908 (2005).
Wong, Wai-Yeung, "Multifunctional Iridium Complexes Based on Carbazole Modules as Highly Efficient Electrophosphors," Angew. Chem. Int. Ed., 45:7800-7803 (2006).

* cited by examiner

ORGANIC ELECTROLUMINESCENT MATERIALS AND DEVICES

CROSS-REFERENCE TO RELATED APPLICATIONS

This application is a division of U.S. patent application Ser. No. 13/787,169, filed Mar. 6, 2013, which claims priority to U.S. Provisional Application Ser. No. 61/705,400, filed Sep. 25, 2012, the entire contents of which are incorporated herein by reference.

JOINT RESEARCH AGREEMENT

The claimed invention was made by, on behalf of, and/or in connection with one or more of the following parties to a joint university corporation research agreement: Regents of the University of Michigan, Princeton University, University of Southern California, and the Universal Display Corporation. The agreement was in effect on and before the date the claimed invention was made, and the claimed invention was made as a result of activities undertaken within the scope of the agreement.

FIELD OF THE INVENTION

The present invention relates to organic light emitting devices (OLEDs). In particular, the invention relates to metal complexes having a bridged N,N-diaryl ligand and their use in various devices, including OLEDs.

BACKGROUND

Opto-electronic devices that make use of organic materials are becoming increasingly desirable for a number of reasons. Many of the materials used to make such devices are relatively inexpensive, so organic opto-electronic devices have the potential for cost advantages over inorganic devices. In addition, the inherent properties of organic materials, such as their flexibility, may make them well suited for particular applications such as fabrication on a flexible substrate. Examples of organic opto-electronic devices include organic light emitting devices (OLEDs), organic phototransistors, organic photovoltaic cells, and organic photodetectors. For OLEDs, the organic materials may have performance advantages over conventional materials. For example, the wavelength at which an organic emissive layer emits light may generally be readily tuned with appropriate dopants.

OLEDs make use of thin organic films that emit light when voltage is applied across the device. OLEDs are becoming an increasingly interesting technology for use in applications such as flat panel displays, illumination, and backlighting. Several OLED materials and configurations are described in U.S. Pat. Nos. 5,844,363, 6,303,238, and 5,707,745, which are incorporated herein by reference in their entirety, One application for phosphorescent emissive molecules is a full color display. Industry standards for such a display call for pixels adapted to emit particular colors, referred to as "saturated" colors. In particular, these standards call for saturated red, green, and blue pixels. Color may be measured using CIE coordinates, which are well known to the art.

One example of a green emissive molecule is tris(2-phenylpyridine) iridium, denoted Ir(ppy)$_3$, which has the following structure:

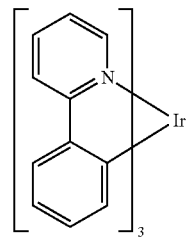

In this, and later figures herein, we depict the dative bond from nitrogen to metal (here, Ir) as a straight line.

As used herein, the term "organic" includes polymeric materials as well as small molecule organic materials that may be used to fabricate organic opto-electronic devices. "Small molecule" refers to any organic material that is not a polymer, and "small molecules" may actually be quite large. Small molecules may include repeat units in some circumstances. For example, using a long chain alkyl group as a substituent does not remove a molecule from the "small molecule" class. Small molecules may also be incorporated into polymers, for example as a pendent group on a polymer backbone or as a part of the backbone. Small molecules may also serve as the core moiety of a dendrimer, which consists of a series of chemical shells built on the core moiety. The core moiety of a dendrimer may be a fluorescent or phosphorescent small molecule emitter. A dendrimer may be a "small molecule," and it is believed that all dendrimers currently used in the field of LEDs are small molecules.

As used herein, "top" means furthest away from the substrate, while "bottom" means closest to the substrate. Where a first layer is described as "disposed over" a second layer, the first layer is disposed further away from substrate. There may be other layers between the first and second layer, unless it is specified that the first layer is "in contact with" the second layer. For example, a cathode may be described as "disposed over" an anode, even though there are various organic layers in between.

As used herein, "solution processible" means capable of being dissolved, dispersed, or transported in and/or deposited from a liquid medium, either in solution or suspension form.

A ligand may be referred to as "photoactive" when it is believed that the ligand directly contributes to the photoactive properties of an emissive material. A ligand may be referred to as "ancillary" when it is believed that the ligand does not contribute to the photoactive properties of an emissive material, although an ancillary ligand may alter the properties of a photoactive ligand.

As used herein, and as would be generally understood by one skilled in the art, a first "Highest Occupied Molecular Orbital" (HOMO) or "Lowest Unoccupied Molecular Orbital" (LUMO) energy level is "greater than" or "higher than" a second HOMO or :LUMO energy level if the first energy level is closer to the vacuum energy level. Since ionization potentials (IP) are measured as a negative energy relative to a vacuum level, a higher HOMO energy level corresponds to an IP having a smaller absolute value (an IP that is less negative). Similarly, a higher LUMO energy level corresponds to an electron affinity (EA) having a smaller absolute value (an EA that is less negative). On a conventional energy level diagram, with the vacuum level at the top, the LUMO energy level of a material is higher than the HOMO energy level of the same material. A "higher"

HOMO or LUMO energy level appears closer to the top of such a diagram than a "lower" HOMO or LUMO energy level.

As used herein, and as would be generally understood by one skilled in the art, a first work function is "greater than" or "higher than" a second work function if the first work function has a higher absolute value. Because work functions are generally measured as negative numbers relative to vacuum level, this means that a "higher" work function is more negative. On a conventional energy level diagram, with the vacuum level at the top, a "higher" work function is illustrated as further away from the vacuum level in the downward direction. Thus, the definitions of HOMO and LUMO energy levels follow a different convention than work functions.

More details on OLEDs, and the definitions described above, can be found in U.S. Pat. No. 7,279,704, which is incorporated herein by reference in its entirety.

SUMMARY OF THE INVENTION

In at least one aspect, the invention provides metal complexes having an N,N-diaryl ligand, such as compounds having Formula (I):

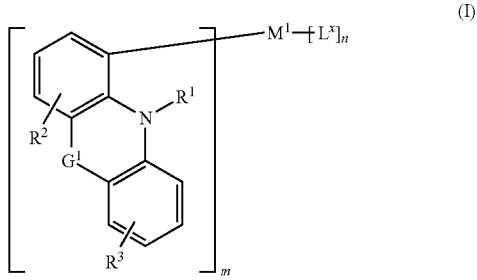

(I)

wherein each $L^x$ is independently a monodentate ligand, and any two adjacent may optionally combine to form a bidentate ligand; wherein $M^1$ is cobalt(I), rhodium(I), iridium(I), nickel(II), platinum(II), palladium(H); silver(III) gold(III), or copper(III); wherein m is a value from 1 to the maximum number of ligands that may be attached to $M^1$; wherein m+n is the maximum number of ligands that may he attached to $M^1$; wherein is $G^1$ is O or $CR^4R^5$; wherein $R^1$ is selected from the group consisting of hydrogen, deuterium, halide, alkyl, cycloalkyl, heteroalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof, wherein $R^2$ represents mono-, di-, or tri-substitution, wherein each $R^2$ is selected independently from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrite, isonitrile, sulfanyl, sulfinyl, sulfonyl, phosphino, and combinations thereof, and wherein any two adjacent $R^2$ may optionally combine to form a ring, which can be further substituted; wherein $R^3$ represents mono-, tri-, or tetra-substitution, wherein each $R^3$ is selected independently from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof, and wherein any two adjacent $R^3$ may optionally combine to form a ring, which can be further substituted; wherein $R^4$ and $R^5$ are independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, sulfanyl, sulfinyl, sulfonyl, phosphino, and combinations thereof, and wherein $R^4$ and $R^5$ may optionally combine to form a ring, which can be further substituted; wherein $R^1$ may optionally combine with any $R^1$ to form a ring system, which can be further substituted; wherein any of $R^4$ or $R^5$ may optionally combine with any $R^2$ or $R^3$ to form a ring system, which can be further substituted; and wherein any of $R^1$, $R^2$, or $R^3$ may optionally combine with one or more $L^x$ to form a bidentate, tridentate, or tetradentate ligand.

In some embodiments, $M^1$ is platinum(II), palladium(II), or gold(III). In some other embodiments, $M^1$ is platinum (II).

In some embodiments, $G^1$ is O, $C(CH_3)_2$, or $C(C_6H_5)_2$.

In some embodiments, the metal complex is a compound having Formula (II).

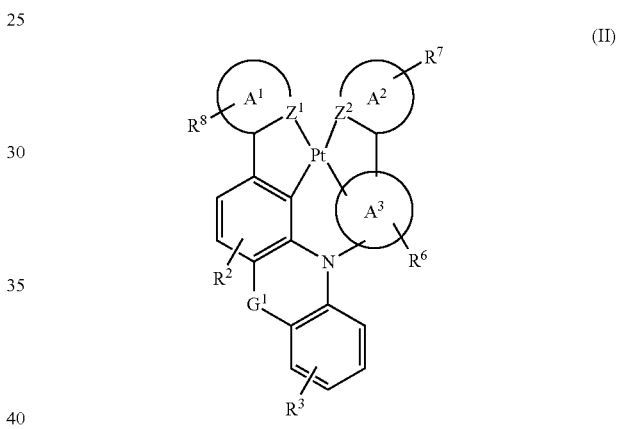

(II)

wherein rings $A^1$, $A^2$, and $A^3$ are independently five- or six-membered carbocyclic or heterocyclic aromatic rings having 0-3 nitrogen atoms and 0-1 additional heteroatoms selected from the group consisting of oxygen, sulfur, and selenium; $Z^1$ and $Z^2$ are independently carbon or nitrogen; wherein $R^2$ represents mono- or di-substitution, wherein each $R^2$ is selected independently from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof, and wherein any two adjacent $R^2$ may optionally combine to form a ring, which can be further substituted; wherein $R^3$ represents mono-, di-, tri-, or tetra-substitution, wherein each $R^3$ is selected independently from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof, and wherein any two adjacent $R^3$ may optionally combine to form a ring, which can be further substituted; wherein $R^6$ represents mono-, di-, or tri-substitution, wherein each $R^6$ is selected independently from the group consisting of hydrogen, deuterium, halide, alkyl, cyckalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof, and wherein any two adjacent $R^6$ may optionally combine to form a ring, which can be further substituted; wherein $R^7$ and $R^8$ represent mono-, di-, tri-, or tetra-substitution, wherein each $R^7$ or $R^8$ is selected independently from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof, and wherein any two adjacent $R^7$ or any two adjacent $R^8$ may optionally combine to form a ring, which can be further substituted; wherein any $R^3$ may optionally combine with any $R^6$ to form a ring system, which can be further substituted; wherein any $R^2$ may optionally combine with any $R^8$ to form a ring system, which can be further substituted; and wherein any $R^6$ may optionally combine with any $R^7$ to form a ring system, which can be further substituted; wherein any $R^7$ may optionally combine with any $R^8$ to form a ring system, which can be further substituted. The other variables have the definitions provided in the above embodiments.

In some such embodiments, the metal complex is a compound having Formula (IIa):

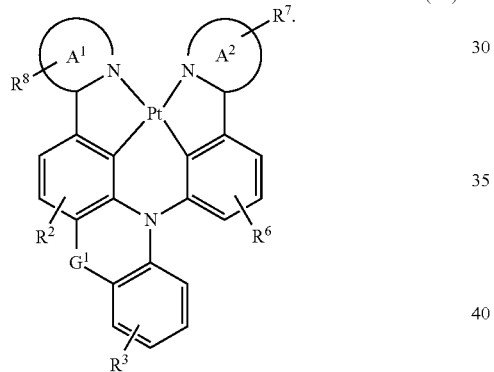

(IIa)

In some other such embodiments, the metal complex is a compound selected from the group consisting of:

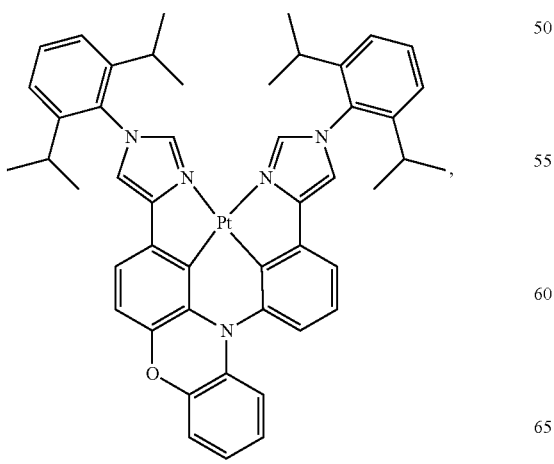

Compound 1

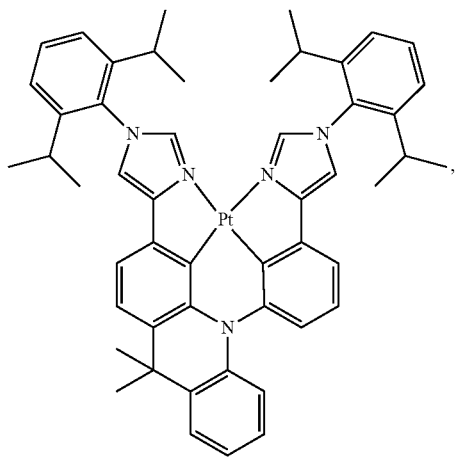

Compound 2

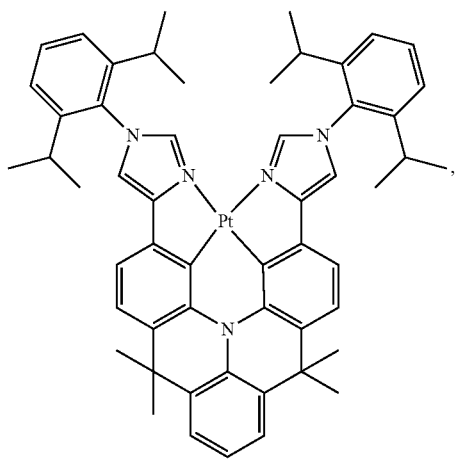

Compound 3

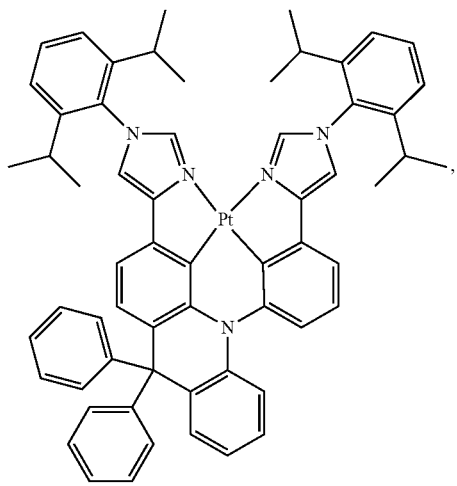

Compound 4

-continued
Compound 5
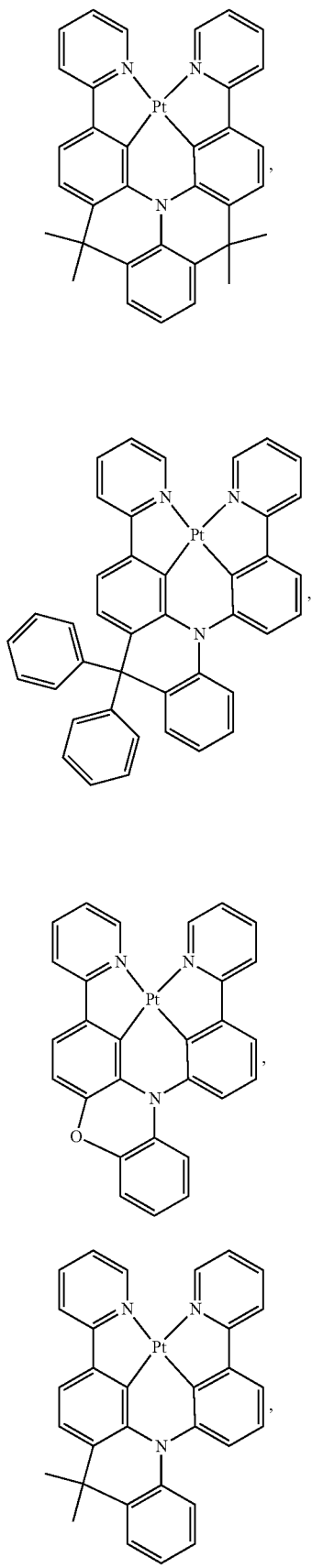
Compound 6
Compound 7
Compound 8
Compound 9
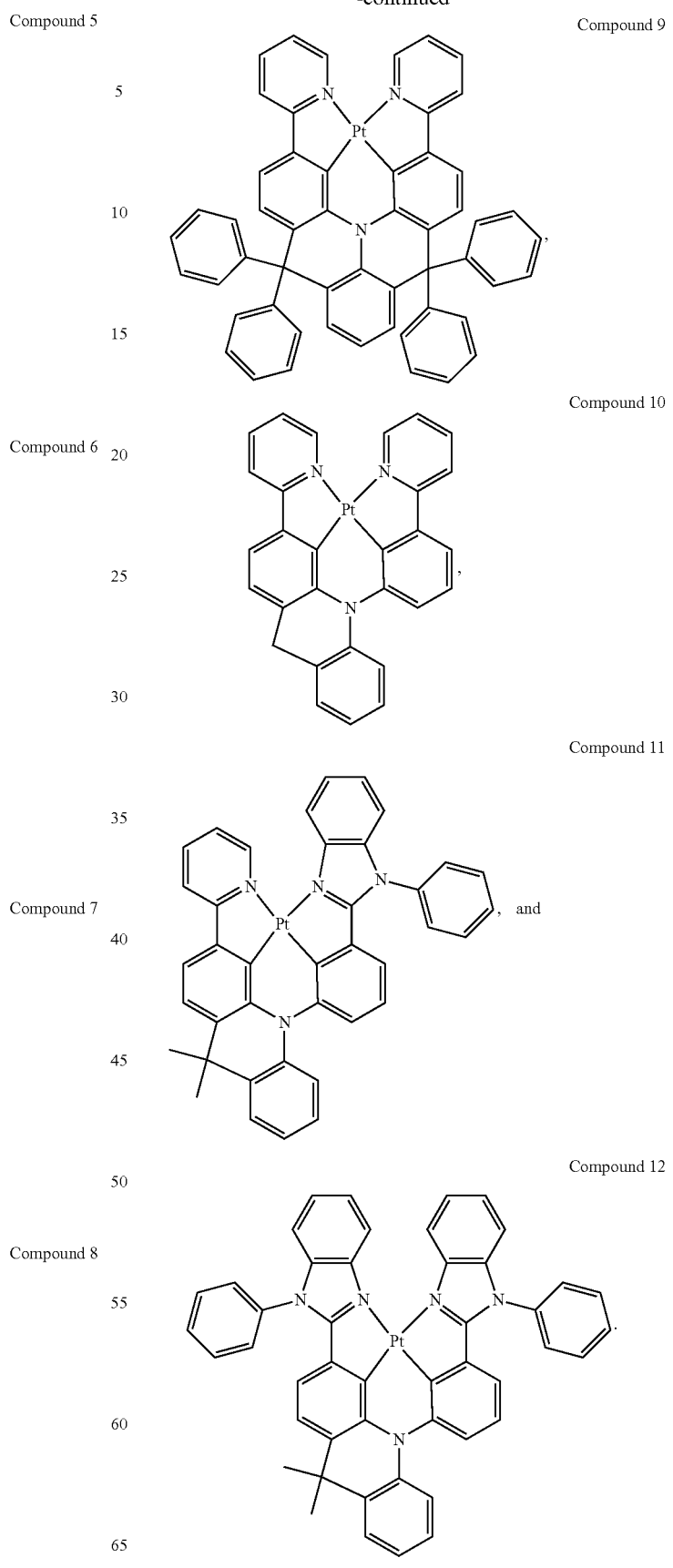
Compound 10
Compound 11
and
Compound 12

In some embodiments, the metal complex is a compound having Formula (IV):

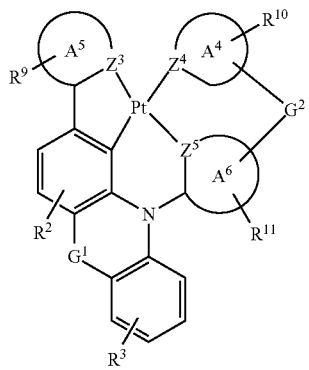

(IV)

wherein rings $A^4$, $A^5$, and $A^6$ are independently five- or six-membered carbocyclic or heterocyclic aromatic rings having 0-3 nitrogen atoms and 0-1 additional heteroatoms selected from the group consisting of oxygen, sulfur, and selenium; wherein $Z^3$, $Z^4$, and $Z^5$ are independently carbon or nitrogen; wherein $G^2$ is oxygen, sulfur, $CR^{12}R^{12a}$, $SiR^{12}R^{12a}$, or $NR^{12}$, wherein each $R^{12}$ and $R^{12a}$ is selected independently from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl aryl, heteroaryl, acyl, carbonyl, carboxylic acids, ester, nitrile, isonitrile, sulfanyl, sulfinyl, sulfonyl, phosphino, and combinations thereof and wherein $R^{12}$ and $R^{12a}$ may optionally combine with each other or with any one $R^{10}$ or $R^{11}$ to form a ring system, which can be further substituted; wherein $R^9$ and $R^{10}$ represent mono-, di-, tri-, or tetra-substitution, wherein each $R^9$ or $R^{10}$ is selected independently from the group consisting of hydrogen, deuterium, halide, alkyl, cloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl sulfinyl, sulfonyl, phosphino, and combinations thereof, and wherein any two adjacent $R^9$ or any two adjacent $R^{10}$ may optionally combine to form a ring, which can be further substituted; wherein $R^{11}$ represents mono-, di-, or tri-substitution, wherein each is selected independently from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, heteroaryl, acyl, carbonyl, carboxylic acids, ester, nitrile, sulfanyl, sulfinyl, sulfonyl, phosphino, and combinations thereof and wherein any two adjacent $R^{11}$ may optionally combine to form a ring, which can be further substituted; wherein any $R^3$ may optionally combine with any $R^{11}$ to form a ring system, which can be further substituted; and wherein any $R^2$ may optionally combine with any $R^9$ to form a ring system, which can be further substituted. The other variables have the definitions provided in the above embodiments.

In some such embodiments, the metal complex is a compound having Formula (IVa):

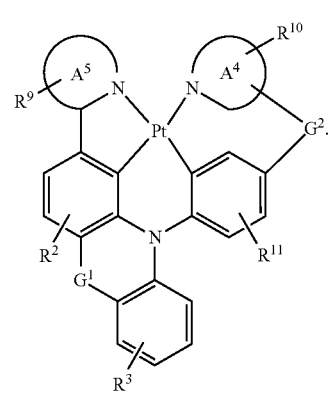

(IVa)

In some embodiments where the metal complex has a Formula (IV) or For a (IVa), $G^2$ is $NR^{12}$, and $R^{12}$ is phenyl.

In some other embodiments, the metal complex is a compound selected from the group consisting of:

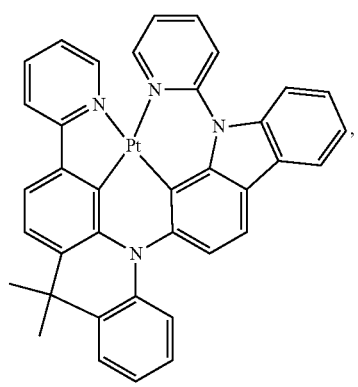

Compound 13

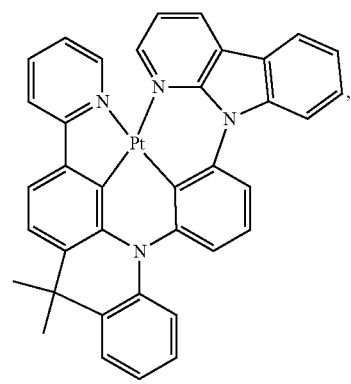

Compound 14

-continued
Compound 15
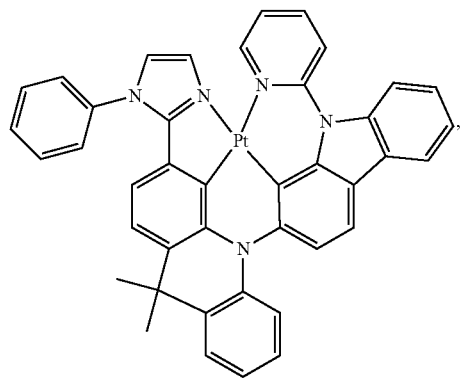
Compound 16
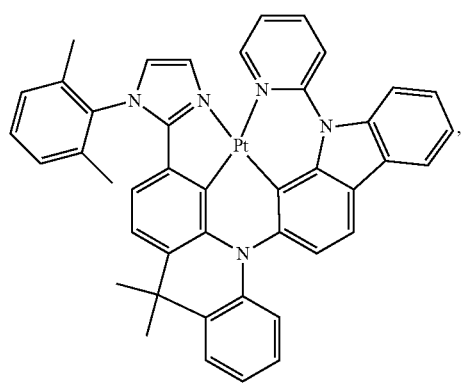
Compound 17
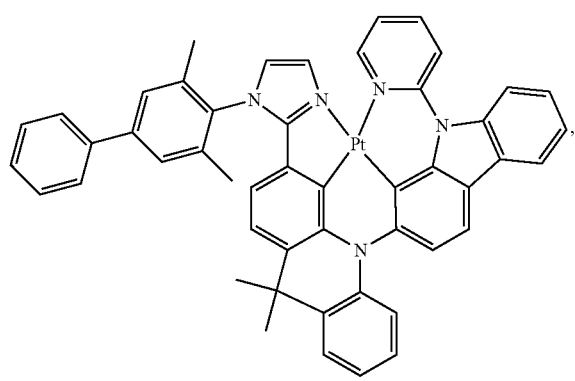
Compound 18
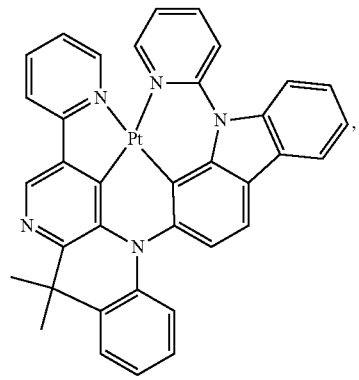
-continued
Compound 19
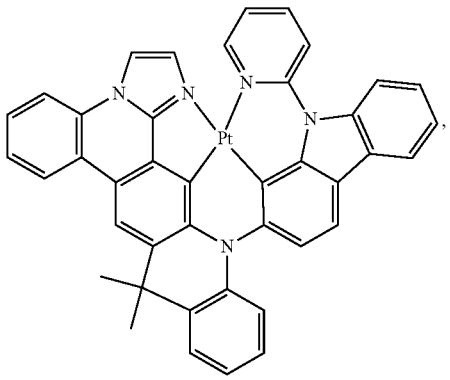
Compound 20
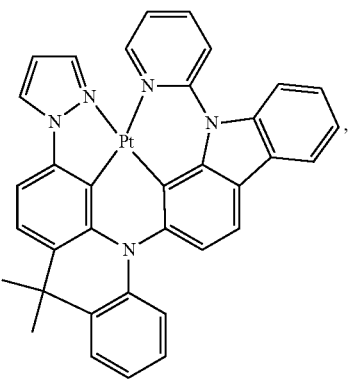
Compound 21
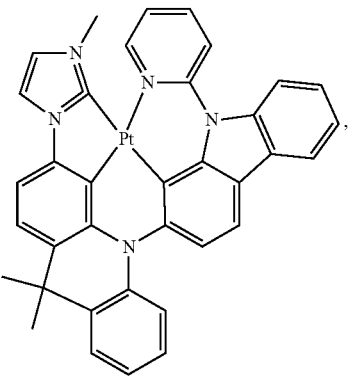
Compound 22
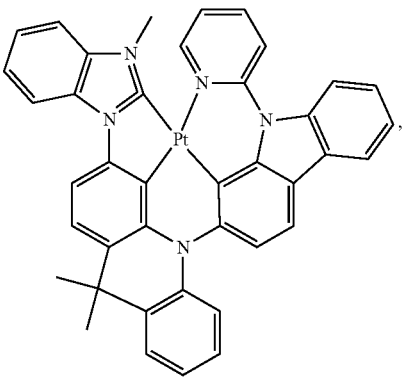

Compound 23

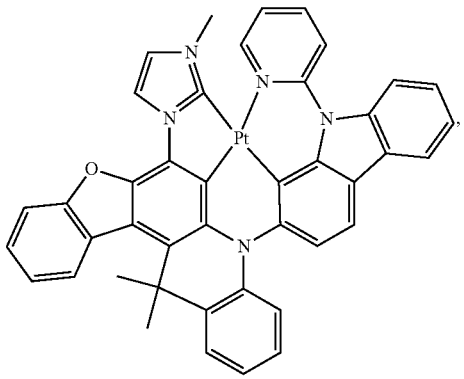

Compound 24

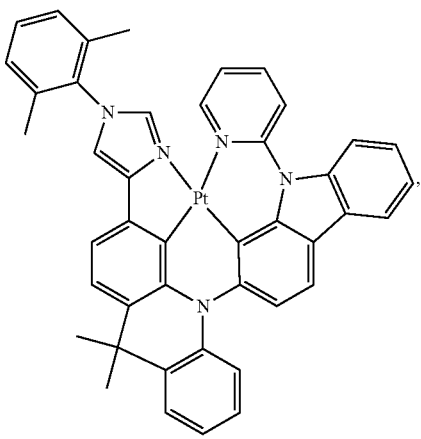

Compound 25

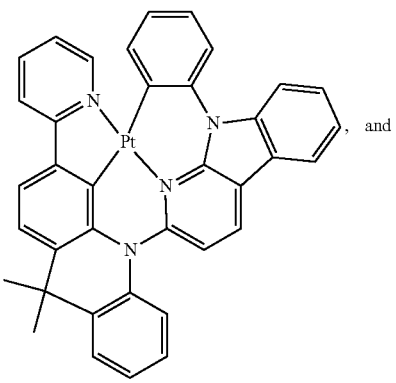, and

Compound 26

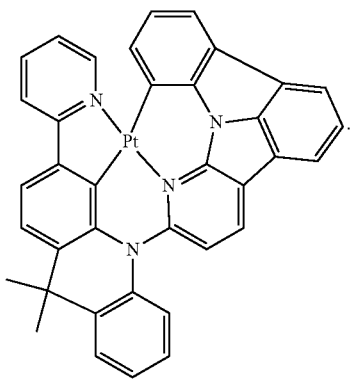.

In some embodiments, the metal complex is a compound having Formula (V):

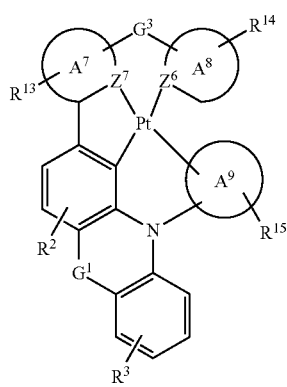

(V)

wherein rings $A^7$, $A^8$, and $A^9$ are independently five- or six-membered carboyclic or heterocyclic aromatic rings having 0-3 nitrogen atoms and 0-1 additional heteroatoms selected from the group consisting of oxygen, sulfur, and selenium; wherein $Z^6$ and $Z^7$ independently are carbon or nitrogen; $G^3$ is oxygen, sulfur, $CR^{16}R^{16a}$, $SiR^{16}R^{16a}$, or $NR^{16}$; wherein each $R^{16}$ and $R^{16a}$ is selected independently from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof, and wherein $R^{16}$ and $R^{16a}$ may optionally combine with each other or with any one $R^{13}$ or $R^{14}$ to form a ring system, which can be further substituted; wherein $R^{13}$ and $R^{14}$ represent mono-, di-, or tri-substitution, wherein each $R^{13}$ or $R^{14}$ is selected independently from the group consisting of hydrogen, deuterium, halide, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof, and wherein any two adjacent $R^{13}$ or any two adjacent $R^{14}$ may optionally combine to form a ring, which can be further substituted; wherein $R^{15}$ represents mono-, di-, tri- or tetra-substitution, wherein each $R^{15}$ is selected independently from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof, and wherein any two adjacent $R^{15}$ may optionally combine to form a ring, which can be further substituted; wherein any $R^2$ may optionally combine with any $R^{13}$ to form a ring system, which can be further substituted; and wherein any $R^{14}$ may optionally combine with any $R^{15}$ to form a ring system, which can be further substituted. The other variables have the definitions provided in the above embodiments.

In some such embodiments, the metal complex is a compound having Formula (Va):

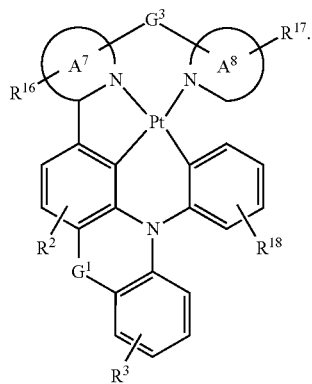
(Va)
In some embodiments where the metal complex has a Formula (V) or Formula (Va), $G^3$ is $NR^{16}$, and $R^{16}$ is phenyl.
In some other embodiments, the metal complex is a compound selected from the group consisting of:
Compound 27
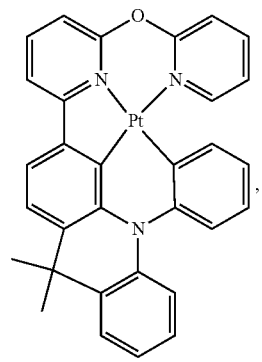
Compound 28
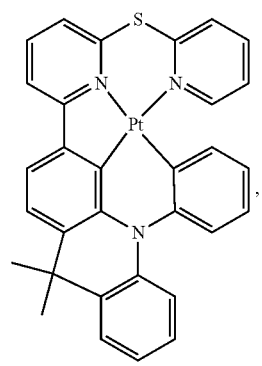
Compound 29
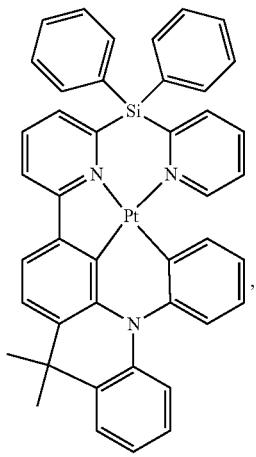
Compound 30
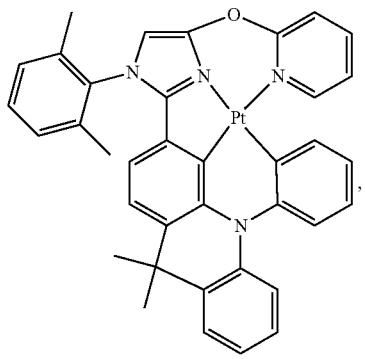
Compound 31
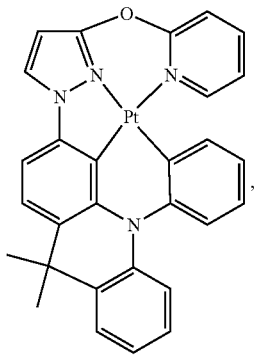
Compound 32
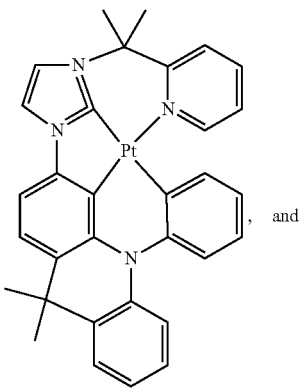
, and -continued Compound 33

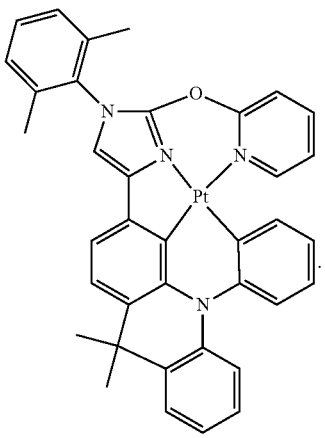

In some embodiments, the metal complex is a compound having Formula (VI)

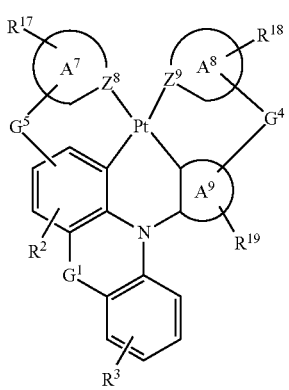

(VI)

wherein rings $A^7$, $A^8$, and $A^9$ are independently five- or six-membered carbocyclic or heterocyclic aromatic rings having 0-3 nitrogen atoms and 0-1 additional heteroatoms selected from the group consisting of oxygen, sulfur, and selenium; wherein $Z^8$ and $Z^9$ are independently carbon or nitrogen; wherein $G^4$ is oxygen, sulfur, $CR^{20}R^{20a}$, $SiR^{20}R^{20a}$, or $NR^{20}$, wherein each $R^{20}$ and $R^{20a}$ is selected independently from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, heteroaryl, acyl, carbonyl, carboxylic acids, ester, nitrile, isonitrille, sulfanyl, sulfinyl, sulfonyl, phosphino, and combinations thereof and wherein $R^{20}$ and $R^{20a}$ may optionally combine with each other or with any one $R^{18}$ or $R^{19}$ to form a ring system, which can be further substituted; wherein $G^5$ is oxygen, sulfur, $CR^{21}R^{21a}$, $SiR^{21}R^{21a}$, or $NR^{21}$ wherein each $R^{21}$ and $R^{21a}$ is selected independently from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof and wherein $R^{21}$ and $R^{21a}$ may optionally combine with each other or with any one $R^2$ or $R^{17}$ to form a ring system, which can be further substituted; wherein $R^{17}$ and $R^{18}$ represent mono-, di-, tri-, or tetra-substitution, wherein each $R^{17}$ or $R^{18}$ is selected independently from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrite, isonitrile, sulfanyl, sulfinyl, sulfonyl, phosphino, and combinations thereof, and wherein any two adjacent $R^{17}$ or any two adjacent $R^{18}$ may optionally combine to form a ring, which can be further substituted; wherein $R^{19}$ represents mono-, di-, or tri-substitution, wherein each $R^{19}$ is selected independently from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrite, isonitrile, sulfanyl, sulfinyl, sulfonyl, phosphino, and combinations thereof, and wherein any two adjacent $R^{19}$ may optionally combine to form a ring, which can be further substituted; wherein any $R^3$ may optionally combine with any $R^{19}$ to form a ring system, which can be further substituted. The other variables have the definitions provided in the above embodiments.

In some other embodiments, the metal complex is a compound selected from the group consisting of:

Compound 34

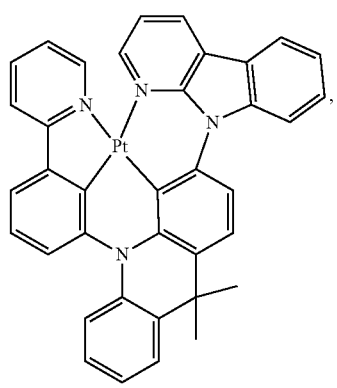

Compound 35

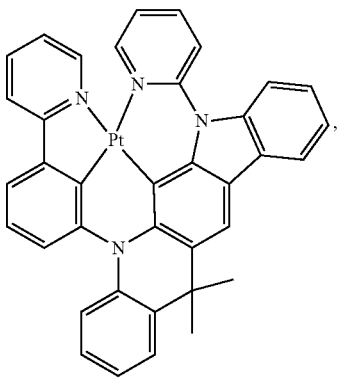

Compound 36

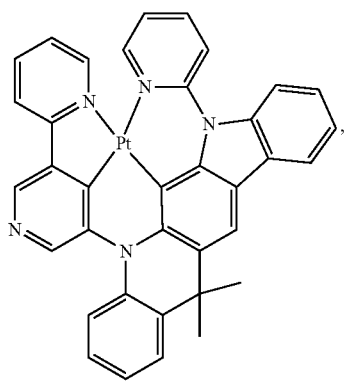

Compound 37

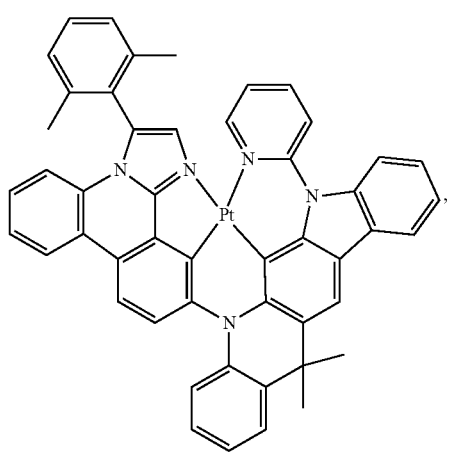

Compound 38

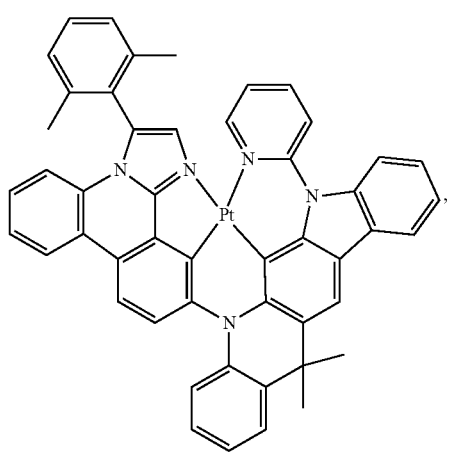

Compound 39

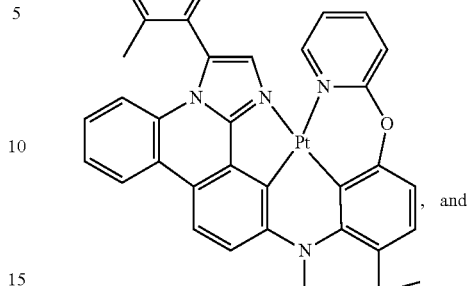

Compound 40

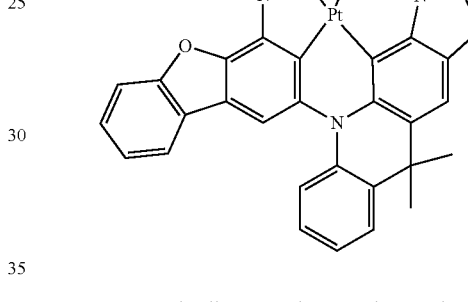

In some embodiments, the metal complex is a compound having Formula (VII):

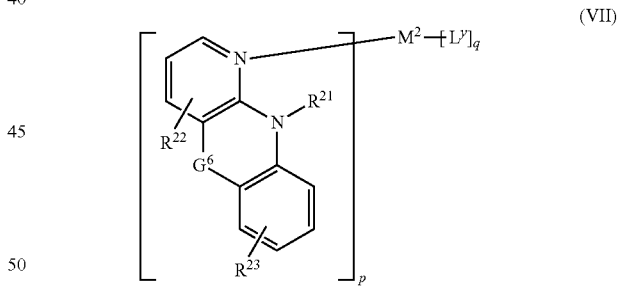

(VII)

wherein each $L^y$ is independently a monodentate ligand, and any two adjacent $L^y$ may optionally combine to form a bidentate ligand; wherein $M^2$ is cobalt(I), rhodium(I), iridium(II), platinum(II), palladium(II), silver(III)gold(III), or copper(III); wherein p is a value from 1 to the maximum number of ligands that may be attached to $M^2$; wherein p+q is the maximum number of ligands that may be attached to $M^2$; wherein $G^6$ is O or $CR^{24}R^{25}$; wherein $R^{21}$ is selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof, wherein $R^{22}$ represents mono-, di-, or tri-substitution, wherein each $R^{22}$ is selected independently from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof, and wherein any two adjacent $R^2$ may optionally combine to form a ring, which can be further substituted; wherein $R^{23}$ represents mono-, di-, tri-, or tetra-substitution, wherein each $R^{23}$ is selected independently from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof, and wherein any two adjacent $R^3$ may optionally combine to form a ring, which can be further substituted; wherein $R^{24}$ and $R^{25}$ are independently selected from the group consisting of hydrogen, deuterium, halide, alkyl, cycloalkyl, heteroalkyl, arylalkyl, alkoxy, atyloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof, and wherein $R^{24}$ and $R^{25}$ may optionally combine to form a ring, which can be further substituted; wherein $R^{21}$ may optionally combine with any $R^{23}$ to form a ring system, which can be further substituted; wherein any of $R^{24}$ or $R^{25}$ may optionally combine with any $R^{22}$ or $R^{23}$ to form a ring system, which can be further substituted; and wherein any of $R^{21}$, $R^{22}$, or $R^{23}$ may optionally combine with one or more L to form a bidentate, tridentate, or tetradentate ligand.

In some embodiments, $M^2$ is platinum(II), palladium(II), or gold(III). In some other embodiments, $M^2$ is platinum (II).

In some embodiments, $G^6$ is O, $C(CH_3)_2$, or $C(C_6H_5)_2$.

In some other embodiments, the metal complex is a compound selected from the group consisting of:

Compound 41

Compound 42

-continued

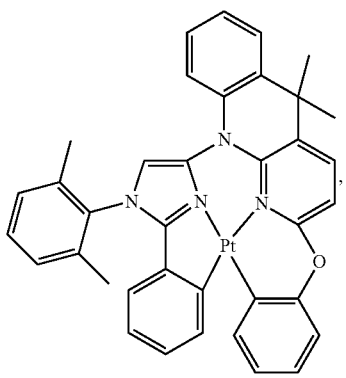

Compound 43

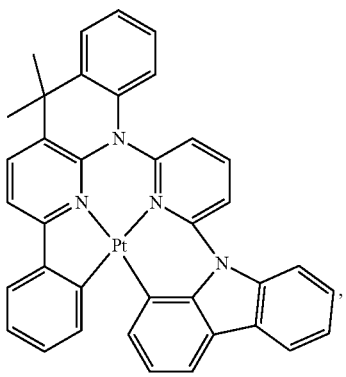

Compound 44

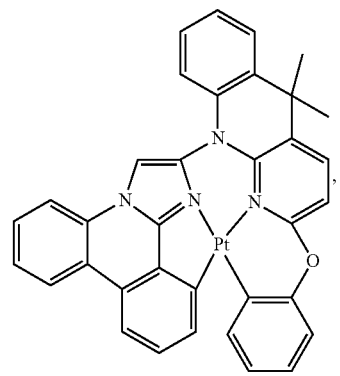

Compound 45

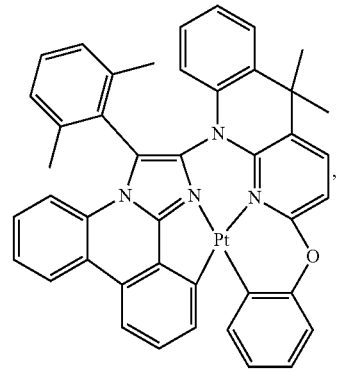

Compound 46

-continued
Compound 47
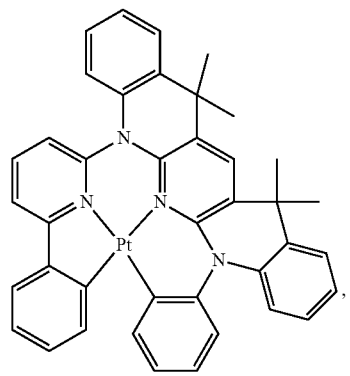
Compound 48
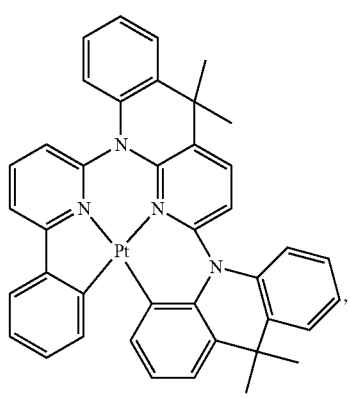
Compound 49
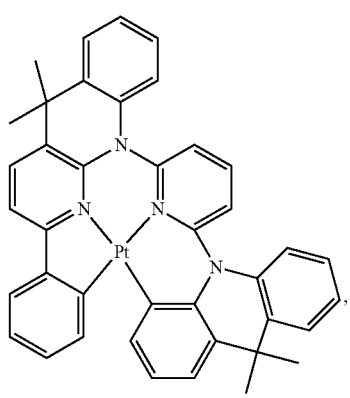
Compound 50
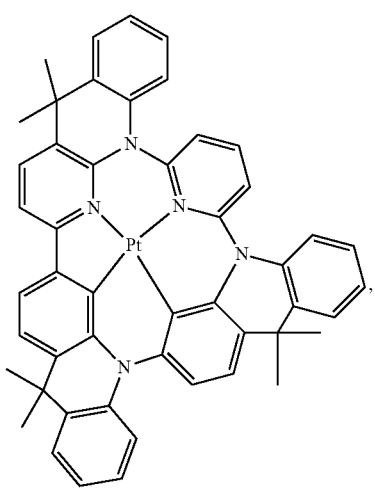
-continued
Compound 51
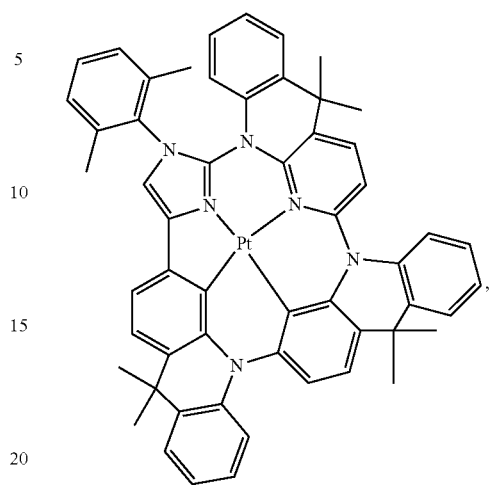
Compound 52
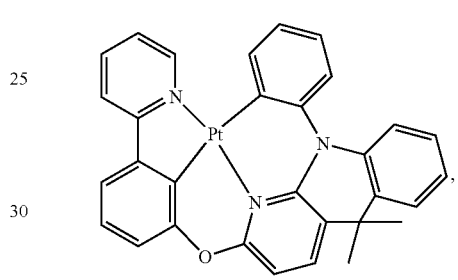
Compound 53
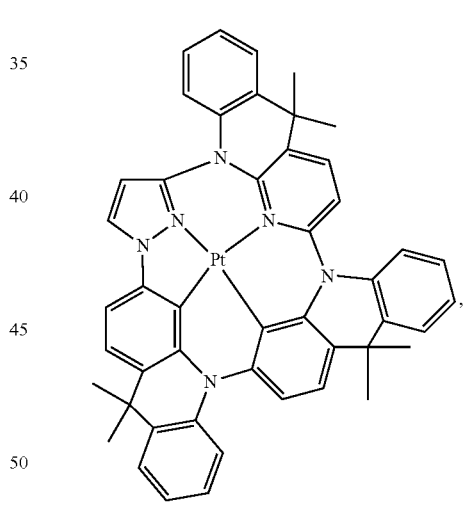
Compound 54
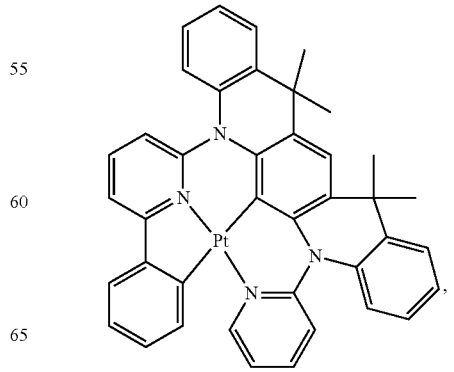

-continued

Compound 55

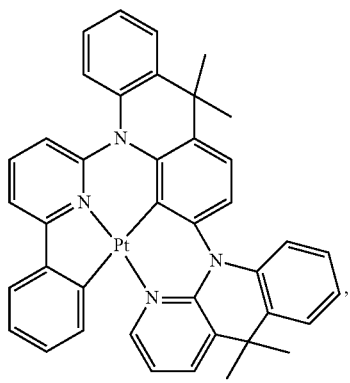

Compound 56

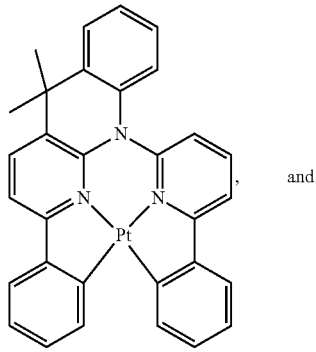
and

Compound 57

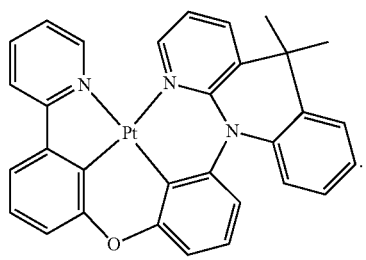

In another aspect, the invention provides devices that include metal complexes having a bridged N,N-diaryl ligand, such as those described in the foregoing paragraphs. In some embodiments, the invention provides a first device comprising a first organic light emitting device, which further comprises: an anode; a cathode; and an organic layer disposed between the anode and the cathode, which comprises a boron-nitrogen heterocycle according to any of the above embodiments. In some embodiments, the first device is a consumer product. In some embodiments, the first device is an organic light emitting device (OLED). In some embodiments, the first device comprises a lighting panel.

In some embodiments, the organic layer of the first device is an emissive layer. In some such embodiments, the emissive layer comprises an emissive dopant. In some embodiments, a metal complex having a bridged N,N-diaryl ligand (as described above) is an emissive dopant. In some other embodiments, a metal complex having a bridged N,N-diaryl ligand (as described above) is a non-emissive dopant.

In some embodiments, the organic layer of the first device comprises a host. In some such embodiments, the host comprises a triphenyiene containing benzo-fused thiophene or benzo-fused furan; wherein any substituent in the host is an unfused substituent independently selected from the group consisting of $C_nH_{2n+1}$, $OC_nH_{2n+1}$, $OAr_1$, $N(C_nH_{2n+1})_2$, $N(Ar_1)(Ar_2)$, $CH=CH-C_nH_{2n+1}$, $C\equiv C-C_nH_{2n+1}$, $Ar_1$, $Ar_1$-$Ar_2$, and $C_nH_{2n}-Ar_1$, or the host has no substitutions, wherein n is from 1 to 10; and wherein $Ar_1$ and $Ar_2$ are independently selected from the group consisting of benzene, biphenyl, naphthalene, triphenylene, carbazole, and heteroaromatic analogs thereof. In some other embodiments, the host comprises a compound selected from the group consisting of: carbazole, dibenzothiphene, dibenzofuran, dibenzoselenophene, azacarbazole, aza-dibenzothiophene, aza-dibenzofuran, and aza-dibenzoselenophene.

In some embodiments, the host is a compound selected from the group consisting of:

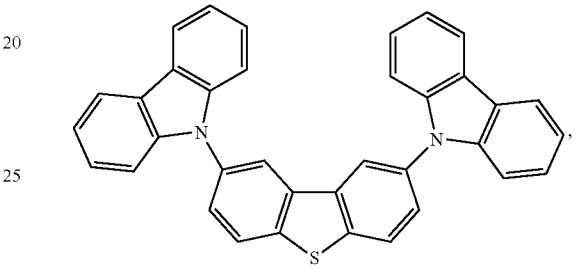

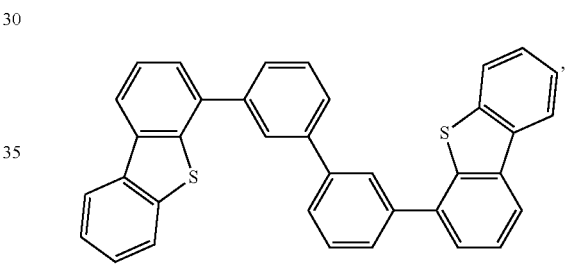

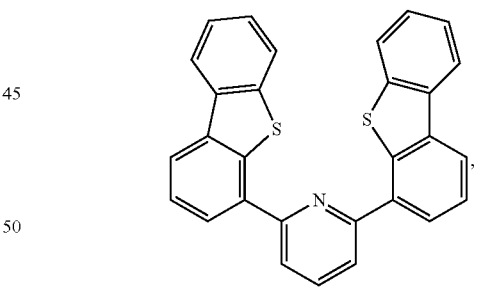

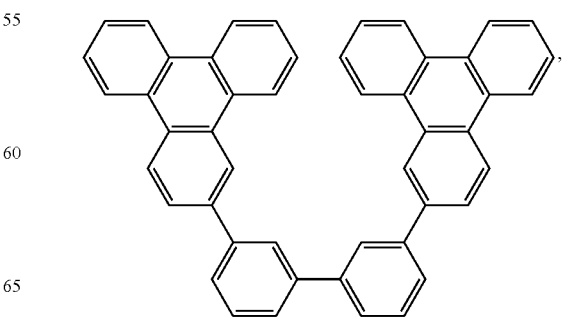

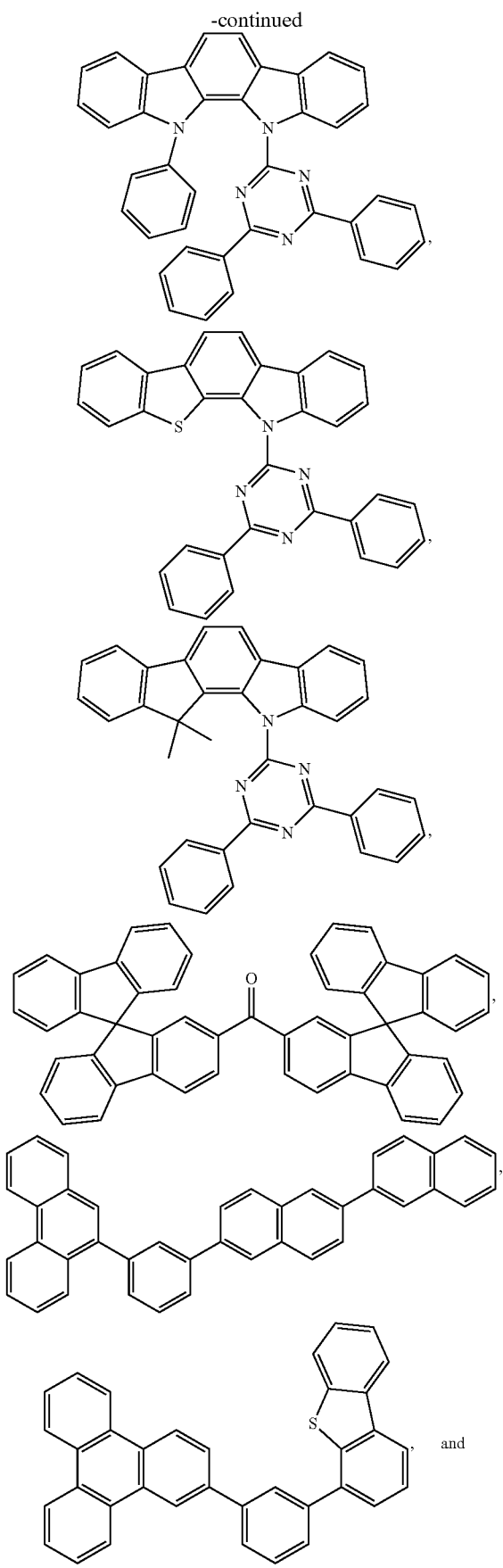

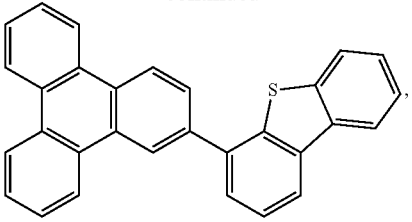

and combinations thereof.

In some embodiments, the host is a metal complex.

DETAILED DESCRIPTION

Generally, an OLED comprises at least one organic layer disposed between and electrically connected to an anode and a cathode. When a current is applied, the anode injects holes and the cathode injects electrons into the organic layer(s). The injected holes and electrons each migrate toward the oppositely charged electrode. When an electron and hole localize on the same molecule, an "exciton," which is a localized electron-hole pair having an excited energy state, is formed. Light is emitted when the exciton relaxes via a photoemissive mechanism. In some cases, the exciton may be localized on an excimer or an exciplex. Non-radiative mechanisms, such as thermal relaxation, may also occur, but are generally considered undesirable.

The initial OLEDs used emissive molecules that emitted light from their singlet states ("fluorescence") as disclosed, for example, in U.S. Pat. No. 4,769,292, which is incorporated by reference in its entirety. Fluorescent emission generally occurs in a time frame of less than 10 nanoseconds.

More recently, OLEDs having emissive materials that emit light from triplet states ("phosphorescence") have been demonstrated. Baldo et al., "Highly Efficient Phosphorescent Emission from Organic Electroluminescent Devices," Nature, vol. 395, 151-154, 1998; "Baldo-I") and Baldo et al., "Very high-efficiency green organic light-emitting devices based on electrophosphorescence," .Appl. Phys, Lett., vol. 75, No, 3, 4-6 (1999) ("Baldo-II"), which are incorporated by reference in their entireties. Phosphorescence is described in more detail in U.S. Pat. No. 7,279,704 at cols. 5-6, which are incorporated by reference.

Figure 1:
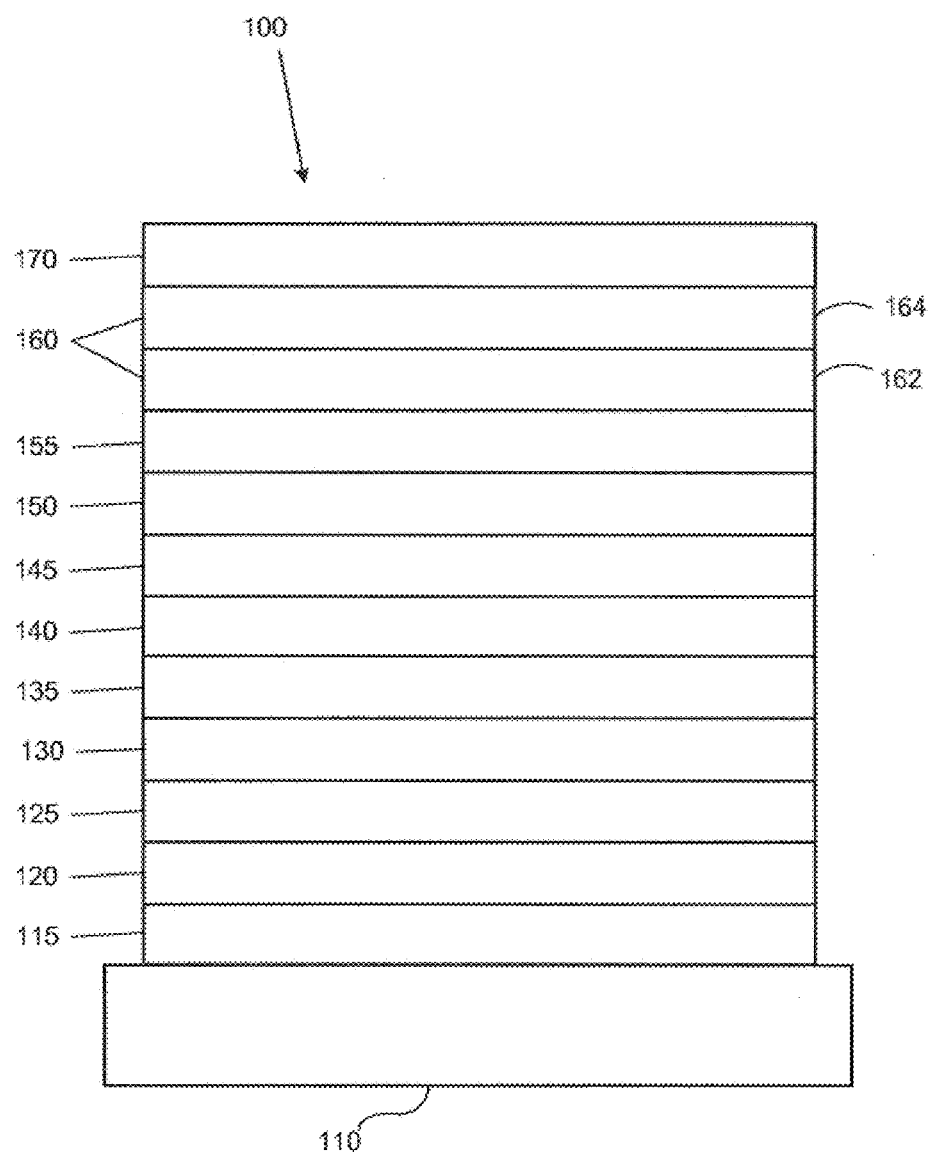
FIG. 1 shows an organic light emitting device.

FIG. 1 shows an organic light emitting device 100. The figures are not necessarily drawn to scale. Device 100 may include a substrate 110, an anode 115, a hole injection layer 120, a hole transport layer 125, an electron blocking layer 130, an emissive layer 135, a hole blocking layer 140, an electron transport layer 145, an electron injection layer 150, a protective layer 155, a cathode 160, and a barrier layer 170. Cathode 160 is a compound cathode having a first conductive layer 162 and a second conductive layer 164. Device 100 may be fabricated by depositing the layers described, in order. The properties and functions of these various layers, as well as example materials, are described in more detail in U.S. Pat No. 7,279,704 at cols. 6-10, which are incorporated by reference.

More examples for each of these layers are available. For example, a flexible and transparent substrate-anode combination is disclosed in U.S. Pat. No. 5,844,363, which is incorporated by reference in its entirety. An example of a p-doped hole transport layer is m-MTDATA doped with $F_4$-TCNQ at a molar ratio of 50:1, as disclosed in U.S. Patent Application Publication No. 2003/0230980, which is incorporated by reference in its entirety. Examples of emissive and host materials are disclosed in U.S. Pat. No. 6,303,238 to Thompson et al., which is incorporated by reference in its entirety. An example of an n-doped electron transport layer is BPhen doped with Li at a molar ratio of 1:1, as disclosed in U.S. Patent Application Publication No. 2003/0230980, which is incorporated by reference in its entirety. U.S. Pat. Nos. 5,703,436 and 5,707,745, which are incorporated by reference in their entireties, disclose examples of cathodes including compound cathodes having a thin layer of metal such as Mg:Ag with an overlying transparent, electrically-conductive, sputter-deposited ITO layer. The theory and use of blocking layers is described in more detail in U.S. Pat. No. 6,097,147 and U.S. Patent Application Publication No. 2003/0230980, which are incorporated by reference in their entireties. Examples of injection layers are provided in U.S. Patent Application Publication No. 2004/0174116, which is incorporated by reference in its entirety. A description of protective layers may be found in U.S. Patent Application Publication No. 2004/0174116, which is incorporated by reference in its entirety.

Figure 2:
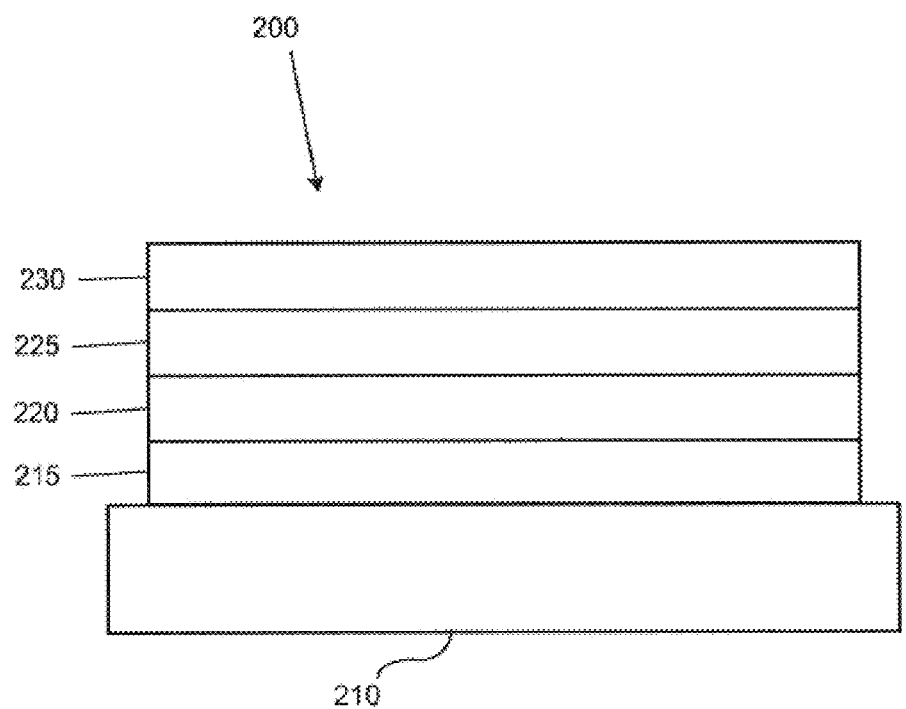
FIG. 2 shows an inverted organic light emitting device that does not have a separate electron transport layer.
Figure 3:
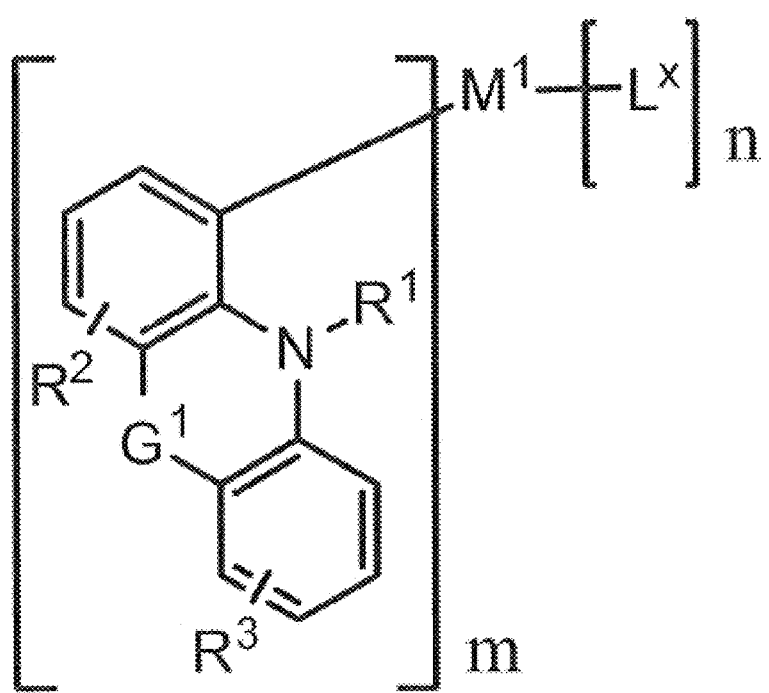
FIG. 3 shows an embodiment of a metal complex having a bridged N,N-diaryl ligand.

FIG. 2 shows an inverted OLED 200. The device includes a substrate 210, a cathode 215, an emissive layer 220, a hole transport layer 225, and an anode 230. Device 200 may be fabricated by depositing the layers described, in order. Because the most common OLED configuration has a cathode disposed over the anode, and device 200 has cathode 215 disposed under anode 230, device 200 may be referred to as an "inverted" OLED. Materials similar to those described with respect to device 100 may be used in the corresponding layers of device 200. FIG. 2 provides one example of how some layers may be omitted from the structure of device 100.

The simple layered structure illustrated in FIGS. 1 and 2 is provided by way of non-limiting example, and it is understood that embodiments of the invention may be used in connection with a wide variety of other structures. The specific materials and structures described are exemplary in nature, and other materials and structures may be used. Functional OLEDs may be achieved by combining the various layers described in different ways, or layers may be omitted entirely, based on design, performance, and cost factors. Other layers not specifically described may also be included. Materials other than those specifically described may be used. Although many of the examples provided herein describe various layers as comprising a single material, it is understood that combinations of materials, such as a mixture of host and dopant, or more generally a mixture, may be used. Also, the layers may have various sublayers. The names given to the various layers herein are not intended to be strictly limiting. For example, in device 200, hole transport layer 225 transports holes and injects holes into emissive layer 220, and may be described as a hole transport layer or a hole injection layer. In one embodiment, an OLED may be described as having an "organic layer" disposed between a cathode and an anode. This organic layer may comprise a single layer, or may further comprise multiple layers of different organic materials as described, for example, with respect to FIGS. 1 and 2.

Structures and materials not specifically described may also be used, such as OLEDs comprised of polymeric materials (PLEDs) such as disclosed in U.S. Pat. No. 5,247, 190 to Friend et al., which is incorporated by reference in its entirety. By way of further example, OLEDs having a single organic layer may be used. OLEDs may be stacked, for example as described in U.S. Pat. No. 5,707,745 to Forrest et al, which is incorporated by reference in its entirety. The OLED structure may deviate from the simple layered structure illustrated in FIGS. 1 and 2. For example, the substrate may include an angled reflective surface to improve outcoupling, such as a mesa structure as described in U.S. Pat. No. 6,091,195 to Forrest et al., and/or a pit structure as described in U.S. Pat, No. 5,834,893 to Bulovic et al., which are incorporated by reference in their entireties.

Unless otherwise specified, any of the layers of the various embodiments may be deposited by any suitable method. For the organic layers, preferred methods include thermal evaporation, ink-jet, such as described in U.S. Pat. Nos. 6,013,982 and 6,087,196, which are incorporated by reference in their entireties, organic vapor phase deposition (OVPD), such as described in U.S. Pat. No. 6,337,102 to Forrest et al., which is incorporated by reference in its entirety, and deposition by organic vapor jet printing (OVJP), such as described in U.S. patent No. 7,431,968, issued on Oct. 7, 2008, which is incorporated by reference in its entirety. Other suitable deposition methods include spin coating and other solution based processes. Solution based processes are preferably carried out in nitrogen or an inert atmosphere. For the other layers, preferred methods include thermal evaporation. Preferred patterning methods include deposition through a mask, cold welding such as described in U.S. Pat. Nos. 6,294,398 and 6,468,819, which are incorporated by reference in their entireties, and patterning associated with some of the deposition methods such as ink-jet and OVJD. Other methods may also be used. The materials to be deposited may be modified to make them compatible with a particular deposition method. For example, substituents such as alkyl and aryl groups, branched or unbranched, and preferably containing at least 3 carbons, may be used in small molecules to enhance their ability to undergo solution processing. Substituents having 20 carbons or more may be used, and 3-20 carbons is a preferred range. Materials with asymmetric structures may have better solution processibility than those having symmetric structures, because asymmetric materials may have a lower tendency to recrystallize. Dendrimer substituents may be used to enhance the ability of small molecules to undergo solution processing.

Devices fabricated in accordance with embodiments of the present invention may further optionally comprise a barrier layer. One purpose of the barrier layer is to protect the electrodes and organic layers from damaging exposure to harmful species in the environment including moisture, vapor and/or gases, etc. The barrier layer may be deposited over, under or next to a substrate, an electrode, or over any other parts of a device including an edge. The barrier layer may comprise a single layer, or multiple layers. The barrier layer may be formed by various known chemical vapor deposition techniques and may include compositions having a single phase as well as compositions having multiple phases. Any suitable material or combination of materials may be used for the barrier layer. The barrier layer may incorporate an inorganic or an organic compound or both. The preferred barrier layer comprises a mixture of a polymeric material and anon-polymeric material as described in U.S. Pat. No. 7,968,146, PCT Pat. Application Nos. PCT/US2007/023098 and PCT/US2009/04 829, which are herein incorporated by reference in their entireties. To be considered a "mixture", the aforesaid polymeric and non-polymeric materials comprising the barrier layer should be deposited under the same reaction conditions and/or at the same time. The weight ratio of polymeric to non-polymeric material may be in the range of 95:5 to 5:95. The polymeric material and the non-polymeric material may be created from the same precursor material. In one example, the mixture of a polymeric material and a non-polymeric material consists essentially of polymeric silicon and inorganic silicon.

Devices fabricated in accordance with embodiments of the invention may be incorporated into a wide variety of consumer products, including flat panel displays, computer monitors, medical monitors, televisions, billboards, lights for interior or exterior illumination and/or signaling, heads up displays, fully transparent displays, flexible displays, laser printers, telephones, cell phones, personal digital assistants (PDAs), laptop computers, digital cameras, camcorders, viewfinders, micro-displays, vehicles, a large area wall, theater or stadium screen, or a sign. Various control mechanisms may be used to control devices fabricated in accordance with the present invention, including passive matrix and active matrix. Many of the devices are intended for use in a temperature range comfortable to humans, such as 18 degrees C. to 30 degrees C., and more preferably at room temperature (20-25 degrees C.).

The materials and structures described herein may have applications in devices other than OLEDs. For example, other optoelectronic devices such as organic solar cells and organic photodetectors may employ the materials and structures. More generally, organic devices, such as organic transistors, may employ the materials and structures.

The terms halo, halogen, alkyl, cycloalkyl, alkenyl, alkynyl, arylkyl, heterocyclic group, aryl, aromatic group, and heteroaryl are known to the art, and are defined in U.S. Pat. No. 7,279,704 at cols. 31-32, which are incorporated herein by reference.

Metal complexes having ligands with N,N-diaryl groups can function as emissive agents, e.g., phosphorescent emitters. In some instances, however, such structures may exhibit instability due to rupture of the N-aryl bond, thereby limiting the utility of such compounds as emissive agents. In some embodiments of the invention, a bridging group is incorporated into the N,N-diaryl ligand structure to stabilize the ligand and strengthen the N-aryl bond. The disclosed bridging structures can also improve the steric properties of the ligand and make it more suitable for certain types of coordination, such as tetradentate coordination in a square planar configuration (e.g., with platinum (II)).

In at least one aspect, the invention provides metal complexes having an N,N-diaryl ligand, such as compounds having Formula (I):

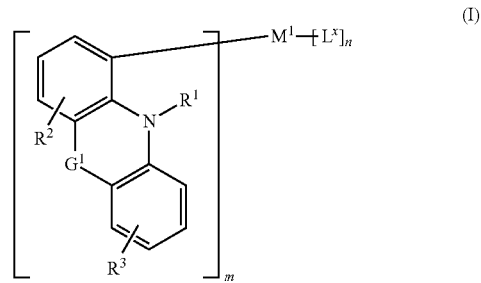

wherein each $L^x$ is independently a monodentate ligand, and any two adjacent $L^x$ may optionally combine to form a bidentate ligand; wherein $M^1$ is cobalt(I), rhodium(I), iridium(I), nickel(II), platinum(II), palladium(II), silver(III), gold(III), or copper(III); wherein m is a value from 1 to the maximum number of ligands that may be attached to $M^1$; wherein m+n is the maximum number of ligands that may be attached to $M^1$; wherein $G^1$ is O or $CR^4R^5$, wherein $R^1$ is selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof; wherein $R^2$ represents mono-, di-, or tri-substitution, wherein each $R^2$ is selected independently from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, sulfanyl, sulfinyl, sulfonyl, phosphino, and combinations thereof, and wherein any two adjacent $R^2$ may optionally combine to form a ring, which can be further substituted; wherein $R^3$ represents mono-, di-, tri-, or tetra-substitution, wherein each $R^3$ is selected independently from the group consisting of hydrogen, deuterium, halide, alkyl, cycloalkyl, heteroalkyl, arylalkyl, alkoxy, aryloxy amino, silyl, alkenyl, cycloalkenyl, heteroalkenyl, alkynyl, aryl, heteroaryl, acyl, carbonyl, carboxylic acids, ester, nitrite, isonitrile, sulfanyl, sulfinyl, sulfonyl, phosphino, and combinations thereof, and wherein any two adjacent $R^3$ may optionally combine to form a ring, which can be further substituted; wherein $R^4$ and $R^5$ are independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof, and wherein $R^4$ and $R^5$ may optionally combine to form a ring, which can be further substituted; wherein $R^1$ may optionally combine with any $R^3$ to form a ring system, which can be further substituted; wherein any of $R^4$ or $R^5$ may optionally combine with any $R^2$ or $R^3$ to form a ring system, which can be further substituted; and wherein any of R¹, R², or R³ may optionally combine with one or more to form a bidenlate, tridentate, or tetradentate ligand.

In some embodiments, M¹ is platinum(II), palladium(II), or gold(III). In some other embodiments, M¹ is platinum (II).

In some embodiments, G¹ is O, C(CH₃)₂, or C(C₆H₅)₂.

In some embodiments, the metal complex is a compound having Formula (II):

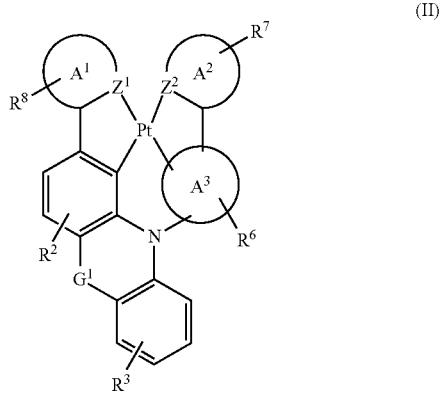

(II)

wherein rings A¹, A², and A³ are independently five- or six-membered carbocyclic or heterocyclic aromatic rings having 0-3 nitrogen atoms and 0-1 additional heteroatoms selected from the group consisting of oxygen, sulfur, and selenium; Z¹ and Z² are independently carbon or nitrogen; wherein R² represents mono- or di-substitution, wherein each R² is selected independently from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfonyl, phosphino, and combinations thereof, and wherein any two adjacent R² may optionally combine to form a ring, which can be further substituted; wherein R³ represents mono-, di-, ti-, or tetra-substitution, wherein each R³ is selected independently from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof, and wherein any two adjacent R³ may optionally combine to form a ring, which can be further substituted; wherein R⁶ represents mono-, di-, or tri-substitution, wherein each R⁶ is selected independently from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof, and wherein any two adjacent R⁶ may optionally combine to form a ring, which can be further substituted; wherein R⁷ and R⁸ represent mono-, di-, tri-, or tetra-substitution, wherein each R⁷ or R⁸ is selected independently from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof, and wherein any two adjacent R⁷ or any two adjacent R⁸ may optionally combine to form a ring, which can be further substituted; wherein any R³ may optionally combine with any R⁶ to form a ring system, which can be further substituted; wherein any R² may optionally combine with any R⁸ to form a ring system, which can be further substituted; and wherein any R⁶ may optionally combine with any R⁷ to form a ring system, which can be further substituted; wherein any R⁷ may optionally combine with any R⁸ to form a ring system, which can be further substituted. The other variables have the definitions provided in the above embodiments.

In some such embodiments, the metal complex is a compound having Formula (IIa):

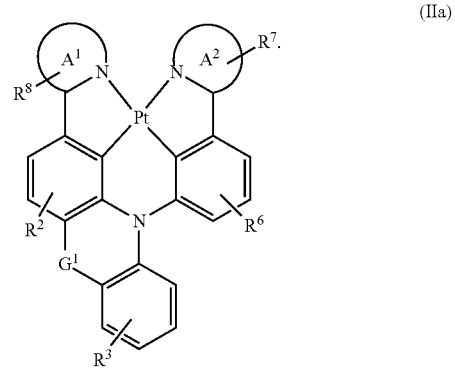

(IIa)

In some other such embodiments, the metal complex is a compound selected from the group consisting of:

Compound 1

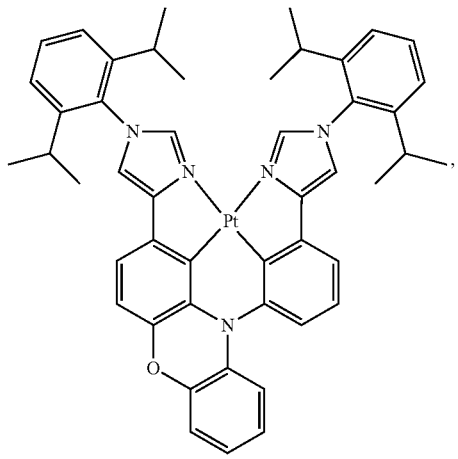

Compound 2
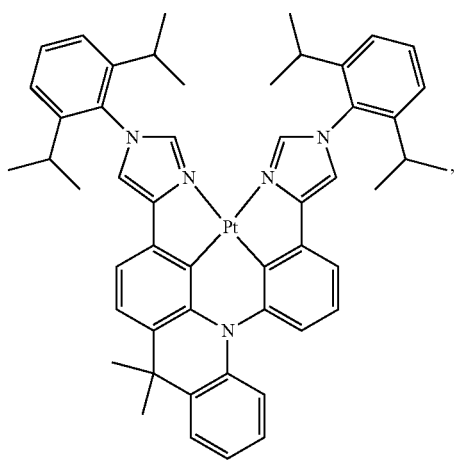
Compound 3
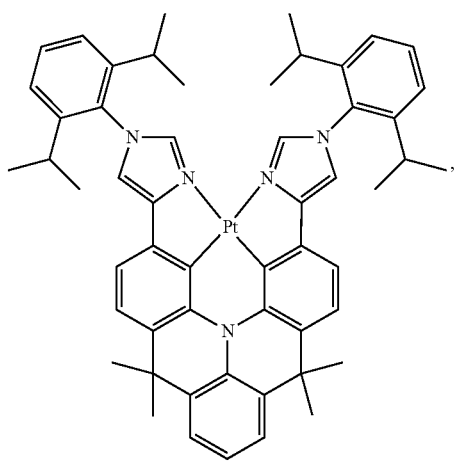
Compound 4
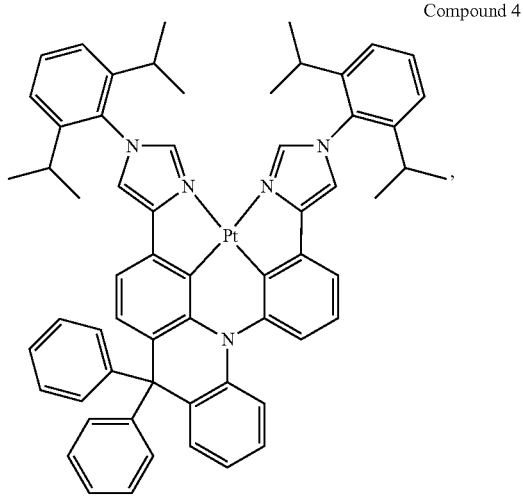
Compound 5
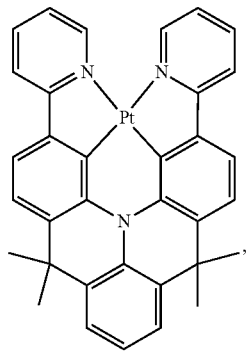
Compound 6
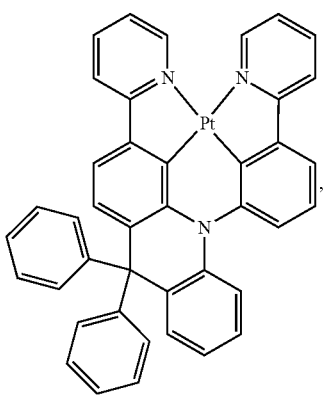
Compound 7
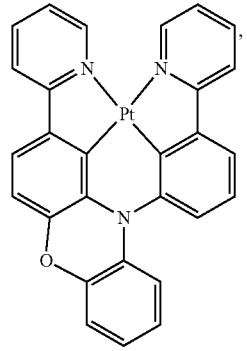
Compound 8
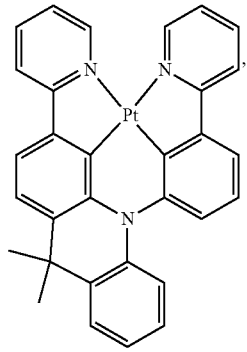

Compound 9

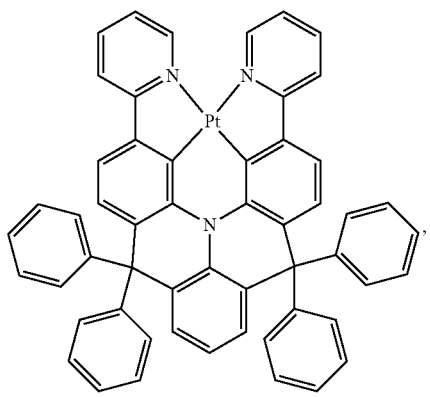

Compound 10

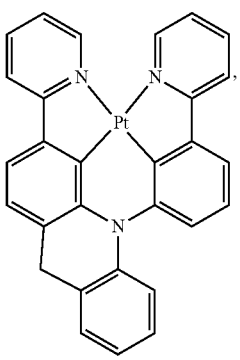

Compound 11

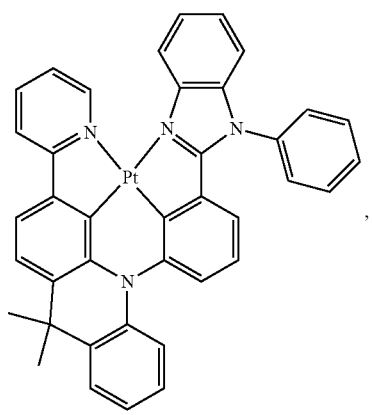

and

Compound 12

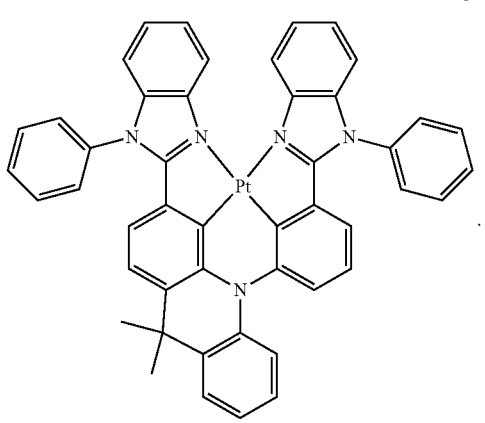

In some embodiments, the metal complex is a compound having Formula (IV)

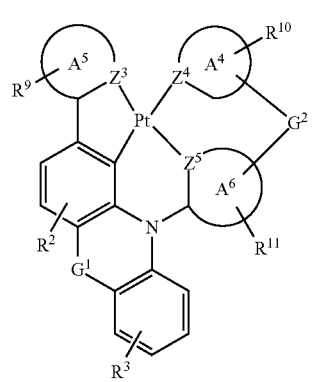

(IV)

wherein rings $A^4$, $A^5$, and $A^6$ are independently five- or six-membered carbocyclic or heterocyclic aromatic rings having 0-3 nitrogen atoms and 0-1 additional heteroatoms selected from the group consisting of oxygen, sulfur, and selenium; wherein $Z^3$, $Z^4$, and $Z^5$ are independently carbon or nitrogen; wherein $G^2$ is oxygen, sulfur, $CR^{12}R^{12a}$, $SiR^{12}R^{12a}$, or $NR^{12}$, wherein each $R^{12}$ and $R^{12a}$ is selected independently from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroatyl, carbonyl, carboxylic acids, ester, nitrile, sulfanyl, sulfinyl, sulfonyl, phosphino, and combinations thereof and wherein $R^{12}$ and $R^{12a}$ may optionally combine with each other or with any one $R^{10}$ or $R^{11}$ to form a ring system, which can be further substituted; wherein $R^9$ and $R^{10}$ represent mono-, di-, tri-, or tetra-substitution, wherein each $R^9$ or $R^{10}$ is selected independently from the group consisting of hydrogen, deuterium, halide, alkyl, cloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof, and wherein any two adjacent $R^9$ or any two adjacent $R^{10}$ may optionally combine to form a ring, which can be further substituted; wherein $R^{11}$ represents mono-, di-, or tri-substitution, wherein each $R^{11}$ is selected independently from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, heteroaryl, acyl, carbonyl, carboxylic acids, ester, nitrile, sulfanyl, sulfinyl, sulfonyl, phosphino, and combinations thereof, and wherein any two adjacent $R^{11}$ may optionally combine to form a ring, which can be further substituted; wherein any $R^3$ may optionally combine/it any $R^{11}$ to form a ring system, which can be further substituted; and wherein any $R^2$ may optionally combine with any $R^9$ to form a ring system, which can be further substituted. The other variables have the definitions provided in the above embodiments.

In some such embodiments, the metal complex is a compound having Formula (IVa):

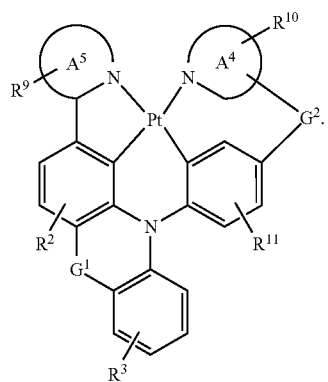
(IVa)
In some embodiments where the metal complex has a Formula (IV) or Formula (IVa) $G^2$ is $NR^{12}$, and $R^{12}$ is phenyl.
In some other embodiments, the metal complex is a compound selected from the group consisting of:
Compound 13
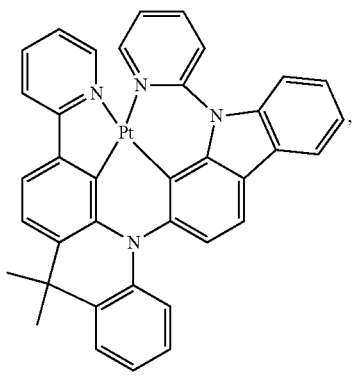
Compound 14
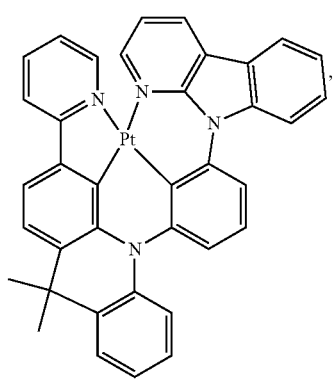
Compound 15
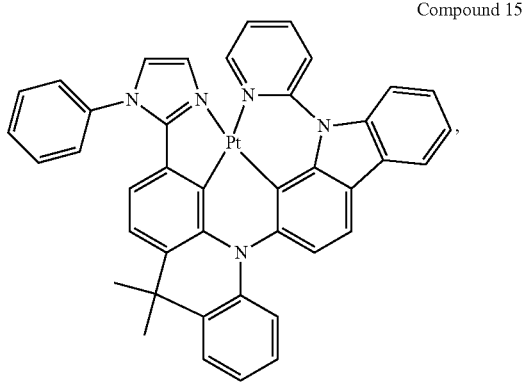
Compound 16
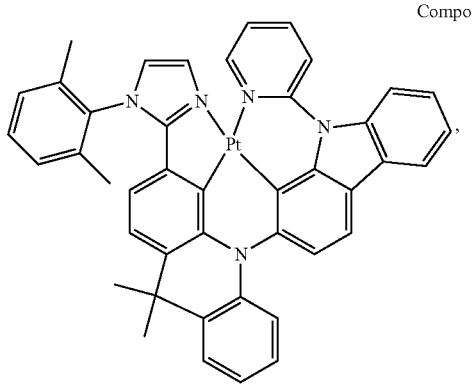
Compound 17
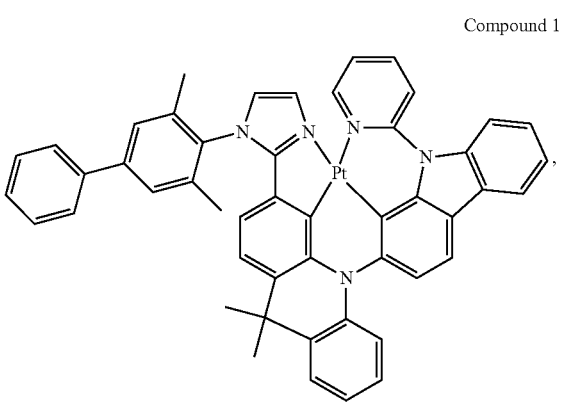
Compound 18
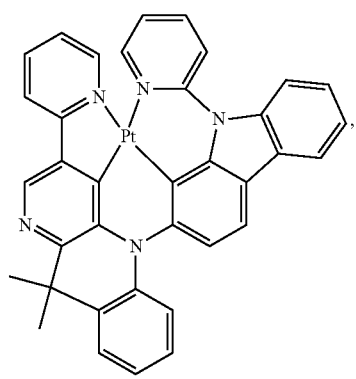

Compound 19
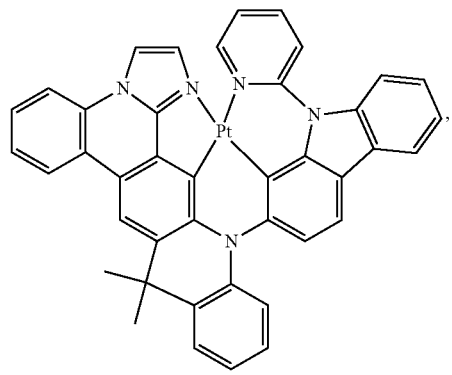
Compound 20
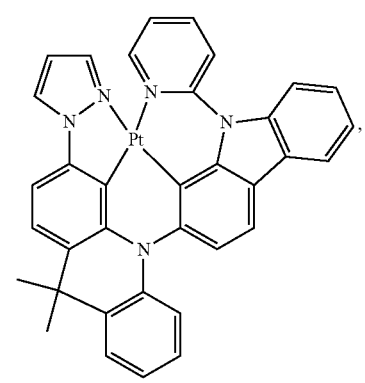
Compound 21
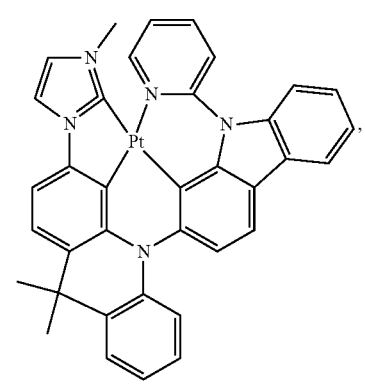
Compound 22
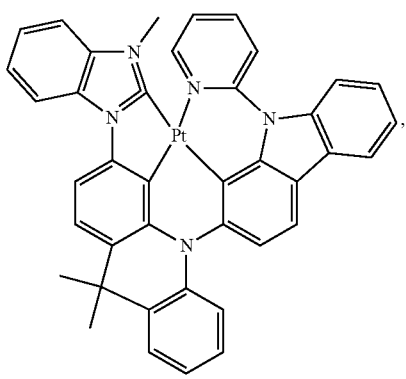
Compound 23
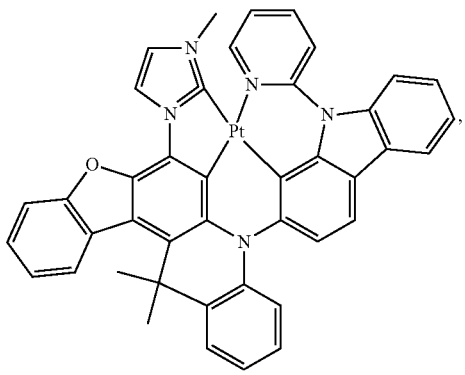
Compound 24
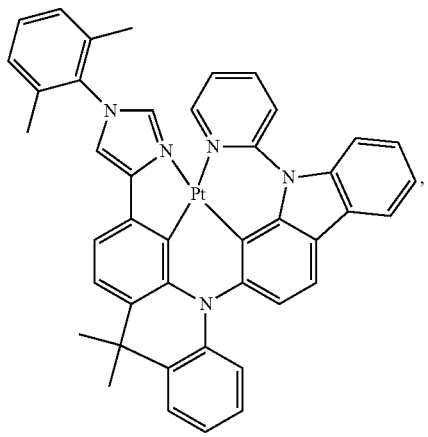
Compound 25
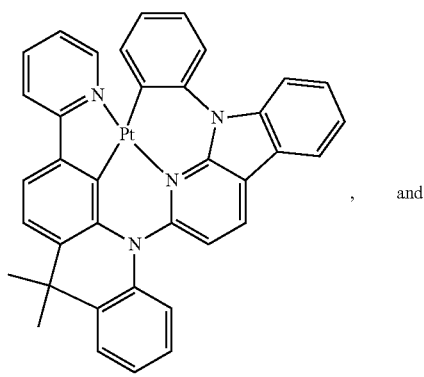
, and
Compound 26
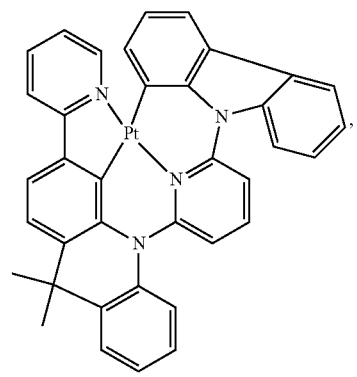
In some embodiments, the metal complex is a compound having Formula (V):

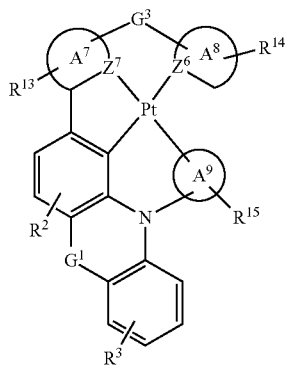

(V)

wherein rings $A^7$, $A^8$, and $A^9$ are independently five- or six-membered carboyclic or heterocyclic aromatic rings having 0-3 nitrogen atoms and 0-1 additional heteroatoms selected from the group consisting of oxygen, sulfur, and selenium; wherein $Z^6$ and $Z^7$ independently are carbon or nitrogen; $G^3$ is oxygen, sulfur, $CR^{16}R^{16a}$, $SiR^{16}R^{16a}$, or $NR^{16}$; wherein each $R^{16}$ and $R^{16a}$ is selected independently from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof, and wherein $R^{16}$ and $R^{16a}$ may optionally combine with each other or with any one $R^{13}$ or $R^{14}$ to form a ring system, which can be further substituted; wherein $R^{13}$ and $R^{14}$ represent mono-, di-, or tri-substitution, wherein each $R^{13}$ or $R^{14}$ is selected independently from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof, and wherein any two adjacent $R^{13}$ or any two adjacent $R^{14}$ may optionally combine to form a ring, which can be further substituted; wherein $R^{15}$ represents mono-, di-, tri- or tetra-substitution, wherein each $R^{15}$ is selected independently from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof, and wherein any two adjacent $R^{15}$ may optionally combine to form a ring, which can be further substituted; wherein any $R^2$ may optionally combine with any $R^{13}$ to form a ring system, which can be further substituted; and wherein any $R^{14}$ may optionally combine with any $R^{15}$ to form a ring system, which can be further substituted. The other variables have the definitions provided in the above embodiments.

In some such embodiments, the metal complex is a compound having Formula (Va):

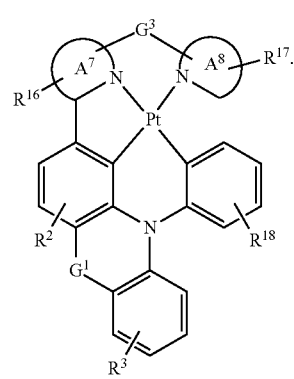

(Va)

In some embodiments where the metal complex has a Formula (V) or Formula (Va), $G^3$ is $NR^{16}$, and $R^{16}$ is phenyl.

In some other embodiments, the metal complex is a compound selected from the group consisting of:

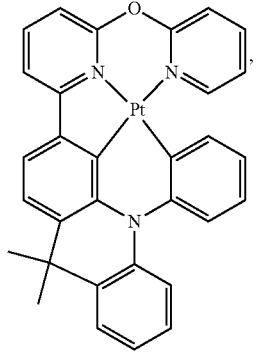

Compound 27

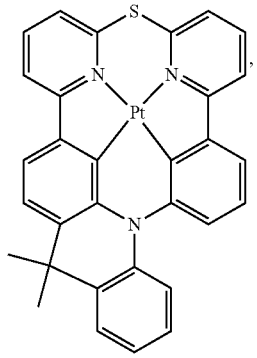

Compound 28

-continued

Compound 29

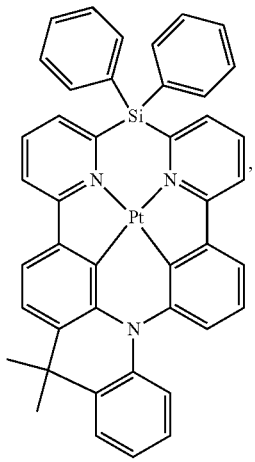

Compound 30

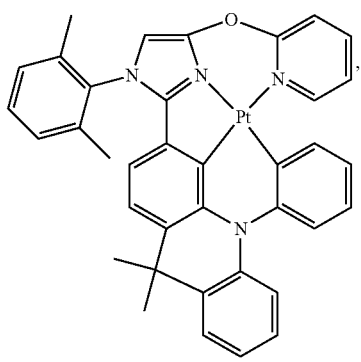

Compound 31

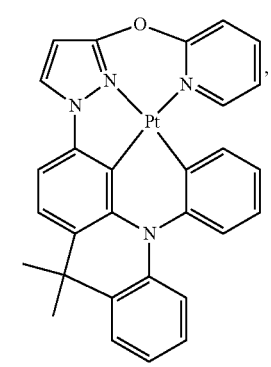

Compound 32

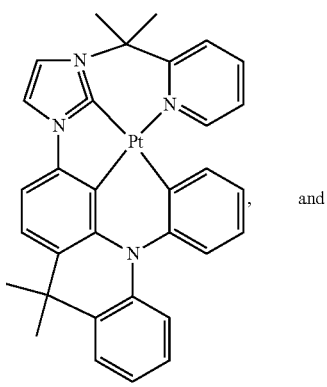

and

-continued

Compound 33

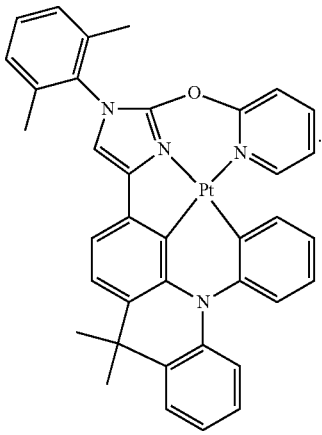

In some embodiments, the metal complex is a compound having Formula (VI):

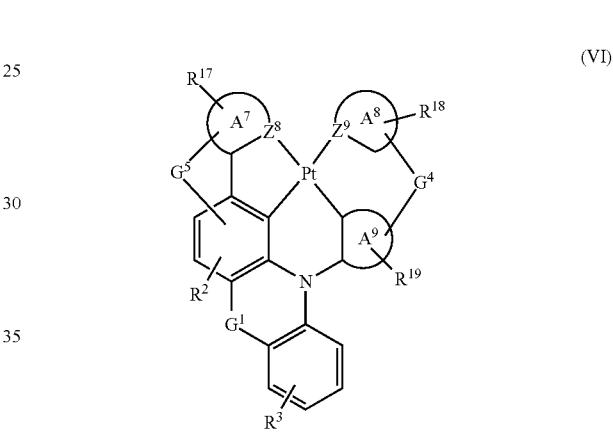

(VI)

wherein rings $A^7$, $Ar^8$, and $A^9$ are independently five- or six-membered carbocyclic or heterocyclic aromatic rings having 0-3 nitrogen atoms and 0-1 additional heteroatoms selected from the group consisting of oxygen, sulfur, and selenium; wherein $Z^8$ and $Z^9$ are independently carbon or nitrogen; wherein $G^4$ is oxygen, sulfur, $CR^{20}R^{20a}$, $SiR^{20}R^{20a}$, or $NR^{20}$, wherein each $R^{20}$ and $R^{20a}$ is selected independently from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, sulfanyl, sulfinyl, sulfonyl, phosphino, and combinations thereof, and wherein $R^{20}$ and $R^{20a}$ may optionally combine with each other or with any one $R^{18}$ or $R^{19}$ to form a ring system, which can be further substituted; wherein $G^5$ is oxygen, sulfur, $CR^{21}R^{21a}$, $SiR^{21}R^{21a}$, or $NR^{21}$, wherein each $R^{21}$ and $R^{21a}$ is selected independently from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl,lfi sunyl, sulfonyl, phosphino, and combinations thereof and wherein $R^{21}$ and $R^{21a}$ may optionally combine with each other or with any one $R^2$ or $R^{17}$ to form a ring system, which can be further substituted; wherein $R^{17}$ and $R^{18}$ represent mono-, di-, tri-, or tetra-substitution, wherein each $R^{17}$ or $R^{18}$ is selected independently from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrite, isonitrile, sulfanyl, sulfinyl, sulfonyl, phosphino, and combinations thereof and wherein any two adjacent $R^{17}$ or any two adjacent $R^{18}$ may optionally combine to form a ring, which can be further substituted; wherein $R^{19}$ represents mono-, di-, or tri-substitution, wherein each $R^{19}$ is selected independently from the group consisting of hydrogen, deuterium, halide, alkyl, cycloalkyl, heteroalkyl, arylalkyl, alkoxy, aryloxy, amino, alkenyl, cycloalkenyl, heteroalkenyl, alkynyl, aryl, heteroaryl, acyl, carbonyl, carboxylic acids, ester, nitrite, isonitrile, sulfanyl, sulfinyl, sulfonyl, phosphino, and combinations thereof, and wherein any two adjacent $R^{19}$ may optionally combine to form a ring, which can be further substituted; wherein any $R^3$ may optionally combine with any $R^{19}$ to form a ring system, which can be further substituted. The other variables have the definitions provided in the above embodiments.

In some other embodiments, the metal complex is a compound selected from the group consisting of:

Compound 34

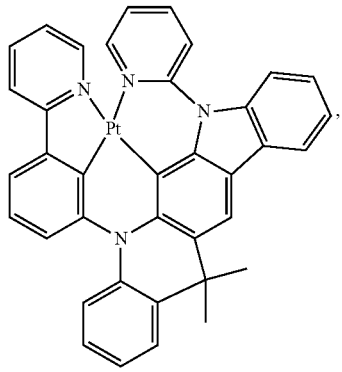

Compound 35

Compound 36

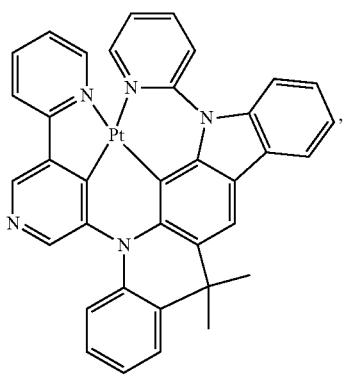

Copound 37

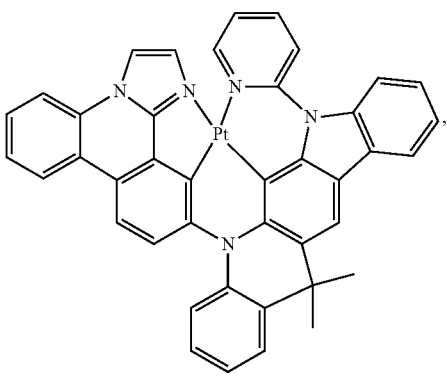

Compound 38

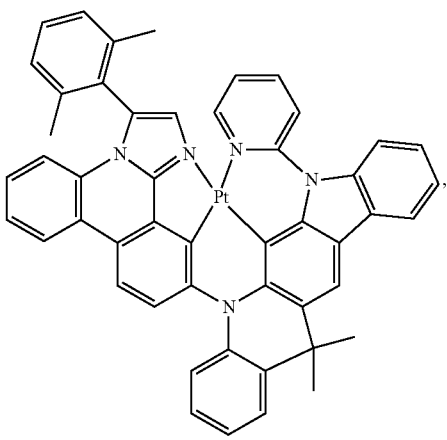

Compound 39

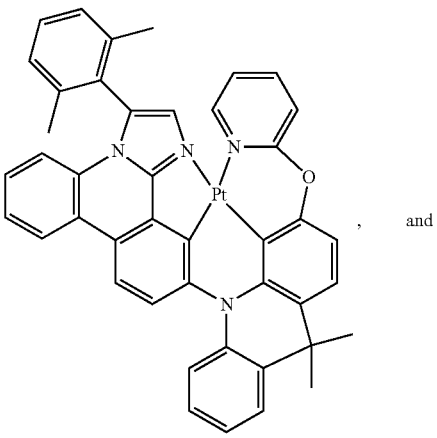

, and

Compound 40

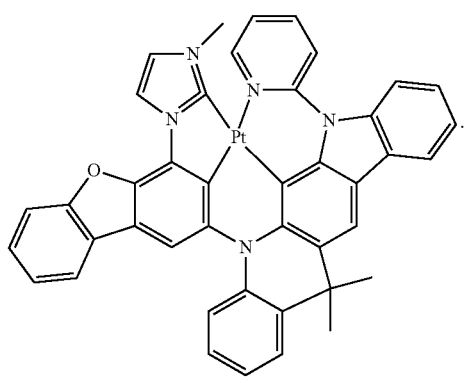

In some embodiments, the metal complex is a compound having Formula (VII):

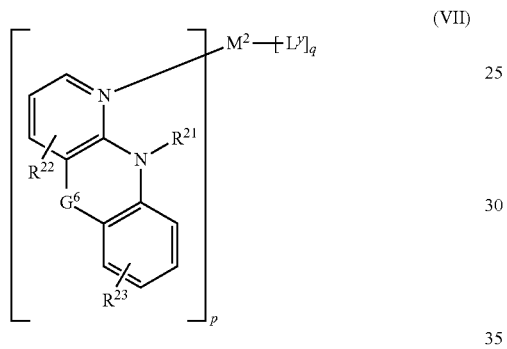

(VII)

wherein each $L^y$ is independently a monodentate ligand, and any two adjacent $L^y$ may optionally combine to form a bidentate ligand; wherein $M^2$ is cobalt(I), rhodium(I), iridium(I), nickel(II), platinum(II), palladium(II), silver(III), gold(III), or copper(III); wherein p is a value from 1 to the maximum number of ligands that may be attached to $M^2$; wherein p+q is the maximum number of ligands that may be attached to $M^2$; wherein $G^6$ is O or $CR^{24}R^{25}$; wherein $R^{21}$ is selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof; wherein $R^{22}$ represents mono-, di-, or tri-substitution, wherein each $R^{22}$ is selected independently from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof, and wherein any two adjacent $R^2$ may optionally combine to form a ring, which can be further substituted; wherein $R^{23}$ represents mono-, di-, tri-, or tetra-substitution, wherein each $R^{23}$ is selected independently from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof, and wherein any two adjacent $R^3$ may optionally combine to form a ring, which can be further substituted; wherein $R^{24}$ and $R^{25}$ are independently selected from the group consisting of hydrogen, deuterium, halide, alkyl, cycloalkyl, heteroalkyl, arylalkyl, alkoxy, atyloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof, and wherein $R^{24}$ and $R^{25}$ may optionally combine to form a ring, which can be further substituted; wherein $R^{21}$ may optionally combine with any $R^{23}$ to form a ring system, which can be further substituted; wherein any of $R^{24}$ or $R^{25}$ may optionally combine with any $R^{22}$ or $R^{23}$ to form a ring system, which can be further substituted; and wherein any of $R^{21}$, $R^{22}$, or $R^{23}$ may optionally combine with one or more $L^y$ to form a bidentate, tridentate, or tetradentate ligand.

In some embodiments, $M^2$ is platinum(II), palladium(II), or gold(III). In some other embodiments, $M^2$ is platinum (II).

In some embodiments, $G^6$ is O, $C(CH_3)_2$, or $C(C_6H_5)_2$.

In some other embodiments, the metal complex is a compound selected from the group consisting of:

Compound 41

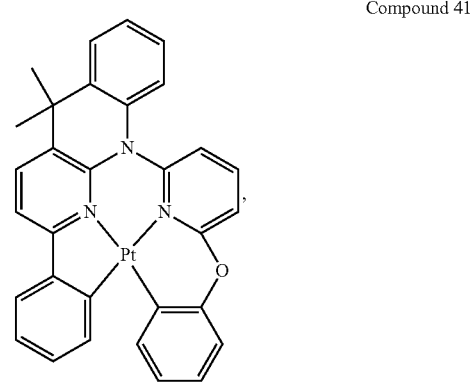

Compound 42

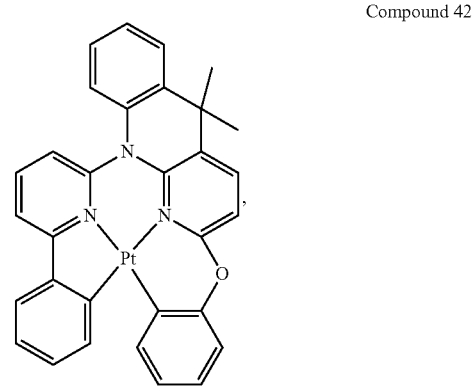

Compound 43

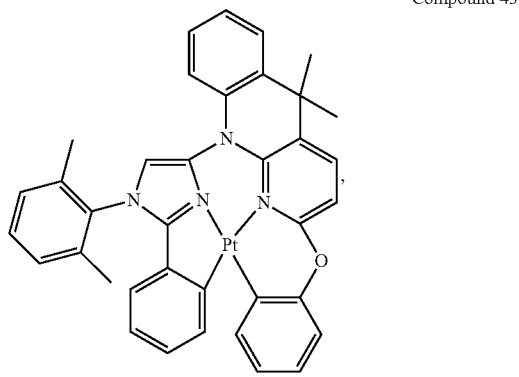

Compound 44
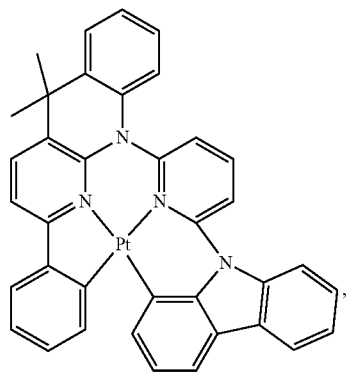
Compound 48
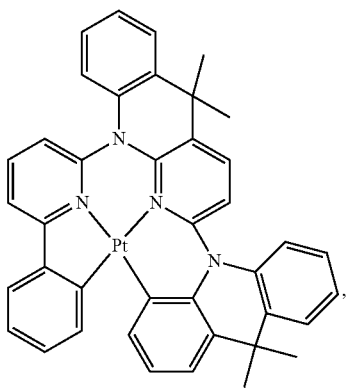
Compound 45
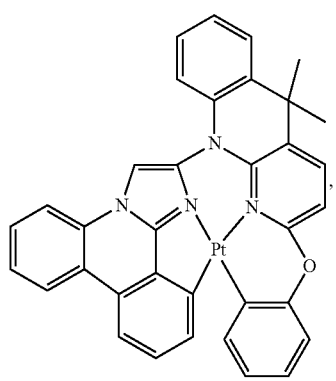
Compound 49
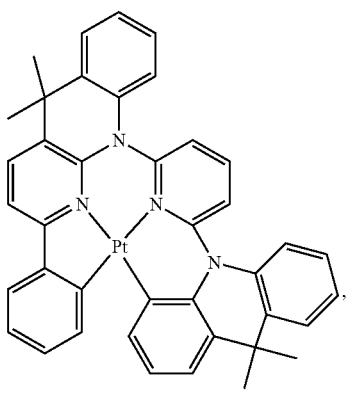
Compound 46
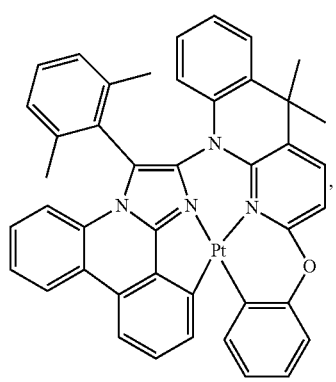
Compound 47
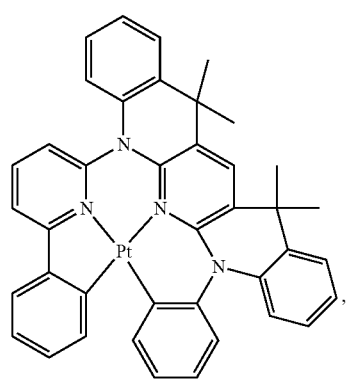
Compound 50
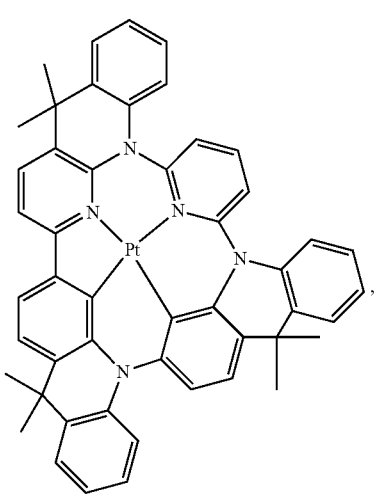

Compound 51

Compound 52

Compound 53

Compound 54

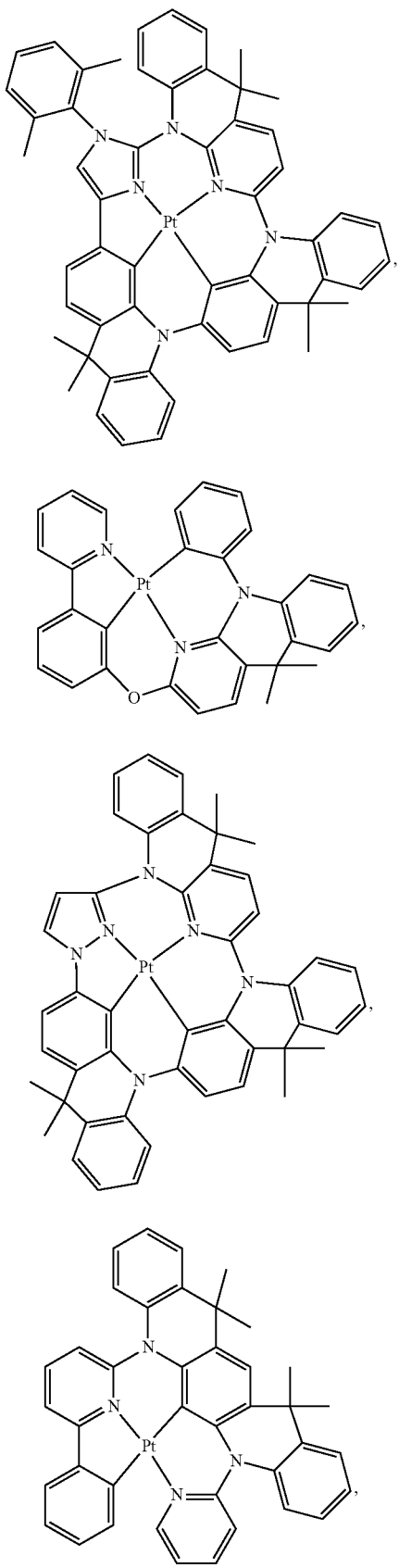

Compound 55

Compound 56

Compound 57

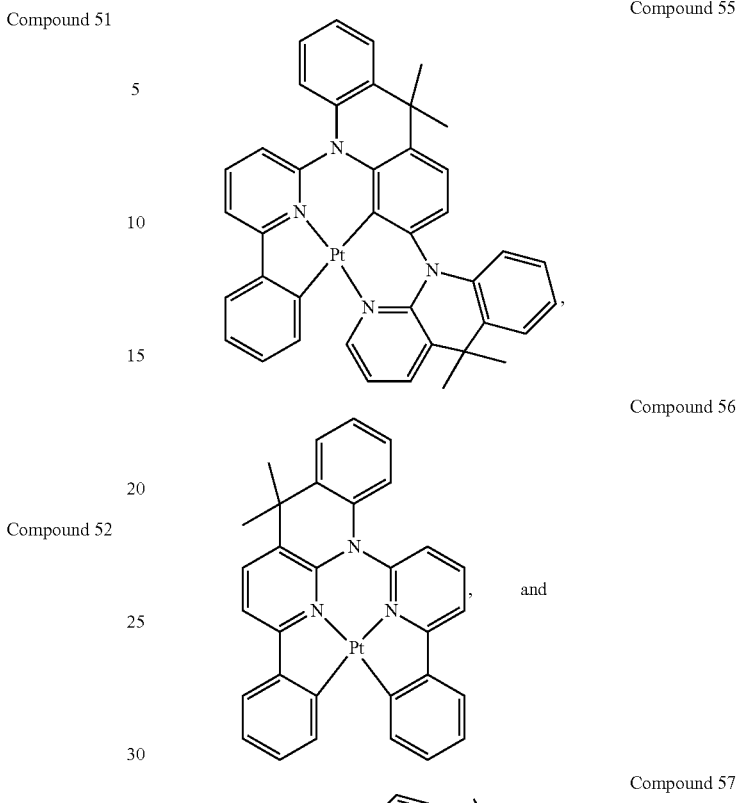

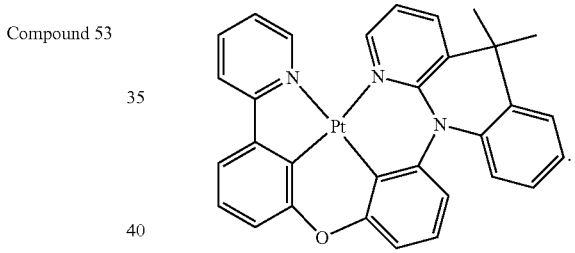

In another aspect, the invention provides devices that include metal complexes having a bridged N,N-diaryl ligand, such as those described in the foregoing paragraphs. In some embodiments, the invention provides a first device comprising a first organic light emitting device, which further comprises: an anode; a cathode; and an organic layer disposed between the anode and the cathode, which comprises a boron-nitrogen heterocycle according to any of the above embodiments. In some embodiments, the first device is a consumer product. In some embodiments, the first device is an organic light emitting device (OLED). In some embodiments, the first device comprises a lighting panel.

In some embodiments, the organic layer of the first device is an emissive layer. In some such embodiments, the emissive layer comprises an emissive dopant. In some embodiments, a metal complex having a bridged N,N-diaryl ligand (as described above) is an emissive dopant. In some other embodiments, a metal complex having a bridged N,N-diaryl ligand (as described above) is a non-emissive dopant.

In some embodiments, the organic layer of the first device comprises a host. In some such embodiments, the host comprises a triphenylene containing benzo-fused thiophene or benzo-fused furan; wherein any substituent in the host is an unfused substituent independently selected from the group consisting of $C_nH_{2n+1}$, $OC_nH_{2n+1}$, $OAr_1$, N(C$_n$H$_{2n+1}$)$_2$, N(Ar$_1$)(Ar$_2$), CH=CH—C$_n$H$_{2n+1}$, C≡C—C$_n$H$_{2n+1}$, Ar$_1$, Ar$_1$-Ar$_2$, and C$_n$H$_{2n}$—Ar$_1$, or the host has no substitutions; wherein n is from 1 to 10; and wherein Ar$_1$ and Ar$_2$ are independently selected from the group consisting of benzene, biphenyl, naphthalene, triphenylene, carbazole, and heteroaromatic analogs thereof. In some other embodiments, the host comprises a compound selected from the group consisting of: carbazole, dibenzothiphene, dibenzofuran, dibenzoselenophene, azacarbazole, aza-dibenzothiophene, aza-dibenzofuran, and aza-dibenzoselenophene.

In some embodiments, the host is a compound selected from the group consisting of:

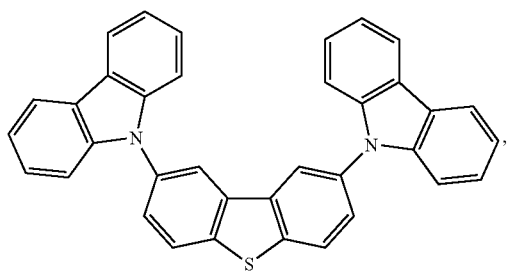

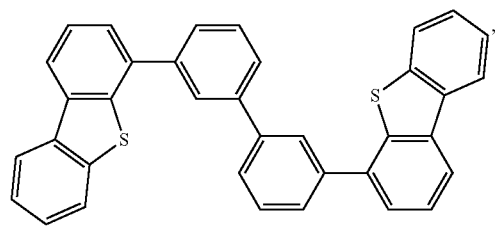

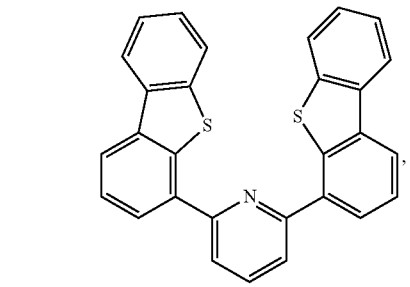

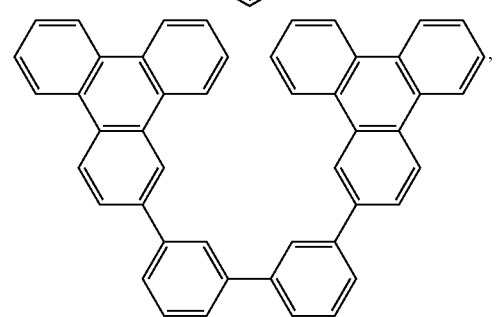

-continued

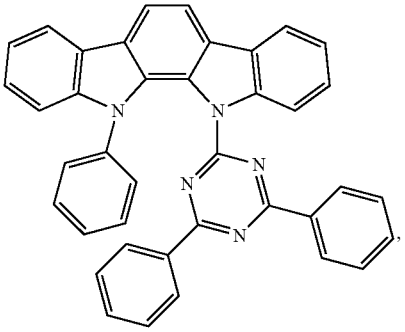

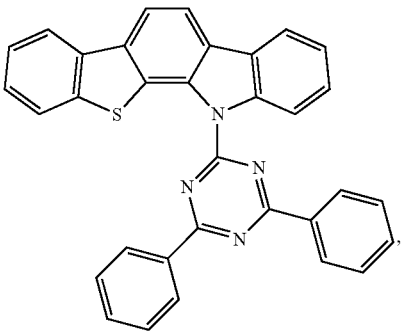

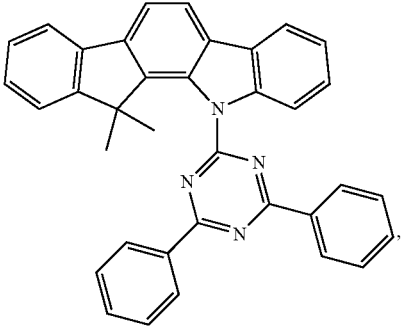

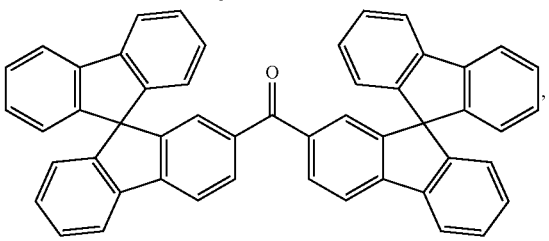

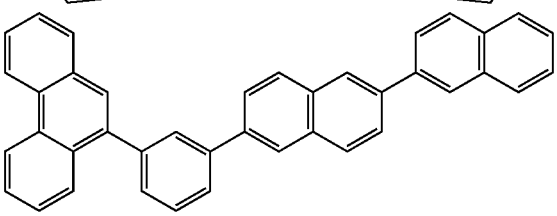

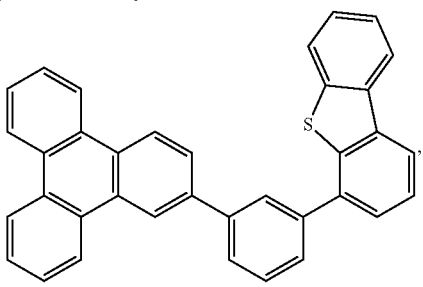

and

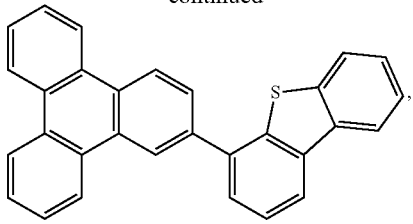

and combinations thereof.

In some embodiments, the host is a metal complex.

Combination with Other Materials

The materials described herein as useful for a particular layer in an organic light emitting device may be used in combination with a wide variety of other materials present in the device. For example, emissive dopants disclosed herein may be used in conjunction with a wide variety of hosts, transport layers, blocking layers, injection layers, electrodes and other layers that may be present. The materials described or referred to below are non-limiting examples of materials that may be useful in combination with the compounds disclosed herein, and one of skill in the art can readily consult the literature to identify other materials that may be useful in combination.

HIL/HTL:

A hole injecting/transporting material to be used in the present invention is not particularly limited, and any compound may be used as long as the compound is typically used as a hole injecting/transporting material. Examples of the material include, but not limit to: a phthalocyanine or porphryin derivative; an aromatic amine derivative; an indolocarbazole derivative; a polymer containing fluorohydrocarbon; a polymer with conductivity dopants; a conducting polymer, such as PEDOT/PSS; a self-assembly monomer derived from compounds such as phosphonic acid and sliane derivatives; a metal oxide derivative, such as $MoO_x$; a p-type semiconducting organic compound, such as 1,4,5,8,9,12-Hexaazatriphenylenehexacarbonitrille; a metal complex, and a cross-linkable compounds.

Examples of aromatic amine derivatives used in HIL or HTL include, but not limit to the following general structures:

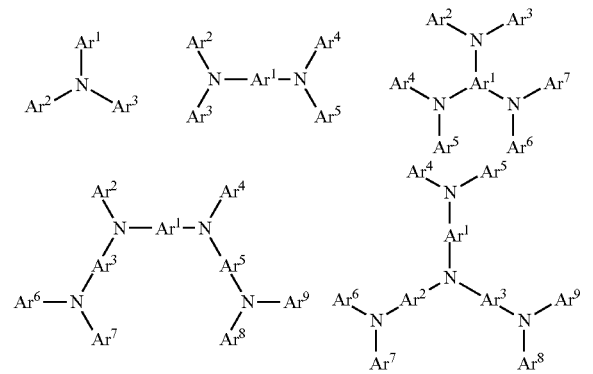

Each of $Ar^1$ to $Ar^9$ is selected from the group consisting aromatic hydrocarbon cyclic compounds such as benzene, biphenyl, triphenyl, triphenylene, naphthalene, anthracene, phenalene, phenanthrene, fluorene, pyretic, chrysene, perylene, azulene; group consisting aromatic heterocyclic compounds such as dibenzothiophene, dibenzofuran, dibenzoselenophene, furan, thiophene, benzofuran, benzothiophene, benzoselenophene, carbazole, indolocarbazole, pyridylindole, pyrrolodipyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazine, oxadiazine, indole, benzimidazole, indazole, indoxazine, benzoxazole, benzisoxazole, benzothiazole, quinoline, isoquinoline, cinnoline, quinazoline, quinoxaline, naphthyridine, phthalazine, pteridine, xanthene, acridine, phenazine, phenothiazine, phenoxazine, benzofuropyridine, furodipyridine, benzothienopyridine, thienodipyridine, benzoselenophenopyridine, and selenophenodipyridine; and group consisting 2 to 10 cyclic structural units which are groups of the same type or different types selected from the aromatic hydrocarbon cyclic group and the aromatic heterocyclic group and are bonded to each other directly or via at least one of oxygen atom, nitrogen atom, sulfur atom, silicon atom, phosphorus atom, boron atom, chain structural unit and the aliphatic cyclic group. Wherein each Ar is further substituted by a substituent selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

In one aspect, $Ar^1$ to $Ar^9$ is independently selected from the group consisting of:

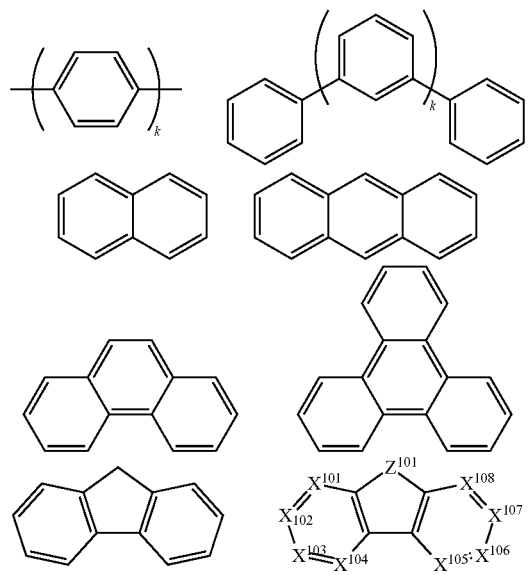

k is an integer from 1 to 20; $X^{101}$ to $X^{108}$ is C (including CH) or N; $Z^{101}$ is $NAr^1$, O, or S; $Ar^1$ has the same group defined above.

Examples of metal complexes used in HIL or HTL include, but not limit to the following general formula:

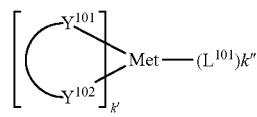

Met is a metal; ($Y^{101}$-$Y^{102}$) is a bidentate ligand, $Y^{101}$ and $Y^{102}$ are independently selected from C, N, O, P. and S; $L^{101}$ is another ligand; k' is an integer value from 1 to the maximum number of ligands that may be attached to the metal; and k'+k" is the maximum number of ligands that may be attached to the metal.

In one aspect, ($Y^{101}$-$Y^{101}$) is a 2-phenylpyridine derivative.

In another aspect, $Y^{101}$-$Y^{102}$ carbene ligand.

In another aspect, Met is selected from Ir, Pt, Os, and Zn.

In a further aspect, the metal complex has a smallest oxidation potential in solution vs. Fc$^+$/Fc couple less than about 0.6 V.

Host:

The light emitting layer of the organic EL device of the present invention preferably contains at least a metal complex as light emitting material, and may contain a host material using the metal complex as a dopant material. Examples of the host material are not particular limited, and any metal complexes or organic compounds may be used as long as the triplet energy of the host is larger than that of the dopant. While the Table below categorizes host materials as preferred for devices that emit various colors, any host material may be used with any dopant so long as the triplet criteria is satisfied.

Examples of metal complexes used as host are preferred to have the following general formula:

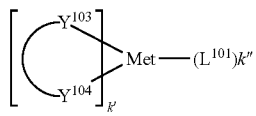

Met is a metal; ($Y^{103}$-$Y^{104}$) is a bidentate ligand, $Y^{103}$ and $Y^{104}$ are independently selected from C, N, O, P, and S; $L^{101}$ is another ligand; k' is an integer value from 1 to the maximum number of ligands that may be attached to the metal; and k'+k" is the maximum number of ligands that may be attached to the metal.

In one aspect, the metal complexes are:

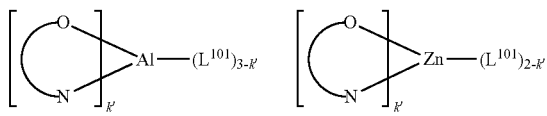

(O—N) is a bidentate ligand, having metal coordinated to atoms O and N.

In another aspect, Met is selected from Ir and Pt.

In a further aspect, ($Y^{103}$-$Y^{104}$) is a carbene ligand.

Examples of organic compounds used as host are selected from the group consisting aromatic hydrocarbon cyclic compounds such as benzene, biphenyl, triphenyl, triphenylene, naphthalene, anthracene, phenalene, phenanthrene, fluorene, pyrene, chrysene, perylene, azulene; group consisting aromatic heterocyclic compounds such as dibenzothiophene, dibenzotbran, dibenzoselenophene, furan, thiophene, benzofuran, benzothiophene, benzoselenophene, carbazole, indolocarbazole, pyridylindole, pyrrolodipyridine, pyrazole, imidazole, triazole, oxazole, thiazole, oxadiazole, oxatriazole, dioxazole, thiadiazole, pyridine, pyridazine, pyritnidine, pyrazine, triazine, oxazine, oxathiazine, oxadiazine, indole, benzimidazole, indazole, indoxazine, benzoxazole, benzisoxazole, benzothiazole, quinoline, isoquinoline, cinnoline, quinazoline, quinoxaline, naphthyridine, phthalazine, pteridine, xanthene, acridine, phenazine, phenothiazine, phenoxazine, benzofuropytidine, furodipyridine, benzothienopyridine, thienodipyridine, benzoselenophenopyridine, and selenophenodipyridine; and group consisting 2 to 10 cyclic structural units which are groups of the same type or different types selected from the aromatic hydrocarbon cyclic group and the aromatic heterocyclic group and are bonded to each other directly or via at least one of oxygen atom, nitrogen atome, sulfur atom, silicon atom, phosphorus atom, boron atom, chain structural unit and the aliphatic cyclic group. Wherein each group is further substituted by a substituent selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl heteroaryl, acyl, carbonyl, carboxylic acids, ester, nitrite, isonitrile, sulfanyl, sulfinyl, sulfonyl, phosphino, and combinations thereof.

In one aspect, host compound contains at least one of the following groups in the molecule:

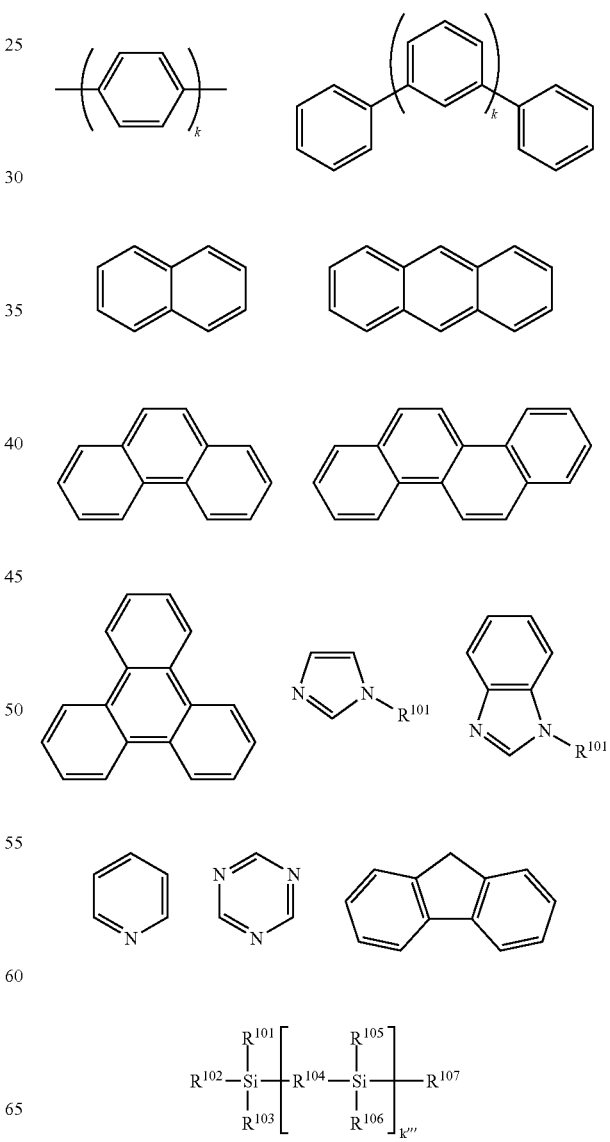

-continued

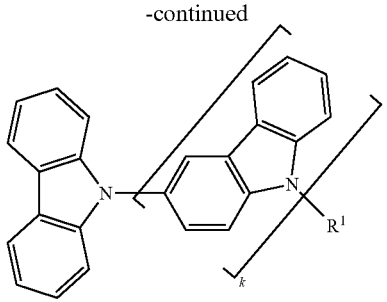

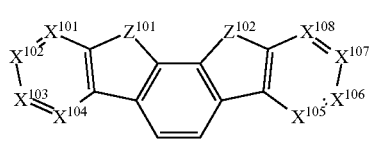

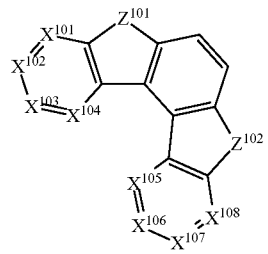

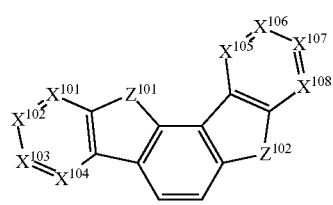

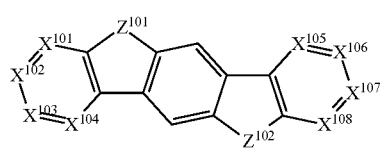

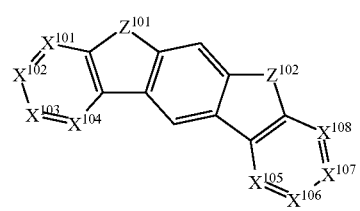

$R^{101}$ to $R^{107}$ is independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof, when it is aryl or heteroaryl, it has the similar definition as Ar's mentioned above.

k is an integer from 1 to 20; k''' is an integer from 0 to 20. $X^{101}$ to $X^{108}$ is selected from C (including CH) or N. $Z^{100}$ and $Z^{102}$ is selected from $NR^{101}$, O, or S.

HBL:

A hole blocking layer (HBL) may be used to reduce the number of holes and/or excitons that leave the emissive layer. The presence of such a blocking layer in a device may result in substantially higher efficiencies as compared to a similar device lacking a blocking layer. Also, a blocking layer may be used to confine emission to a desired region of an OLED.

In one aspect, compound used in HBL contains the same molecule or the same functional groups used as host described above.

In another aspect, compound used in HBL contains at least one of the following groups in the molecule:

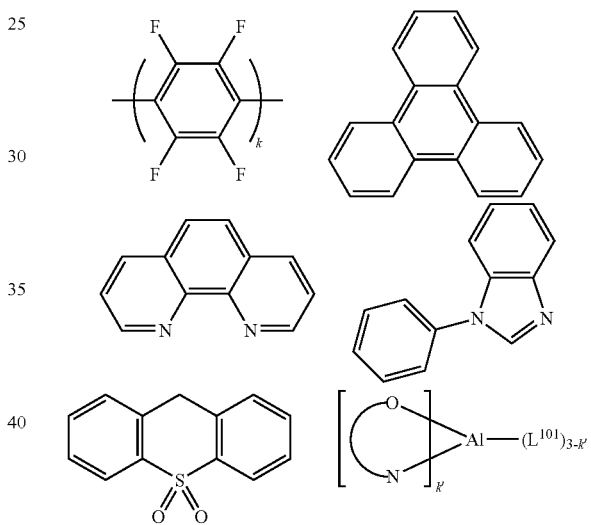

k is an integer from 1 to 20; $L^{101}$ is another ligand, k' is an integer from 1 to 3.

ETL:

Electron transport layer (EFL) may include a material capable of transporting electrons. Electron transport layer may be intrinsic (undoped), or doped. Doping may be used to enhance conductivity. Examples of the ETL material are not particularly limited, and any metal complexes or organic compounds may be used as long as they are typically used to transport electrons.

In one aspect, compound used in ETL contains at least one of the following groups in the molecule:

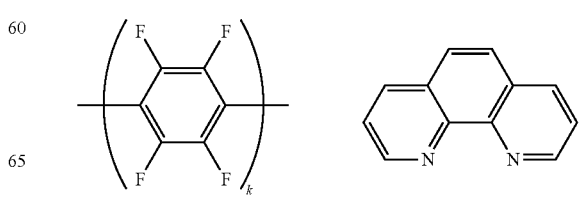

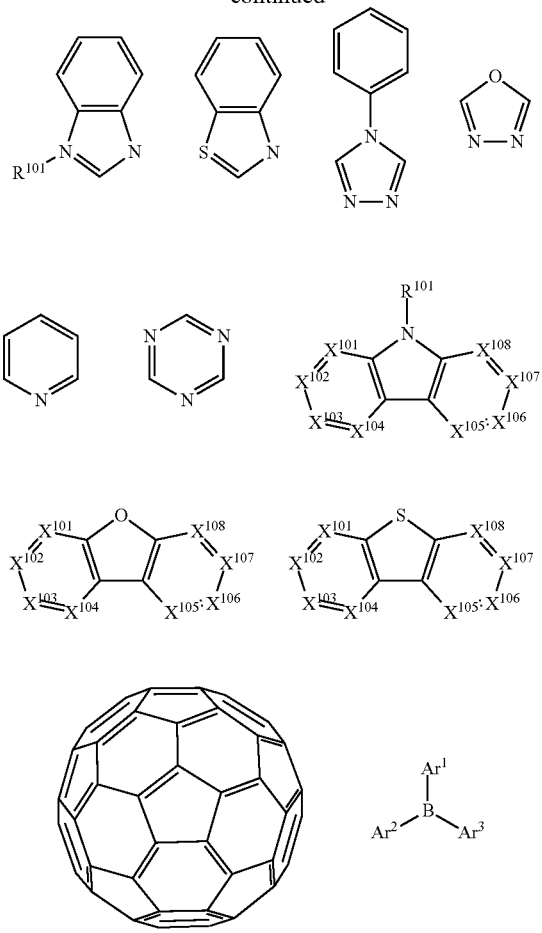

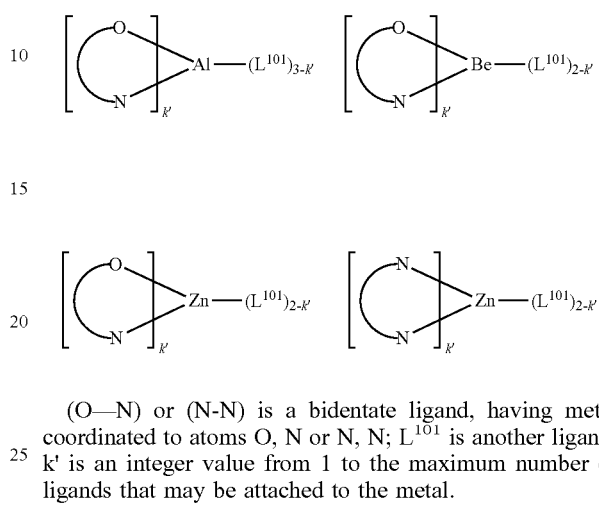

$Ar^1$ to $Ar^3$ has the similar definition as Ar's mentioned above.

k is an integer from 1 to 20.

$X^{101}$ to $X^{108}$ is selected from C (including CH) or N.

In another aspect, the metal complexes used in ETL contains, but not limit to the following general formula:

$R^{101}$ is selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof, when it is aryl or heteroaryl, it has the similar definition as Ar's mentioned above.

(O—N) or (N-N) is a bidentate ligand, having metal coordinated to atoms O, N or N, N; $L^{101}$ is another ligand; k' is an integer value from 1 to the maximum number of ligands that may be attached to the metal.

In any above-mentioned compounds used in each layer of the OLED device, the hydrogen atoms can be partially or fully deuterated. Thus, any specifically listed substituent, such as, without limitation, methyl, phenyl, pyridyl, etc. encompasses undeuterated, partially deuterated, and fully deuterated versions thereof. Similarly, classes of substituents such as, without limitation, alkyl, aryl, cycloalkyl, heteroaryl, etc. also encompass undeuterated, partially deuterated, and fully deuterated versions thereof.

In addition to and/or in combination with the materials disclosed herein, many hole injection materials, hole transporting materials, host materials, dopant materials, exiton/hole blocking layer materials, electron transporting and electron injecting materials may be used in an OLED. Non-limiting examples of the materials that may be used in an OLED in combination with materials disclosed herein are listed in Table 1 below. Table 1 lists non-limiting classes of materials, non-limiting examples of compounds for each class, and references that disclose the materials.

TABLE 1

| MATERIAL | EXAMPLES OF MATERIAL | PUBLICATIONS |
|---|---|---|
| Hole injection materials | | |
| Phthalocyanine and porphryin compounds | | Appl. Phys. Lett. 69, 2160 (1996) |

TABLE 1-continued

| MATERIAL | EXAMPLES OF MATERIAL | PUBLICATIONS |
| --- | --- | --- |
| Starburst triarylamines | [structure of starburst triarylamine with four naphthyl-phenyl-amine arms connected via phenylene linkers to a central nitrogen] | J. Lumin. 72-74, 985 (1997) |
| $CF_x$ Fluorohydrocarbon polymer | $-\!\!+\!CH_xF_y\!\!+_n\!\!-$ | Appl. Phys. Lett. 78, 673 (2001) |
| Conducting polymers (e.g., PEDOT:PSS, polyaniline, polypthiophene) | [PEDOT structure] + [PSS structure with $SO_3^-(H^+)$] | Synth. Met. 87, 171 (1997) WO2007002683 |
| Phosphonic acid and sliane SAMs | $N\!\!-\!\!(\!\!-\!\!\langle\bigcirc\rangle\!\!-\!\!SiCl_3)_3$ | US20030162053 |
| Triarylamine or polythiophene polymers with conductivity dopants | [structure of triarylamine polymer with methoxy and benzophenone substituents] and | EP1725079A1 |

TABLE 1-continued
| MATERIAL | EXAMPLES OF MATERIAL | PUBLICATIONS |
|---|---|---|
| | 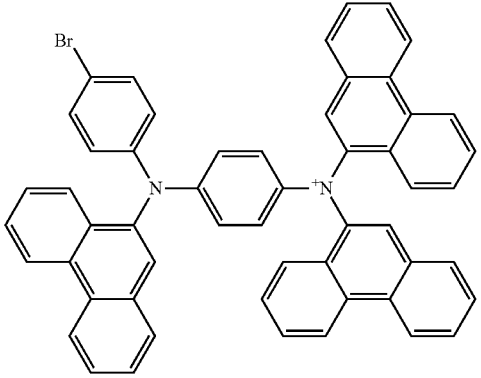 [SMILES: Brc1ccc(N(c2ccc([NH+](c3cc4ccccc4c4ccccc34)c3cc4ccccc4c4ccccc34)cc2)c2cc3ccccc3c3ccccc23)cc1] | |
| | 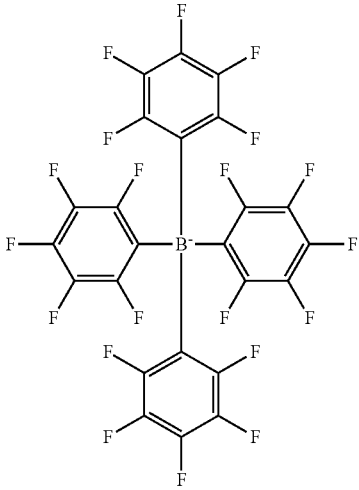 [SMILES: Fc1c(F)c(F)c([B-](c2c(F)c(F)c(F)c(F)c2F)(c2c(F)c(F)c(F)c(F)c2F)c2c(F)c(F)c(F)c(F)c2F)c(F)c1F] | |
| Organic compounds with conductive inorganic compounds, such as molybdenum and tungsten oxides | 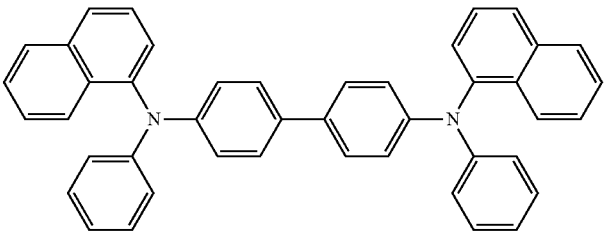 + $MoO_x$ | US20050123751<br>SID Symposium Digest, 37, 923 (2006)<br>WO2009018009 |
| n-type semiconducting organic complexes | 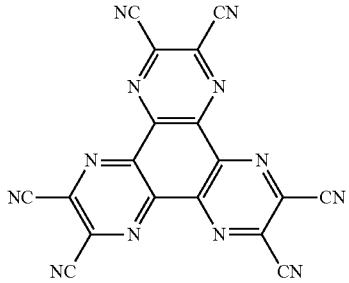 [SMILES: N#Cc1nc2c3nc(C#N)c(C#N)nc3c3nc(C#N)c(C#N)nc3c2nc1C#N] | US20020158242 |

TABLE 1-continued

| MATERIAL | EXAMPLES OF MATERIAL | PUBLICATIONS |
| --- | --- | --- |
| Metal organometallic complexes | | US20060240279 |
| Cross-linkable compounds | | US20080220265 |
| Polythiophene based polymers and copolymers | | WO 2011075644<br>EP2350216 |
| Hole transporting materials | | |
| Triarylamines (e.g., TPD, α-NPD) | | Appl. Phys. Lett. 51, 913 (1987) |

TABLE 1-continued
| MATERIAL | EXAMPLES OF MATERIAL | PUBLICATIONS |
|---|---|---|
| | 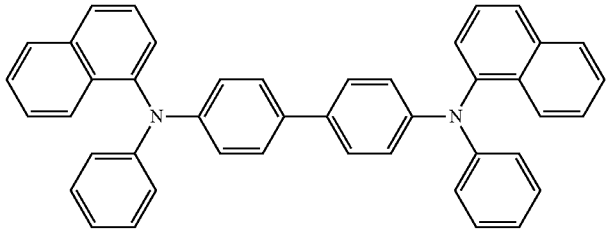 [SMILES: c1ccc(N(c2ccc(-c3ccc(N(c4ccccc4)c4cccc5ccccc45)cc3)cc2)c2cccc3ccccc23)cc1] | U.S. Pat. No. 5,061,569 |
| | 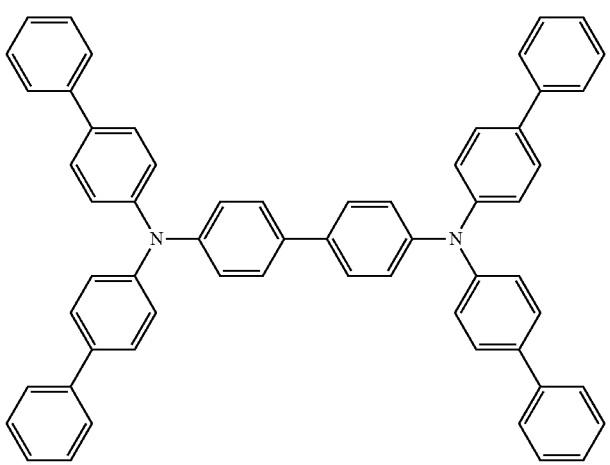 [SMILES: c1ccc(-c2ccc(N(c3ccc(-c4ccccc4)cc3)c3ccc(-c4ccc(N(c5ccc(-c6ccccc6)cc5)c5ccc(-c6ccccc6)cc5)cc4)cc3)cc2)cc1] | EP650955 |
| | 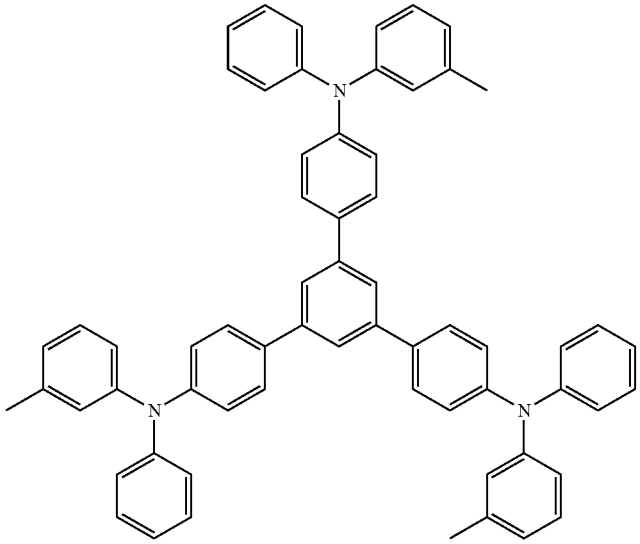 [SMILES: Cc1cccc(N(c2ccccc2)c2ccc(-c3cc(-c4ccc(N(c5ccccc5)c5cccc(C)c5)cc4)cc(-c4ccc(N(c5ccccc5)c5cccc(C)c5)cc4)c3)cc2)c1] | J. Mater. Chem. 3, 319 (1993) |

TABLE 1-continued

| MATERIAL | EXAMPLES OF MATERIAL | PUBLICATIONS |
|---|---|---|
|  |  | Appl. Phys. Lett. 90, 183503 (2007) |
|  |  | Appl. Phys. Lett. 90, 183503 (2007) |
| Triaylamine on spirofluorene core |  | Synth. Met. 91, 209 (1997) |
| Arylamine carbazole compounds |  | Adv. Mater. 6, 677 (1994), US20080124572 |

TABLE 1-continued
| MATERIAL | EXAMPLES OF MATERIAL | PUBLICATIONS |
| --- | --- | --- |
| Triarylamine with (di)benzothiophene/ (di)benzofuran | 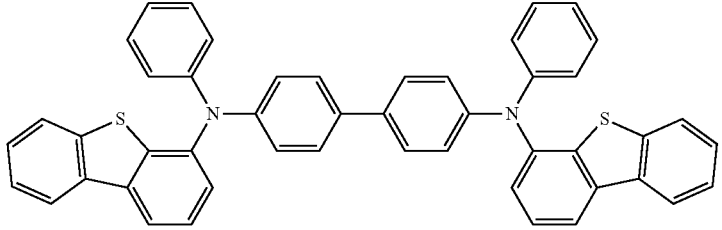 [SMILES: c1ccc(N(c2ccc(-c3ccc(N(c4ccccc4)c4cccc5c4sc4ccccc45)cc3)cc2)c2cccc3c2sc2ccccc23)cc1] | US20070278938, US20080106190 US20110163302 |
| Indolocarbazoles | 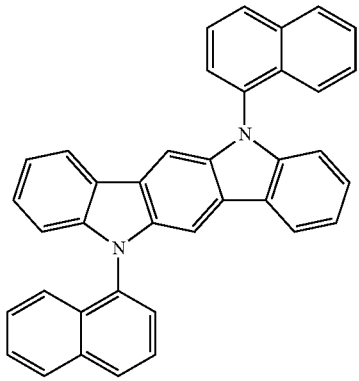 [SMILES: c1ccc2c(-n3c4ccccc4c4cc5c(cc43)c3ccccc3n5-c3cccc4ccccc34)cccc2c1] | Synth. Met. 111, 421 (2000) |
| Isoindole compounds | 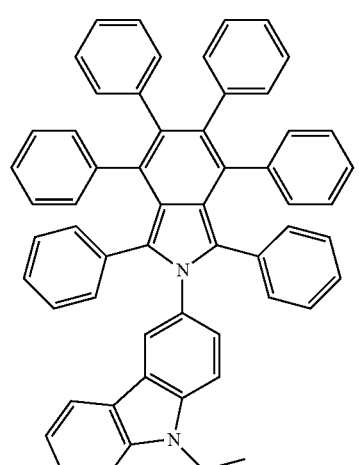 | Chem. Mater. 15, 3148 (2003) |
| Metal carbene complexes | 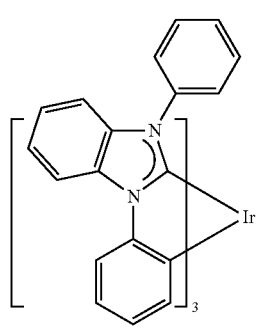 | US20080018221 |

TABLE 1-continued

| MATERIAL | EXAMPLES OF MATERIAL | PUBLICATIONS |
| --- | --- | --- |
| | Phosphorescent OLED host materials<br>Red hosts | |
| Arylcarbazoles | | Appl. Phys. Lett.<br>78, 1622 (2001) |
| Metal<br>8-hydroxyquinolates<br>(e.g., Alq$_3$, BAlq) | | Nature 395,<br>151 (1998) |
| | | US20060202194 |
| | | WO2005014551 |
| | | WO2006072002 |
| Metal<br>phenoxybenzothiazole<br>compounds | | Appl. Phys. Lett.<br>90, 123509 (2007) |
| Conjugated<br>oligomers and<br>polymers<br>(e.g., polyfluorene) | | Org. Electron. 1,<br>15 (2000) |

TABLE 1-continued

| MATERIAL | EXAMPLES OF MATERIAL | PUBLICATIONS |
|---|---|---|
| Aromatic fused rings | | WO2009066779, WO2009066778, WO2009063833, US20090045731, US20090045730, WO2009008311, US20090008605, US20090009065 |
| Zinc complexes | | WO2010056066 |
| Chrysene based compounds | | WO2011086863 |

Green hosts

| | | |
|---|---|---|
| Arylcarbazoles | | Appl. Phys. Lett. 78, 1622 (2001) |
| | | US20030175553 |
| | | WO2001039234 |

TABLE 1-continued
| MATERIAL | EXAMPLES OF MATERIAL | PUBLICATIONS |
|---|---|---|
| Aryltriphenylene compounds | 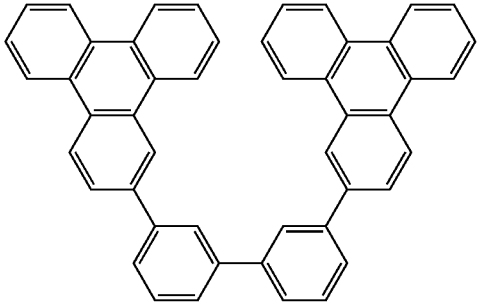 [SMILES: c1cc(-c2cccc(-c3ccc4c5ccccc5c5ccccc5c4c3)c2)cc(-c2ccc3c4ccccc4c4ccccc4c3c2)c1] | US20060280965 |
| | 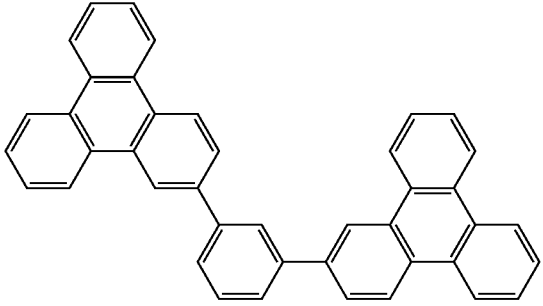 [SMILES: c1cc(-c2ccc3c4ccccc4c4ccccc4c3c2)cc(-c2ccc3c4ccccc4c4ccccc4c3c2)c1] | US20060280965 |
| | 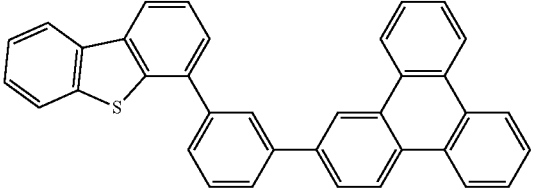 [SMILES: c1cc(-c2ccc3c4ccccc4c4ccccc4c3c2)cc(-c2cccc3c2sc2ccccc23)c1] | WO2009021126 |
| Poly-fused heteroaryl compounds | 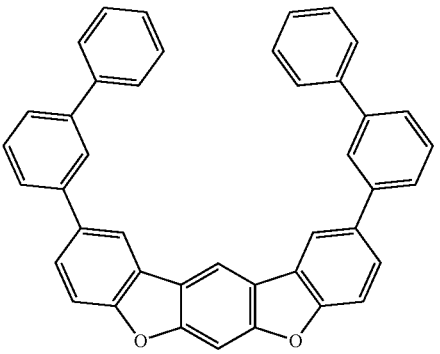 [SMILES: c1ccc(-c2cccc(-c3ccc4oc5cc6oc7ccc(-c8cccc(-c9ccccc9)c8)cc7c6cc5c4c3)c2)cc1] | US20090309488<br>US20090302743<br>US20100012931 |
| Donor acceptor type molecules | 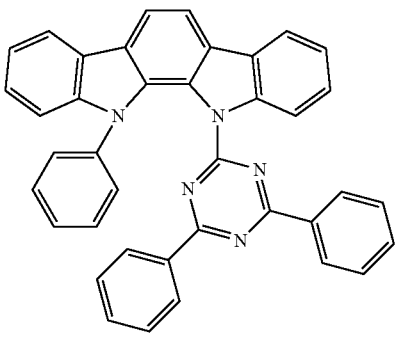 [SMILES: c1ccc(-c2nc(-c3ccccc3)nc(-n3c4ccccc4c4ccc5c6ccccc6n(-c6ccccc6)c5c43)n2)cc1] | WO2008056746 |

| MATERIAL | EXAMPLES OF MATERIAL | PUBLICATIONS |
|---|---|---|
| | 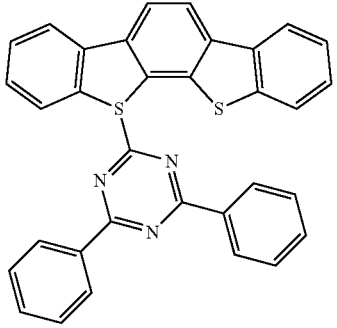 | WO2010107244 |
| Aza-carbazole/ DBT/DBF | 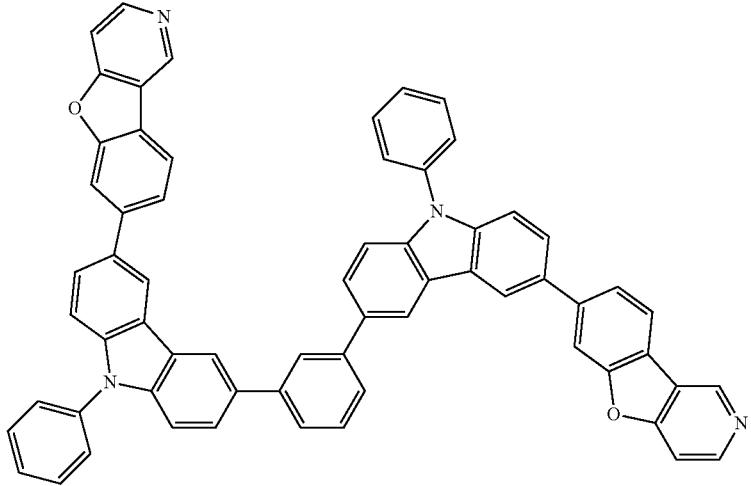 [SMILES: c1ccc(-n2c3ccc(-c4cccc(-c5ccc6c(c5)c5cc(-c7ccc8c(c7)oc7ccncc78)ccc5n6-c5ccccc5)c4)cc3c3cc(-c4ccc5c(c4)oc4ccncc45)ccc32)cc1] | JP2008074939 |
| | 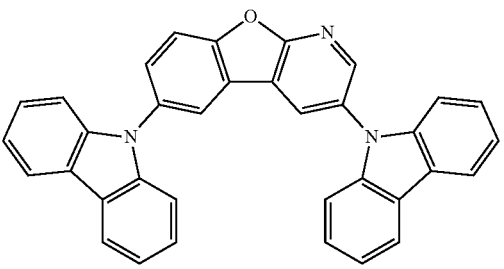 [SMILES: c1ccc2c(c1)c1ccccc1n2-c1ccc2oc3ncc(-n4c5ccccc5c5ccccc54)cc3c2c1] | US20100187984 |
| Polymers (e.g., PVK) | 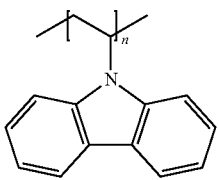 | Appl. Phys. Lett. 77, 2280 (2000) |
| Spirofluorene compounds | 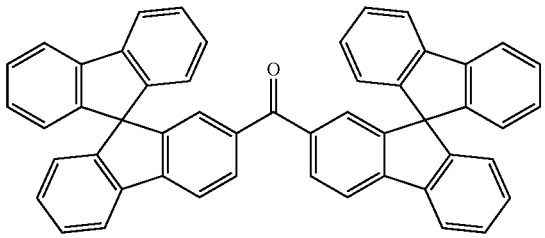 [SMILES: O=C(c1ccc2c(c1)C1(c3ccccc3-c3ccccc31)c1ccccc1-2)c1ccc2c(c1)C1(c3ccccc3-c3ccccc31)c1ccccc1-2] | WO2004093207 |

TABLE 1-continued

| MATERIAL | EXAMPLES OF MATERIAL | PUBLICATIONS |
|---|---|---|
| Metal phenoxybenzooxazole compounds | | WO2005089025 |
| | | WO2006132173 |
| | | JP200511610 |
| Spirofluorene-carbazole compounds | | JP2007254297 |
| | | JP2007254297 |

TABLE 1-continued

| MATERIAL | EXAMPLES OF MATERIAL | PUBLICATIONS |
| --- | --- | --- |
| Indolocabazoles |  | WO2007063796 |
|  |  | WO2007063754 |
| 5-member ring electron deficient heterocycles (e.g., triazole, oxadiazole) |  | J. Appl. Phys. 90, 5048 (2001) |
|  |  | WO2004107822 |
| Tetraphenylene complexes |  | US20050112407 |

TABLE 1-continued

| MATERIAL | EXAMPLES OF MATERIAL | PUBLICATIONS |
| --- | --- | --- |
| Metal phenoxypyridine compounds | | WO2005030900 |
| Metal coordination complexes (e.g., Zn, Al with N^N ligands) | | US20040137268, US20040137267 |

Blue hosts

| MATERIAL | EXAMPLES OF MATERIAL | PUBLICATIONS |
| --- | --- | --- |
| Arylcarbazoles | | Appl. Phys. Lett. 82, 2422 (2003) |
| | | US20070190359 |
| Dibenzothiophene/ Dibenzofuran-carbazole compounds | | WO2006114966, US20090167162 |
| | | US20090167162 |

TABLE 1-continued
| MATERIAL | EXAMPLES OF MATERIAL | PUBLICATIONS |
|---|---|---|
| | 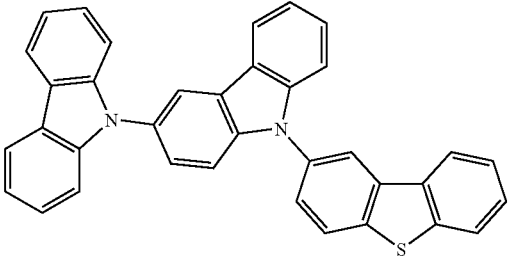 [SMILES: c1ccc2c(c1)sc1ccc(-n3c4ccccc4c4cc(-n5c6ccccc6c6ccccc65)ccc43)cc12] | WO2009086028 |
| | 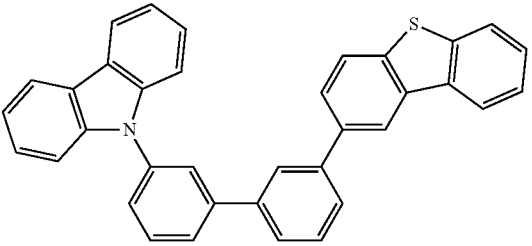 [SMILES: c1cc(-c2cccc(-n3c4ccccc4c4ccccc43)c2)cc(-c2ccc3sc4ccccc4c3c2)c1] | US20090030202, US20090017330 |
| | 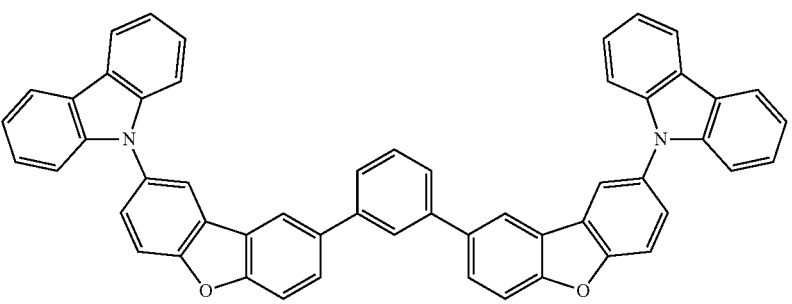 [SMILES: c1cc(-c2ccc3oc4ccc(-n5c6ccccc6c6ccccc65)cc4c3c2)cc(-c2ccc3oc4ccc(-n5c6ccccc6c6ccccc65)cc4c3c2)c1] | US20100084966 |
| Silicon aryl compounds | 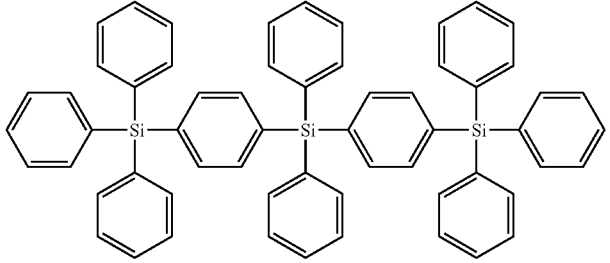 [SMILES: c1ccc([Si](c2ccccc2)(c2ccccc2)c2ccc([Si](c3ccccc3)(c3ccccc3)c3ccc([Si](c4ccccc4)(c4ccccc4)c4ccccc4)cc3)cc2)cc1] | US20050238919 |
| | 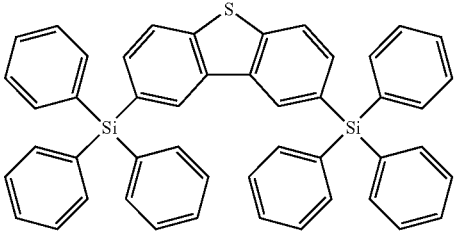 [SMILES: c1ccc([Si](c2ccccc2)(c2ccccc2)c2ccc3sc4ccc([Si](c5ccccc5)(c5ccccc5)c5ccccc5)cc4c3c2)cc1] | WO2009003898 |

TABLE 1-continued
| MATERIAL | EXAMPLES OF MATERIAL | PUBLICATIONS |
|---|---|---|
| Silicon/Germanium aryl compounds | 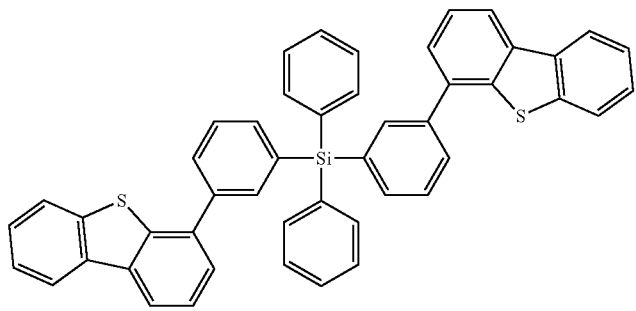 [SMILES: c1ccc([Si](c2ccccc2)(c2cccc(-c3cccc4c3sc3ccccc34)c2)c2cccc(-c3cccc4c3sc3ccccc34)c2)cc1] | EP2034538A |
| Aryl benzoyl ester | 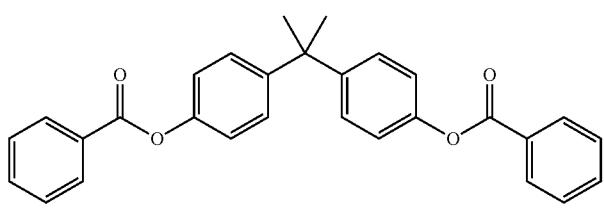 [SMILES: CC(C)(c1ccc(OC(=O)c2ccccc2)cc1)c1ccc(OC(=O)c2ccccc2)cc1] | WO2006100298 |
| Carbazole linked by non-conjugated groups | 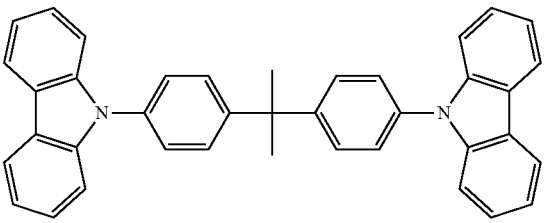 [SMILES: CC(C)(c1ccc(-n2c3ccccc3c3ccccc32)cc1)c1ccc(-n2c3ccccc3c3ccccc32)cc1] | US20040115476 |
| Aza-carbazoles | 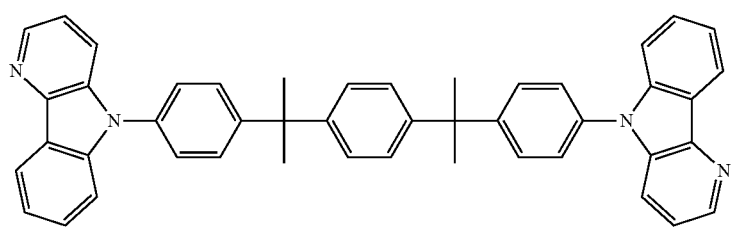 [SMILES: CC(C)(c1ccc(-n2c3ccccc3c3ncccc32)cc1)c1ccc(C(C)(C)c2ccc(-n3c4ccccc4c4ncccc43)cc2)cc1] | US20060121308 |
| High triplet metal organometallic complex | 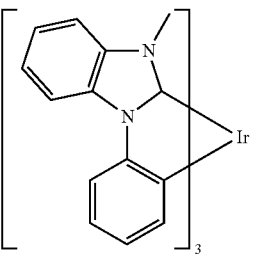 | U.S. Pat. No. 7,154,114 |

TABLE 1-continued

| MATERIAL | EXAMPLES OF MATERIAL | PUBLICATIONS |
|---|---|---|
| | Phosphorescent dopants | |
| | Red dopants | |
| Heavy metal porphyrins (e.g., PtOEP) | | Nature 395, 151 (1998) |
| Iridium (III) organometallic complexes | | Appl. Phys. Lett. 78, 1622 (2001) |
| | | US2006835469 |
| | | US2006835469 |
| | | US20060202194 |

TABLE 1-continued

| MATERIAL | EXAMPLES OF MATERIAL | PUBLICATIONS |
|---|---|---|
| | | US20060202194 |
| | | US20070087321 |
| | | US20080261076<br>US20100090591 |
| | | US20070087321 |
| | | Adv. Mater. 19, 739 (2007) |

TABLE 1-continued

| MATERIAL | EXAMPLES OF MATERIAL | PUBLICATIONS |
|---|---|---|
| | | WO2009100991 |
| | | WO2008101842 |
| | | U.S. Pat. No. 7,232,618 |
| Platinum (II) organometallic complexes | | WO2003040257 |
| | | US20070103060 |

TABLE 1-continued

| MATERIAL | EXAMPLES OF MATERIAL | PUBLICATIONS |
| --- | --- | --- |
| Osminum (III) complexes | | Chem. Mater. 17, 3532 (2005) |
| Ruthenium (II) complexes | | Adv. Mater. 17, 1059 (2005) |
| Rhenium (I), (II), and (III) complexes | | US20050244673 |
| | Green dopants | |
| Iridium (III) organometallic complexes | and its derivatives | Inorg. Chem. 40, 1704 (2001) |
| | | US20020034656 |

TABLE 1-continued
| MATERIAL | EXAMPLES OF MATERIAL | PUBLICATIONS |
|---|---|---|
| | 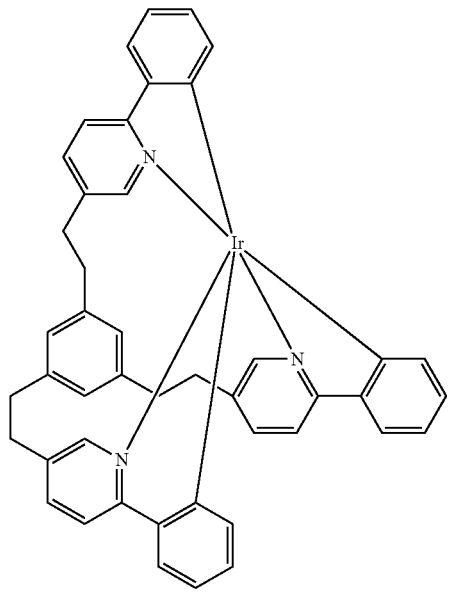 | U.S. Pat. No. 7,332,232 |
| | 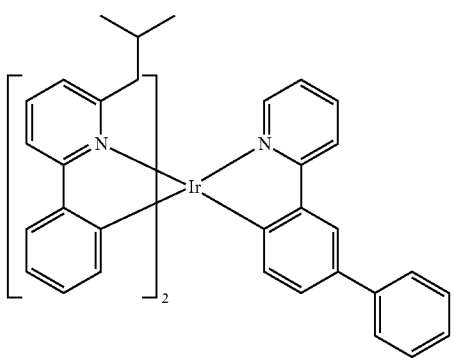 | US20090108737 |
| | 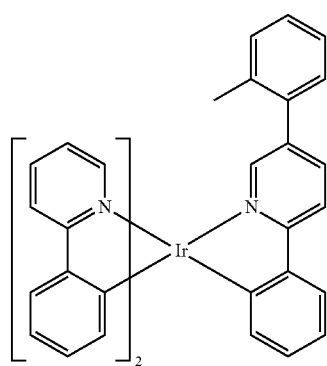 | WO2010028151 |

TABLE 1-continued
| MATERIAL | EXAMPLES OF MATERIAL | PUBLICATIONS |
|---|---|---|
| | 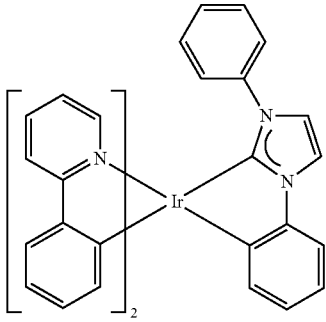 | EP1841834B |
| | 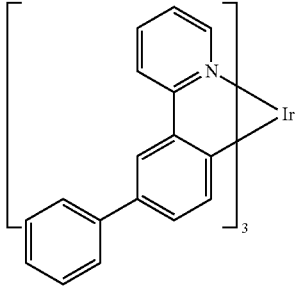 | US20060127696 |
| | 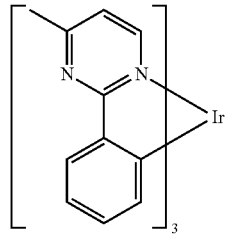 | US20090039776 |
| | 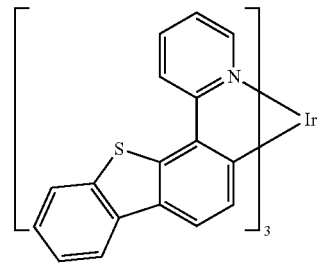 | U.S. Pat. No. 6,921,915 |
| | 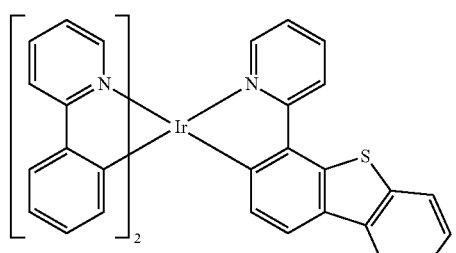 | US20100244004 |

TABLE 1-continued
| MATERIAL | EXAMPLES OF MATERIAL | PUBLICATIONS |
|---|---|---|
| | 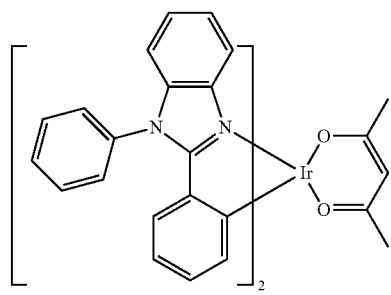 | U.S. Pat. No. 6,687,266 |
| | 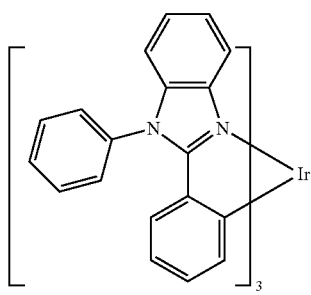 | Chem. Mater. 16, 2480 (2004) |
| | 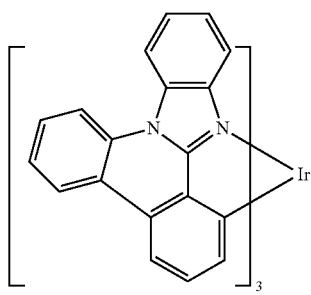 | US20070190359 |
| | 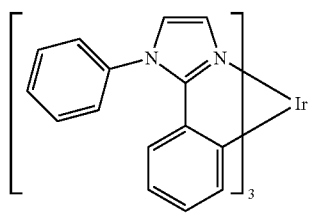 | US 20060008670 JP2007123392 |
| | 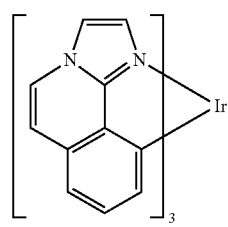 | WO2010086089, WO2011044988 |
| | 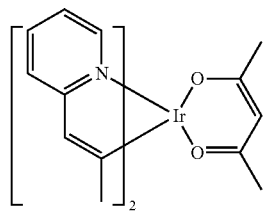 | Adv. Mater. 16, 2003 (2004) |

TABLE 1-continued

| MATERIAL | EXAMPLES OF MATERIAL | PUBLICATIONS |
| --- | --- | --- |
| | | Angew. Chem. Int. Ed. 2006, 45, 7800 |
| | | WO2009050290 |
| | | US20090165846 |
| | | US20080015355 |
| | | US20010015432 |
| | | US20100295032 |

TABLE 1-continued

| MATERIAL | EXAMPLES OF MATERIAL | PUBLICATIONS |
|---|---|---|
| Monomer for polymeric metal organometallic compounds | | U.S. Pat. No. 7,250,226, U.S. Pat. No. 7,396,598 |
| Pt (II) organometallic complexes, including polydentated ligands | | Appl. Phys. Lett. 86, 153505 (2005) |
| | | Appl. Phys. Lett. 86, 153505 (2005) |
| | | Chem. Lett. 34, 592 (2005) |
| | | WO2002015645 |

TABLE 1-continued

| MATERIAL | EXAMPLES OF MATERIAL | PUBLICATIONS |
|---|---|---|
| | | US20060263635 |
| | | US20060182992<br>US20070103060 |
| Cu complexes | | WO2009000673 |
| | | US20070111026 |

TABLE 1-continued
| MATERIAL | EXAMPLES OF MATERIAL | PUBLICATIONS |
| --- | --- | --- |
| Gold complexes | 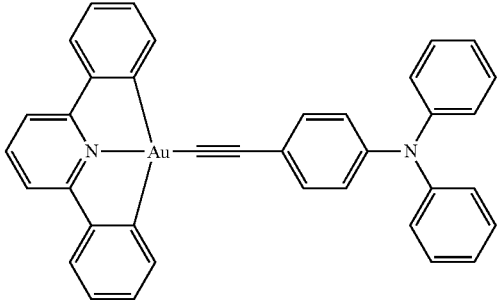 | Chem. Commun. 2906 (2005) |
| Rhenium (III) complexes | 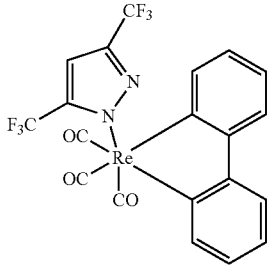 | Inorg. Chem. 42, 1248 (2003) |
| Osmium (II) complexes | 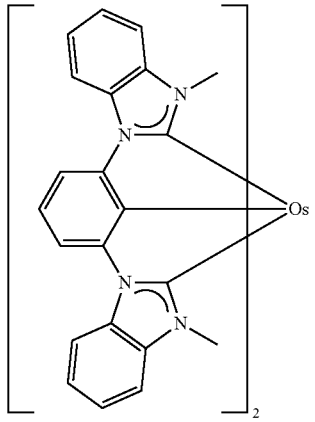 | U.S. Pat. No. 7,279,704 |
| Deuterated organometallic complexes | 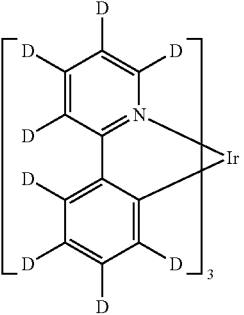 | US20030138657 |

TABLE 1-continued
| MATERIAL | EXAMPLES OF MATERIAL | PUBLICATIONS |
|---|---|---|
| Organometallic complexes with two or more metal centers | 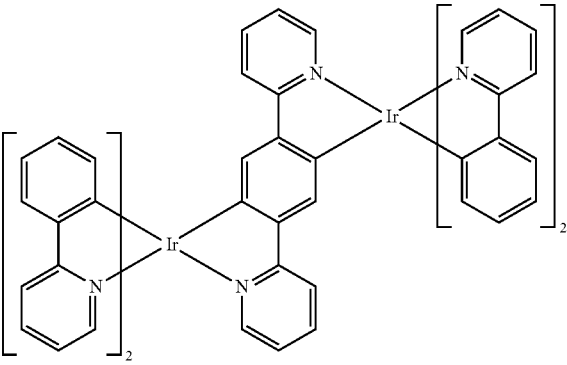 | US20030152802 |
| | 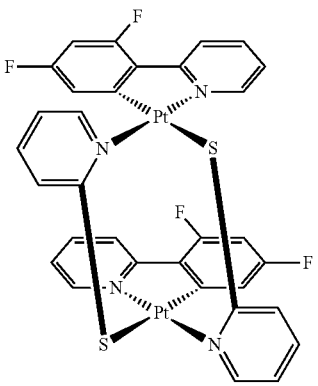 | U.S. Pat. No. 7,090,928 |
Blue dopants
| | | |
|---|---|---|
| Iridium (III) organometallic complexes | 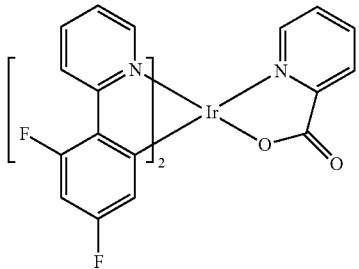 | WO2002002714 |
| | 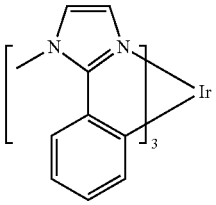 | WO2006009024 |
| | 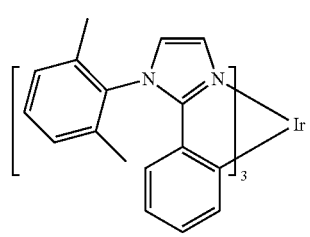 | US20060251923<br>US20110057559<br>US20110204333 |

TABLE 1-continued

| MATERIAL | EXAMPLES OF MATERIAL | PUBLICATIONS |
| --- | --- | --- |
|  |  | U.S. Pat. No. 7,393,599, WO2006056418, US20050260441, WO2005019373 |
|  |  | U.S. Pat. No. 7,534,505 |
|  |  | WO2011051404 |
|  |  | U.S. Pat. No. 7,445,855 |
|  |  | US20070190359, US20080297033 US20100148663 |

TABLE 1-continued

| MATERIAL | EXAMPLES OF MATERIAL | PUBLICATIONS |
| --- | --- | --- |
| | | U.S. Pat. No. 7,338,722 |
| | | US20020134984 |
| | | Angew. Chem. Int. Ed. 47, 1 (2008) |
| | | Chem. Mater. 18, 5119 (2006) |
| | | Inorg. Chem. 46, 4308 (2007) |

TABLE 1-continued

| MATERIAL | EXAMPLES OF MATERIAL | PUBLICATIONS |
|---|---|---|
| | | WO2005123873 |
| | | WO2005123873 |
| | | WO2007004380 |
| | | WO2006082742 |
| Osmium (II) complexes | | U.S. Pat. No. 7,279,704 |

TABLE 1-continued

| MATERIAL | EXAMPLES OF MATERIAL | PUBLICATIONS |
| --- | --- | --- |
| | [Os(PPh₃) complex structure] | Organometallics 23, 3745 (2004) |
| Gold complexes | [Ph₂P-PPh₂ bridged Au-Cl dimer structure] | Appl. Phys. Lett. 74, 1361 (1999) |
| Platinum (II) complexes | [Pt complex with thiophene and pyrazolylborate structure] | WO2006098120, WO2006103874 |
| Pt tetradentate complexes with at least one metal-carbene bond | [Pt tetradentate carbene complex structure] | U.S. Pat. No. 7,655,323 |
| Exciton/hole blocking layer materials | | |
| Bathocuprine compounds (e.g., BCP, BPhen) | [BCP structure] | Appl. Phys. Lett. 75, 4 (1999) |
| | [BPhen structure] | Appl. Phys. Lett. 79, 449 (2001) |
| Metal 8-hydroxyquinolates (e.g., BAlq) | [BAlq structure] | Appl. Phys. Lett. 81, 162 (2002) |

TABLE 1-continued

| MATERIAL | EXAMPLES OF MATERIAL | PUBLICATIONS |
|---|---|---|
| 5-member ring electron deficient heterocycles such as triazole, oxadiazole, imidazole, benzoimidazole | | Appl. Phys. Lett. 81, 162 (2002) |
| Triphenylene compounds | | US20050025993 |
| Fluorinated aromatic compounds | | Appl. Phys. Lett. 79, 156 (2001) |

TABLE 1-continued
| MATERIAL | EXAMPLES OF MATERIAL | PUBLICATIONS |
|---|---|---|
| Phenothiazine-S-oxide | 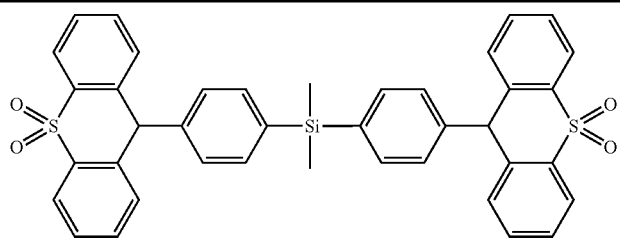 | WO2008132085 |
| Silylated five-membered nitrogen, oxygen, sulfur or phosphorus dibenzoheterocycles | 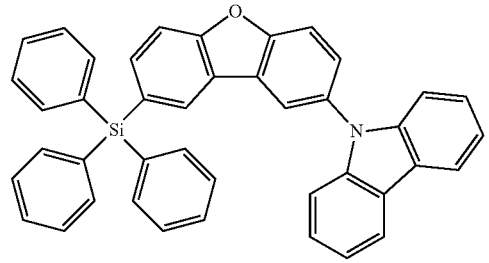 [SMILES: c1ccc([Si](c2ccccc2)(c2ccccc2)c2ccc3oc4ccc(-n5c6ccccc6c6ccccc65)cc4c3c2)cc1] | WO2010079051 |
| Aza-carbazoles | 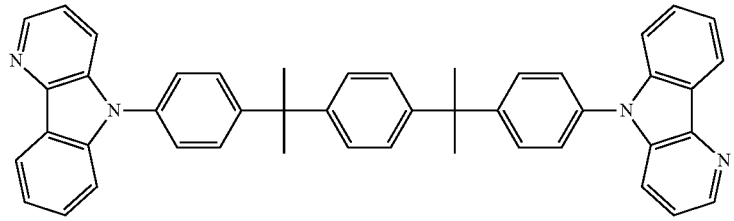 [SMILES: CC(C)(c1ccc(-n2c3ccccc3c3ncccc32)cc1)c1ccc(C(C)(C)c2ccc(-n3c4ccccc4c4ncccc43)cc2)cc1] | US20060121308 |
Electron transporting materials
| Anthracene-benzoimidazole compounds | 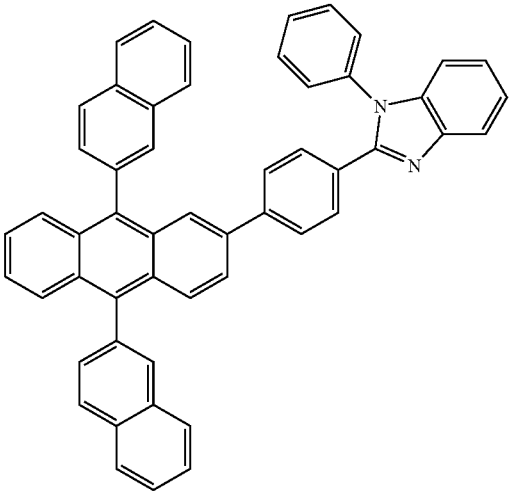 [SMILES: c1ccc(-n2c(-c3ccc(-c4ccc5c(-c6ccc7ccccc7c6)c6ccccc6c(-c6ccc7ccccc7c6)c5c4)cc3)nc3ccccc32)cc1] | WO2003060956 |
| | 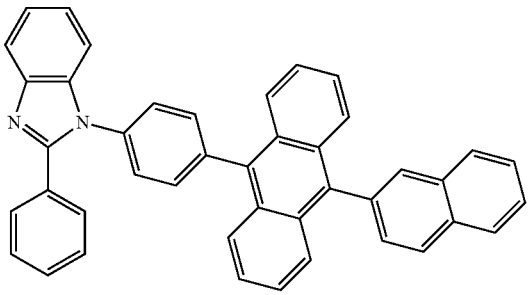 [SMILES: c1ccc(-c2nc3ccccc3n2-c2ccc(-c3c4ccccc4c(-c4ccc5ccccc5c4)c4ccccc34)cc2)cc1] | US20090179554 |

TABLE 1-continued

| MATERIAL | EXAMPLES OF MATERIAL | PUBLICATIONS |
| --- | --- | --- |
| Aza triphenylene derivatives | | US20090115316 |
| Anthracene-benzothiazole compounds | | Appl. Phys. Lett. 89, 063504 (2006) |
| Metal 8-hydroxyquinolates (e.g., Alq$_3$, Zrq$_4$) | | Appl. Phys. Lett. 51, 913 (1987)<br>U.S. Pat. No. 7,230,107 |
| Metal hydroxybenoquinolates | | Chem. Lett. 5, 905 (1993) |
| Bathocuprine compounds such as BCP, BPhen, etc | | Appl. Phys. Lett. 91, 263503 (2007) |
| | | Appl. Phys. Lett. 79, 449 (2001) |

TABLE 1-continued

| MATERIAL | EXAMPLES OF MATERIAL | PUBLICATIONS |
|---|---|---|
| 5-member ring electron deficient heterocycles (e.g., triazole, oxadiazole, imidazole, benzoimidazole) | | Appl. Phys. Lett. 74, 865 (1999) |
| | | Appl. Phys. Lett. 55, 1489 (1989) |
| | | Jpn. J. Apply. Phys. 32, L917 (1993) |
| Silole compounds | | Org. Electron. 4, 113 (2003) |
| Arylborane compounds | | J. Am. Chem. Soc. 120, 9714 (1998) |

TABLE 1-continued
| MATERIAL | EXAMPLES OF MATERIAL | PUBLICATIONS |
|---|---|---|
| Fluorinated aromatic compounds | 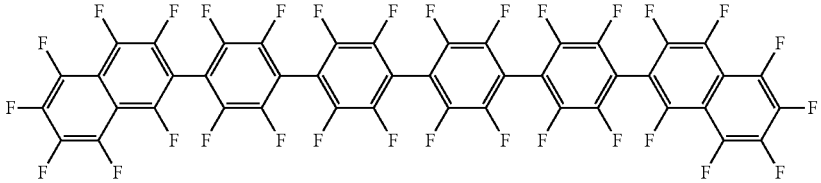 [SMILES: Fc1c(F)c(-c2c(F)c(F)c(-c3c(F)c(F)c4c(F)c(F)c(F)c(F)c4c3F)c(F)c2F)c(F)c(F)c1-c1c(F)c(F)c(-c2c(F)c(F)c(-c3c(F)c(F)c4c(F)c(F)c(F)c(F)c4c3F)c(F)c2F)c(F)c1F] | J. Am. Chem. Soc. 122, 1832 (2000) |
| Fullerene (e.g., C60) | 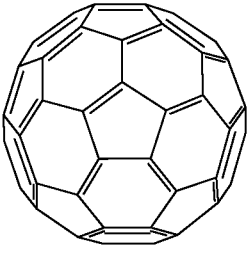 | US20090101870 |
| Triazine complexes | 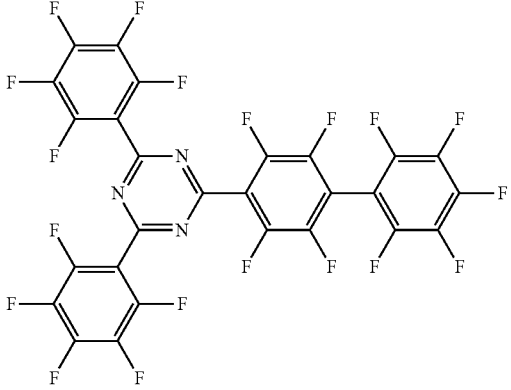 [SMILES: Fc1c(F)c(F)c(-c2nc(-c3c(F)c(F)c(F)c(F)c3F)nc(-c3c(F)c(F)c(-c4c(F)c(F)c(F)c(F)c4F)c(F)c3F)n2)c(F)c1F] | US20040036077 |
| Zn (N^N) complexes | 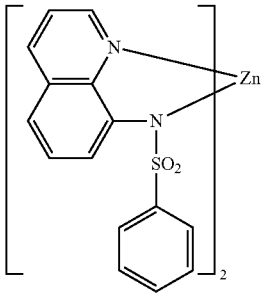 | U.S. Pat. No. 6,528,187 |

EXAMPLES

Example 1

Computational Examples

DFT calculations were performed for certain example compounds and comparative compounds. The example compounds and comparative compounds are shown on the following page. In certain models, a hot, Host 1, was used, which is also shown.

Comparative example 1

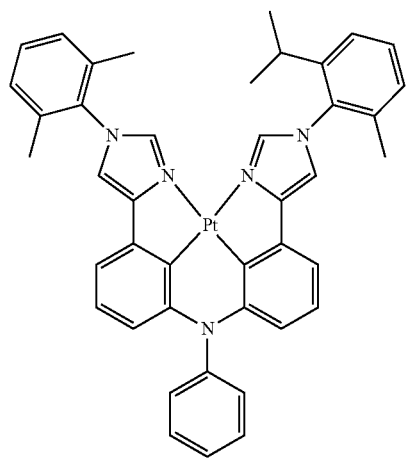

Comparative example 2

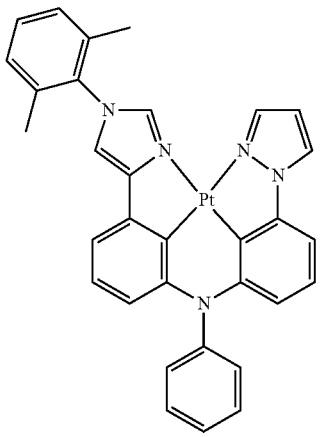

Comparative example 3

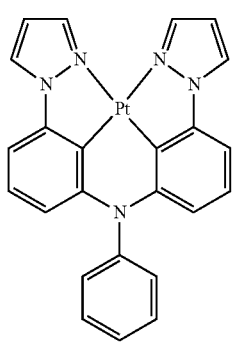

Comparative Example 4

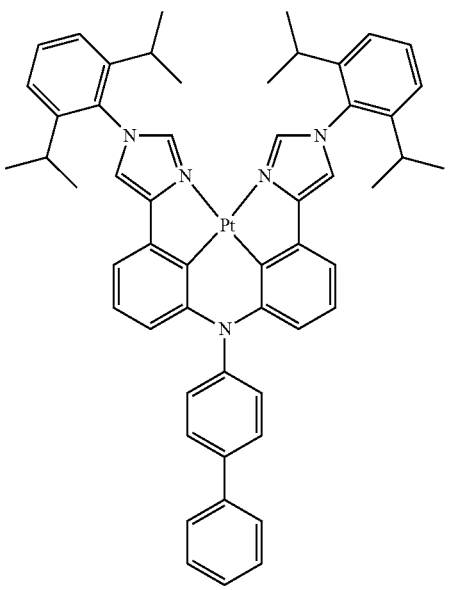

Comparative Example 5

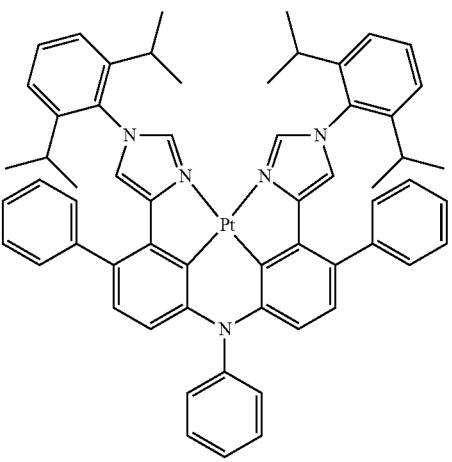

Comparative Example 6

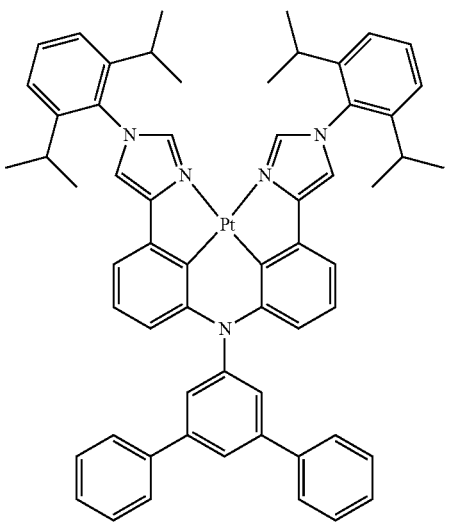

Comparative Example 7
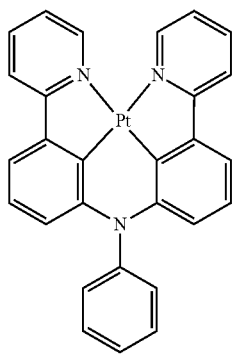
Comparative Example 8
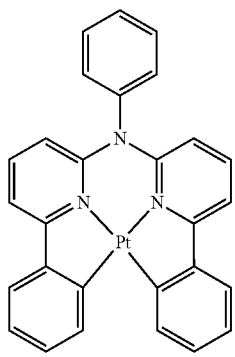
Comparative Example 9
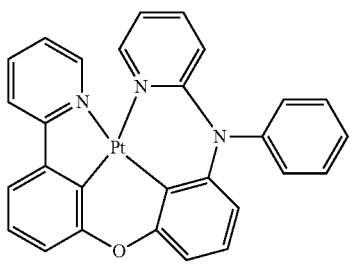
Compound 1
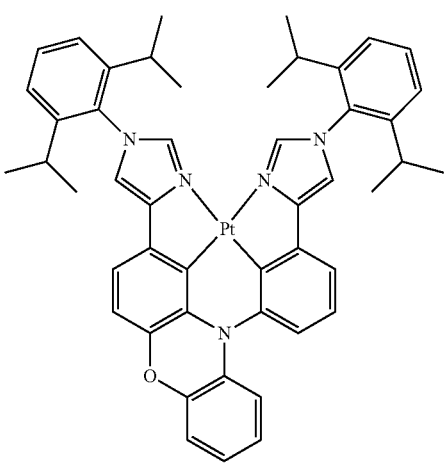
Compound 2
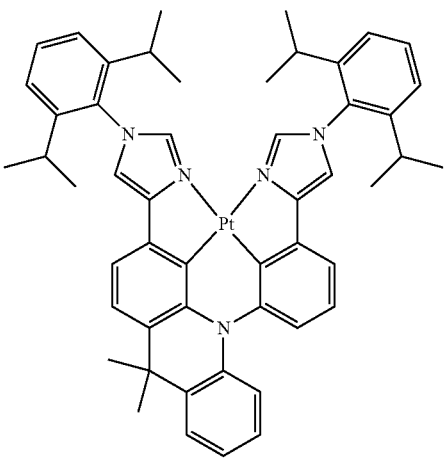
Compound 3
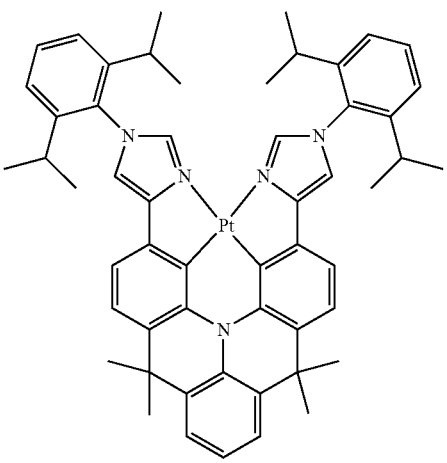
Compound 4
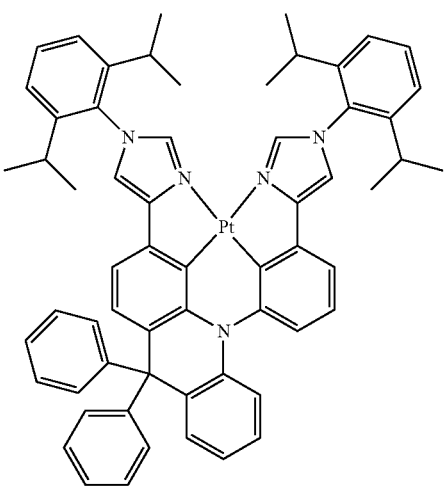

Compound 8

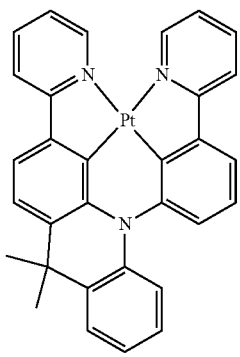

Compound 56

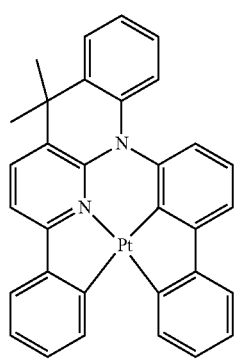

Compound 57

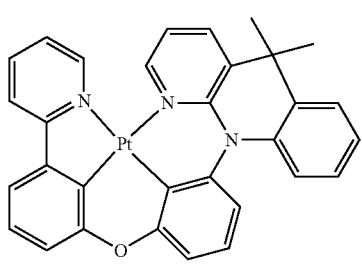

Compound 58

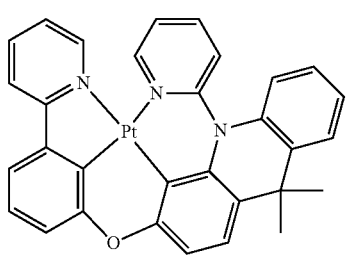

Host 1

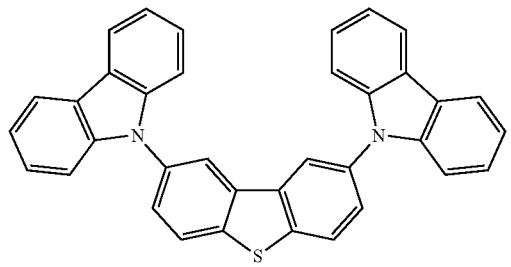

Geometry optimization calculations were performed within the Gaussian 09 software package using the B3LYP hybrid functional and CEP-31g effective core potential basis set. Complexes were optimized as both ground state singlets and triplets. Three bonds strengths of interest were examined: N-aryl, N-phenyl, and N-Phenyl2, the identities of which are shown in Structure A atop the following page.

Structure A

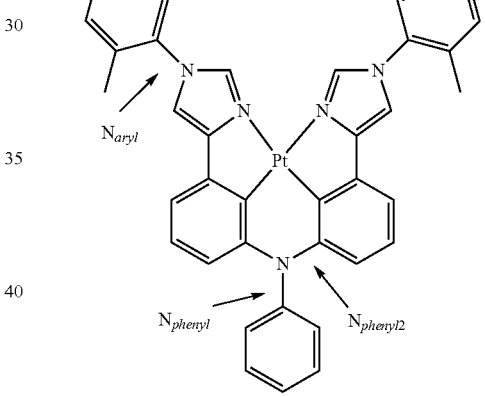

Bond strength calculations were executed at the same level of theory by two approaches which were dependent on either (a) creating two fragments or (b) breaking a bond that does not cause fragmentation.

Fragmentation of the phenyl group from the bridging nitrogen (Nphenyt) results in the transition metal fragment in a doublet spin state and the phenyl group also in a doublet spin state. The complete fragmentation is only observed for Comparative Examples 4-6, where the N-phenyl bond is not tethered. For these complexes, the Nphenyl fragment can be completely removed whereas for Compound 1-4, the phenyl fragment remains bound to the complex on one or both sides. For complexes that do not fragment the phenyl bonded to the bridging nitrogen both singlet→singlet and triplet→triplet spin states bond strength energies were calculated. The results are shown below in TABLE 2.

TABLE 2

| Compound | Calc T1 (nm) | N-Phenyl Bond Strength, singlet/triplet (kcal/mol) | N-Aryl Bond Strength, singlet/triplet (kcal/mol) | N-Phenyl-2 Bond Strength, singlet/triplet (kcal/mol) | Weakest bond (kcal/mol) | Device Lifetime (relative to comparative example 1) |
|---|---|---|---|---|---|---|
| Comparative Example 1 | 467 | 66.82/8.02 | 74.08/15.28 | 85.89/27.09 | 8.02 | 1 |
| Comparative Example 2 | 502 | 67.69/13.35 | 77.15/22.81 | | 13.35 | 10 |
| Comparative Example 3 | 508 | 68.79/15.32 | n/a | | 15.32 | 100 |
| Comparative Example 4 | 467 | 66.92/8.17 | 74.15/15.40 | 84.98/26.23 | 8.17 | |
| Comparative Example 5 | 475 | 66.35/10.99 | 75.29/19.93 | 85.41/30.06 | 10.99 | |
| Comparative Example 6 | 467 | 66.40/7.82 | 74.21/15.63 | 86.00/27.42 | 7.82 | |
| Comparative Example 7 | | 67.86/25.67 | | | 25.67 | |
| Comparative Example 8 | | 69.19/15.01 | | | 15.01 | |
| Comparative Example 9 | | 67.33/14.26 | | | 14.26 | |
| Compound 1 | 475 | 70.31/11.52 | 75.84/17.05 | 75.73/16.95 | 11.52 | |
| Compound 2 | 464 | 73.10/12.36 | 75.57/14.83 | 81.82/21.08 | 12.36 | |
| Compound 3 | 466 | 62.84/5.22* | 71.73/14.10 | 83.04/25.42 | 14.10 | |
| Compound 4 | 464 | 78.26/17.70 | 76.56/16.00 | 83.92/23.36 | 16.00 | |
| Compound 8 | | 73.59/29.07 | | | 29.07 | |
| Compound 56 | | 75.16/21.18 | | | 21.18 | |
| Compound 57 | | 76.07/22.91 | | | 22.91 | |
| Compound 58 | | 77.67/24.97 | | | 24.97 | |

Figure 7:
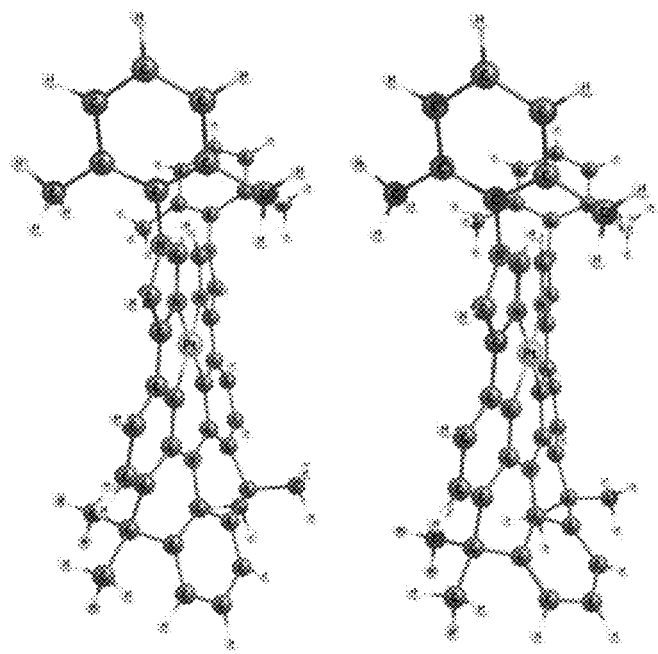
FIG. 7 shows the geometry for Compound 3, which shows the N-phenyl bond intact. The left structure shows the optimized ground state triplet. The right structure shows an optimized N-phenyl bond-breaking triplet. Slight differences in the geometry of the phenyl and germinal dimethyl groups can be seen, which may account for the small calculated energy difference of 5.22 kcal/mol.

As shown in TABLE 2, calculations indicate that linking the phenyl in the N-phenyl position to the phenyl of the phenlyimidazole ligand increases the N-phenyl bond strength. In the triplet state, Comparative Example 1 has an N-phenyl bond strength of 8.02 kcal/mole. Comparative Examples 4 and 6, without tethering substitutions are found to have similar N-phenyl bond strength compared to Comparative Example 1. Compound 2 is shown to have a. stronger N-phenyl bond of 10.99 kcal/mol, however, the triplet energy of 475 nm is lower than Comparative Example 1. Tethered examples, Compounds 1-4 are found to have stronger N-phenyl bonds while in several cases retaining the desirable high triplet energy. A special case is found for Compound 3, which is tethered by geminal dimethyl groups on both sides. As shown in the table, designated by "*", these substitutions are calculated to have a large impact on the N-phenyl bond strength. Linking the phenyl group to the complex on both sides prevents the phenyl from twisting or moving out of the bonding position. Optimization results in a distorted geometry of Compound 3, such that the phenyl is not directly lined up with the nitrogen and the N-phenyl bond. The distortion results in a relatively small calculated energy difference of 5.22 kcal/mol for the N-phenyl bond strength of Compound 3. However, the N-phenyl bond is reformed, so the small difference in energy is related to the slight geometry difference, not a broken bond. The calculated geometric distortion for Compound 3 is shown in FIG. 7. Thus, tethering (or bridging) the phenyl group on both sides retains the N-phenyl bond and shifts the lowest bond strength to the N-aryl bond. In addition the other structures, Compound 1, 2 and 4, are found to have greater N-phenyl bond strengths compared to Comparative Example 1.

Calculating the Naryl bond strengths was done by removing the dimethylphenyl group and separately calculating the energies of the doublet complex and dimethylphenyl. There are no major differences in the N-aryl bond strengths besides the differing ground state triplet energies between the complexes.

Finally, calculations were performed on the N-phenyl-2 bond in which the bridging N atom is detached from the phenyl of the phenyl imidazole ligand. This bond is calculated to be the strongest bond of the three investigated except for complex Compound 1. The N-phenyl-2 bond strength is calculated to be a mere 0.1 kcal/mol weaker than the N-aryl bond for complex Compound 1. In all cases, the N-phenyl-2 bond is never calculated to be the weakest bond of the complex. This suggests that the breaking the N-phenyl-2 bond is not a significant source of decomposition. In addition, Compound 8, 56, 57, and 58 further demonstrate the versatility of this approach. In each case the N-atyl bond strength is calculated to be greater than the corresponding untethered comparative example, Compartative Example 7, 8 and 9.

Example 2

MALDI-TOF Fragmentation

Figure 4:
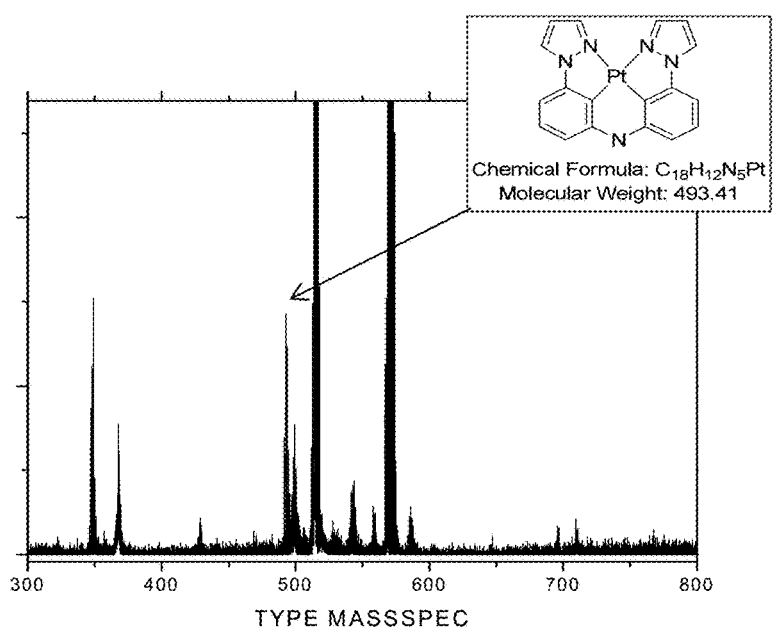
FIG. 4 shows a positive-mode MALDI-TOF mass spectrum for Host 1 and Comparative Example 3. The arrow shows the major fragment, which is the loss of N-phenyl. The inset shows the structure and mass of the bond-broken photoproduct.
Figure 5:
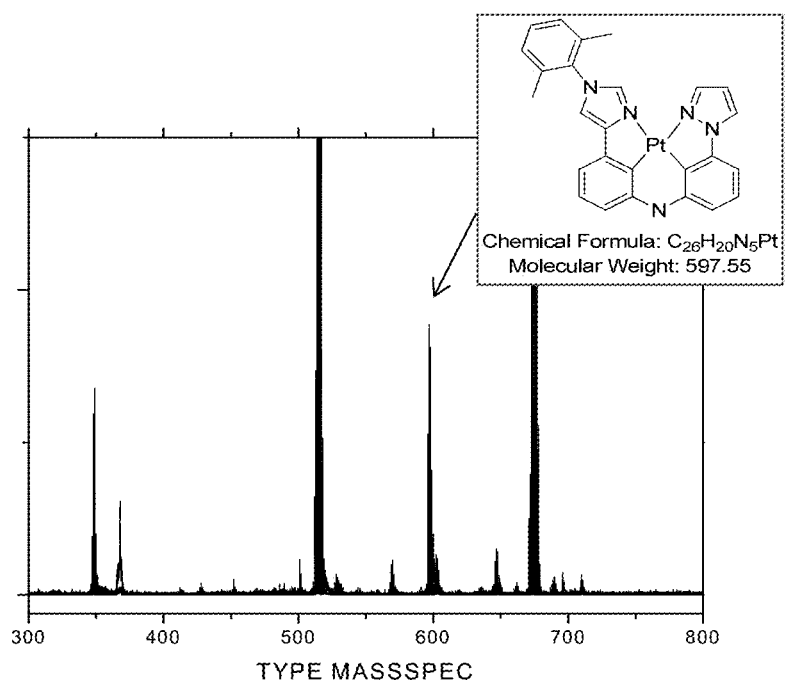
FIG. 5 shows a positive-mode MALDI-TOF mass spectrum for Host 1 and Comparative Example 2. The arrow shows the major fragment, which is the loss of N-phenyl. The inset shows the structure and mass of the bond-broken photoproduct.
Figure 6:
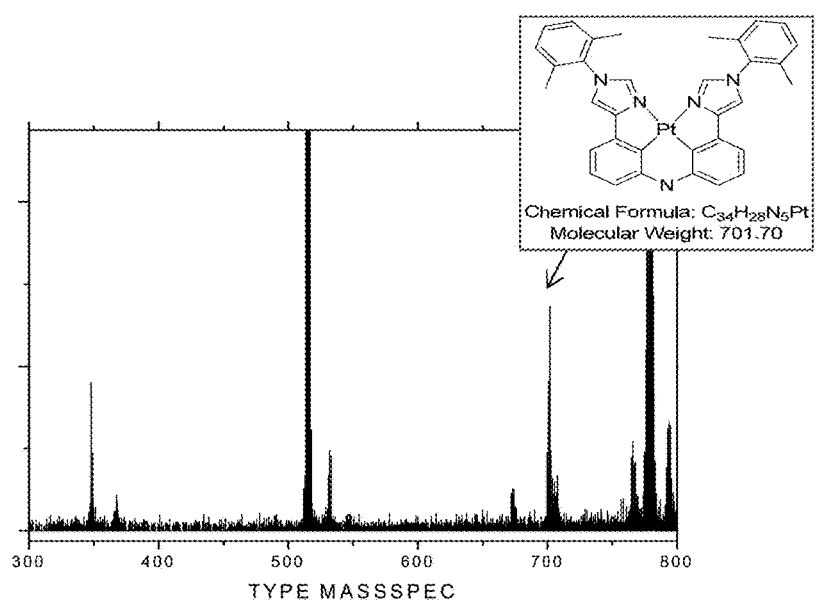
FIG. 6 shows a positive-mode MALDI-TOF mass spectrum for Host 1 and Comparative Example 1. The arrow shows the major fragment, which is the loss of N-phenyl. The inset shows the structure and mass of the bond-broken photoproduct.

The relative instability of the N—C ring bond is demonstrated experimentally by excited state fragmentation patterns observed in a MALDI mass spectrometer. Host 1 and Comparative Examples 1-3 at an approximate 20 wt % ratio were dissolved in di chloromethane and spot cast on an Applied Biosystems Voyager DE-STR MALDI sample target plate. The samples were analyzed in the positive mode. FIGS. 4-6 show that there is a major fragment that results from the loss of the N-phenyl ring, i.e. N—C ring bond breakage. In each case, it is found that the broken N—C bond is an abundant fragment associated with the dopant.

Without being bound to any theory, it is believed that linking or tethering (or bridging) the C-Ring back to the complex will result in an improvement in stability particularly for phosphorescent metal complexes with bridging aryl amine substitutions.

It is understood that the various embodiments described herein are by way of example only, and are not intended to limit the scope of the invention. For example, many of the materials and structures described herein may be substituted with other materials and structures without deviating from the spirit of the invention. The present invention as claimed may therefore include variations from the particular examples and preferred embodiments described herein, as will be apparent to one of skill in the art. It is understood that various theories as to why the invention works are not intended to be limiting.

We claim:
1. A compound having Formula (IV):

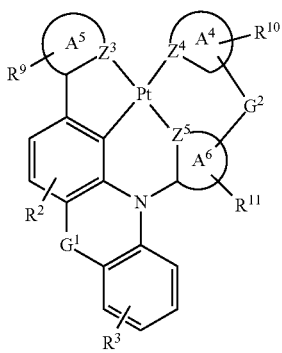

wherein rings $A^4$, $A^5$, and $A^6$ are independently five- or six-membered carbocyclic or heterocyclic aromatic rings having 0-3 nitrogen atoms and 0-1 additional heteroatoms selected from the group consisting of oxygen, sulfur, and selenium;
wherein $Z^3$, $Z^4$, and $Z^5$ are independently carbon or nitrogen;
wherein $G^1$ is $CR^4R^5$;
wherein $R^2$ represents mono-substitution or di-substitution wherein each $R^2$ is selected independently from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof, and wherein any two adjacent $R^2$ may optionally combine to form a ring, which can be further substituted;
wherein $R^3$ represents mono, di-, tri, or tetra-substitution, wherein each $R^3$ is selected independently from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof, and wherein any two adjacent $R^3$ may optionally combine to form a ring, which can be further substituted;
wherein $R^4$ and $R^5$ are independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof, and wherein $R^4$ and $R^5$ may optionally combine to form a ring, which can be further substituted;
wherein any of $R^4$ or $R^5$ may optionally combine with any $R^2$ or $R^3$ to form a ring system, which can be further substituted;
wherein $G^2$ is sulfur, $CR^{12}R^{12a}$, $SiR^{12}R^{12a}$, $CR^{12}R^{12a}$, or $NR^{12}$; wherein each $R^{12}$ and $R^{12a}$ is selected independently from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof, and wherein (i) when $G^2$ is $NR^{12}$ and $R^{12}$ is aryl or heteroaryl, the aryl or heteroaryl $R^{12}$ combines with any one $R^{10}$ to form a ring system, which can be further substituted, (ii) when $G^2$ is $CR^{12}R^{12a}$ or $SiR^{12}R^{12a}$, and at least one of $R^{12}$ or $R^{12}a$ is aryl or heteroaryl, $R^{12}$ and $R^{12a}$ combine with each other, or one aryl or heteroaryl $R^{12}$ or $R^{12a}$ combines with any one $R^{10}$ to form a ring system, which can be further substituted, and (iii) for other than (i) and (ii), $R^{12}$ and $R^{12a}$ may optionally combine with each other or with any one $R^{10}$ or $R^{11}$ to form a ring system, which can be further substituted;
wherein $R^9$ and $R^{10}$ represent mono, di-, tri, or tetra-substitution, wherein each $R^9$ or $R^{10}$ is selected independently from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof, and wherein any two adjacent $R^9$ or any two adjacent $R^{10}$ may optionally combine to form a ring, which can be further substituted;
wherein $R^{11}$ represents mono, di-, or tri-substitution, wherein each $R^{11}$ is selected independently from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof, and wherein any two adjacent $R^{11}$ may optionally combine to form a ring, which can be further substituted;
wherein any $R^3$ may optionally combine with any $R^{11}$ to form a ring system, which can be further substituted; and
wherein any $R^2$ may optionally combine with any $R^9$ to form a ring system, which can be further substituted.

2. A first device comprising a first organic light emitting device, which comprises:
an anode;
a cathode; and
an organic layer disposed between the anode and the cathode, which comprises a compound having Formula (IV):

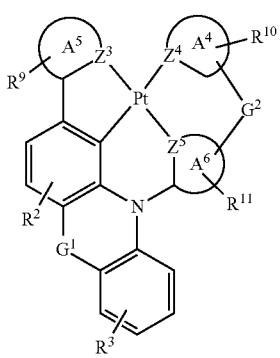

(IV)

wherein rings $A^4$, $A^5$, and $A^6$ are independently five- or six-membered carbocyclic or heterocyclic aromatic rings having 0-3 nitrogen atoms and 0-1 additional heteroatoms selected from the group consisting of oxygen, sulfur, and selenium;

wherein $Z^3$, $Z^4$, and $Z^5$ are independently carbon or nitrogen;

wherein $G^1$ is $CR^4R^5$;

wherein $R^2$ represents mono-substitution or di-substitution wherein each $R^2$ is selected independently from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof, and wherein any two adjacent $R^2$ may optionally combine to form a ring, which can be further substituted;

wherein $R^3$ represents mono, di-, tri, or tetra-substitution, wherein each $R^3$ is selected independently from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof, and wherein any two adjacent $R^3$ may optionally combine to form a ring, which can be further substituted;

wherein $R^4$ and $R^5$ are independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof, and wherein $R^4$ and $R^5$ may optionally combine to form a ring, which can be further substituted;

wherein any of $R^4$ or $R^5$ may optionally combine with any $R^2$ or $R^3$ to form a ring system, which can be further substituted;

wherein $G^2$ is sulfur, $CR^{12}R^{12a}$, $SiR^{12}R^{12a}$, $CR^{12}R^{12a}$, or $NR^{12}$; wherein each $R^{12}$ and $R^{12a}$ is selected independently from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof, and wherein (i) when $G^2$ is $NR^{12}$ and $R^{12}$ is aryl or heteroaryl, the aryl or heteroaryl $R^{12}$ combines with any one $R^{10}$ to form a ring system, which can be further substituted, (ii) when $G^2$ is $CR^{12}R^{12a}$ or $SiR^{12}R^{12a}$, and at least one of $R^{12}$ or $R^{12a}$ is aryl or heteroaryl, $R^{12}$ and $R^{12a}$ combine with each other, or one aryl or heteroaryl $R^{12}$ or $R^{12a}$ combines with any one $R^{10}$ to form a ring system, which can be further substituted, and (iii) for other than (i) and (ii), $R^{12}$ and $R^{12a}$ may optionally combine with each other or with any one $R^{10}$ or $R^{11}$ to form a ring system, which can be further substituted;

wherein $R^9$ and $R^{10}$ represent mono, di-, tri, or tetra-substitution, wherein each $R^9$ or $R^{10}$ is selected independently from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof, and wherein any two adjacent $R^9$ or any two adjacent $R^{10}$ may optionally combine to form a ring, which can be further substituted;

wherein $R^{11}$ represents mono, di-, or tri-substitution, wherein each $R^{11}$ is selected independently from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof, and wherein any two adjacent $R^{11}$ may optionally combine to form a ring, which can be further substituted;

wherein any $R^3$ may optionally combine with any $R^{11}$ to form a ring system, which can be further substituted; and wherein any $R^2$ may optionally combine with any $R^9$ to form a ring system, which can be further substituted.

3. The first device of claim 2, wherein the first device is a consumer product.

4. The first device of claim 2, wherein the first device is an organic light-emitting device.

5. The first device of claim 2, wherein the first device comprises a light panel.

6. The first device of claim 2, wherein the organic layer is an emissive layer and the compound is an emissive dopant.

7. The first device of claim 2, wherein the organic layer is an emissive layer and the compound is a non-emissive dopant.

8. The first device of claim 2, wherein the organic layer further comprises a host.

9. The first device of claim 8, wherein the host comprises a triphenylene containing benzo-fused thiophene or benzo-fused furan;

wherein any substituent in the host is an unfused substituent independently selected from the group consisting of $C_nH_{2n+1}$, $OC_nH_{2n+1}$, $OAr_1$, $N(C_nH_{2n+1})_2$, $N(Ar_1)(Ar_2)$, $CH=CH-C_nH_{2n+1}$, $C\equiv C-C_nH_{2n+1}$, $Ar_1$, $Ar_1$-$Ar_2$, and $C_nH_{2n}-Ar_1$, or the host has no substitutions;

wherein n is from 1 to 10; and wherein $Ar_1$ and $Ar_2$ are independently selected from the group consisting of benzene, biphenyl, naphthalene, triphenylene, carbazole, and heteroaromatic analogs thereof.

10. The first device of claim 8, wherein the host comprises a compound selected from the group consisting of: carbazole, dibenzothiophene, dibenzofuran, dibenzoselenophene, azacarbazole, aza-dibenzothiophene, aza-dibenzofuran, and aza-dibenzoselenophene.

11. The first device of claim 8, wherein the host is selected from the group consisting of:
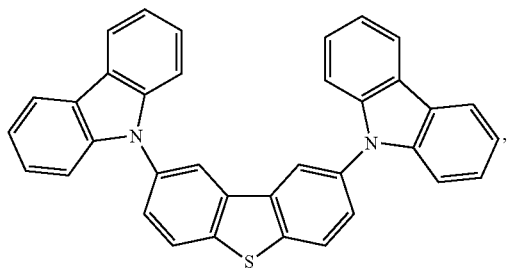
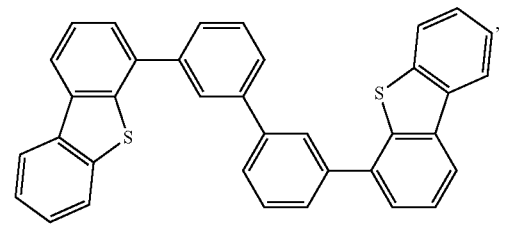
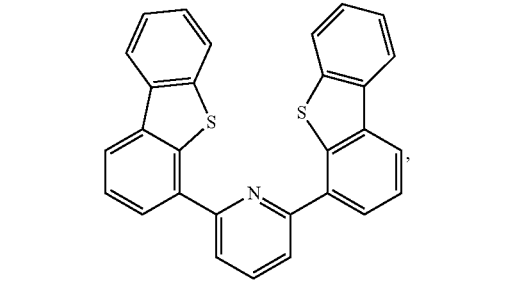
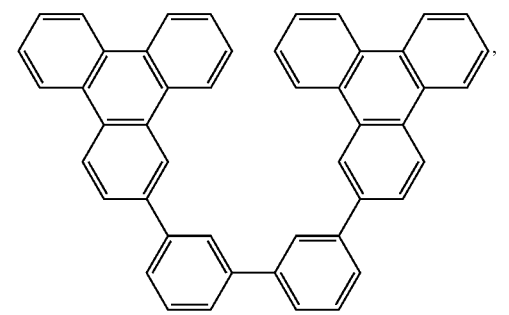
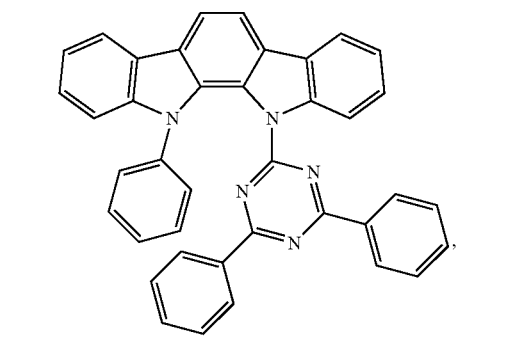
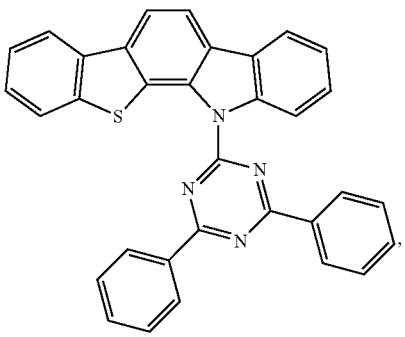
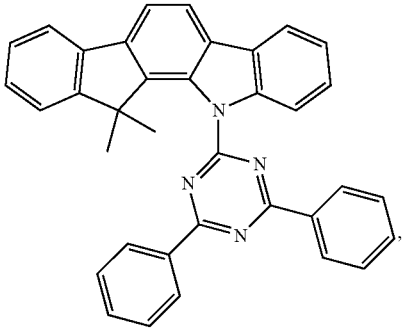
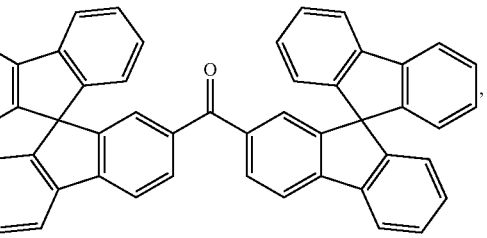
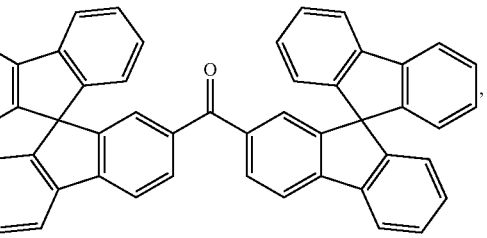

-continued

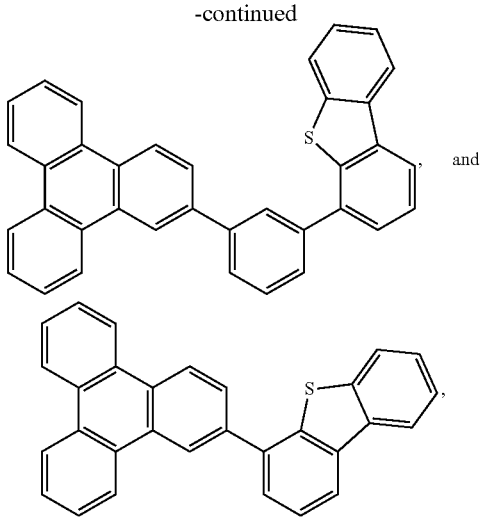

and combinations thereof.

12. The first device of claim 8, wherein the host comprises a metal complex.

13. The compound of claim 1, which is selected from the group consisting of:

Compound 14

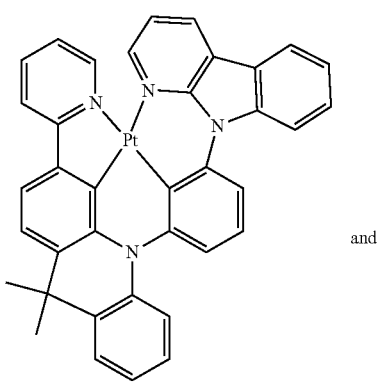

and

-continued

Compound 26

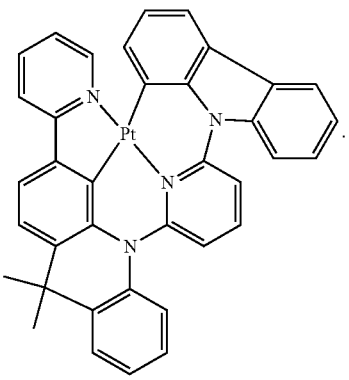

14. The compound of claim 1, wherein $G_2$ is $CR^{12}R^{12a}$, and at least one of $R^{12}$ or $R^{12a}$ is aryl or heteroaryl, and $R^{12}$ and $R^{12a}$ combine with each other or one aryl or heteroaryl $R^{12}$ or $R^{12a}$ combines with any one $R^{10}$.

15. The compound of claim 1, wherein $G_2$ is $SiR^{12}R^{12a}$, and at least one of $R^{12}$ or $R^{12a}$ is aryl or heteroaryl, and $R^{12}$ and $R^{12a}$ combine with each other or one aryl or heteroaryl $R^{12}$ or $R^{12a}$ combines with any one $R^{10}$.

16. The compound of claim 1, wherein $G^2$ is $NR^{12}$, and $R^{12}$ is aryl or heteroaryl, and $R^{12}$ combines with any one $R^{10}$.

17. The compound of claim 1, wherein $G^2$ is S.

18. The compound of claim 1, wherein $R^{12}$ or $R^{12a}$ are selected independently from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, acyl, carbonyl, carboxylic acids, ester, nitrile, isonitrile, sulfanyl, sulfinyl, sulfonyl, phosphino, and combinations thereof; and $R^{12}$ or $R^{12a}$ may optionally combine with each other or with any one $R^{10}$ or $R^{11}$ to form a ring system, which can be further substituted.

\* \* \* \* \*